US008324399B2

(12) United States Patent
Morita et al.

(10) Patent No.: US 8,324,399 B2
(45) Date of Patent: Dec. 4, 2012

(54) HEAT RESISTANCE IMPROVER AND REVERSIBLE THERMOSENSITIVE RECORDING MEDIUM

(75) Inventors: Mitsunobu Morita, Numazu (JP); Jun Maruyama, Yokohama (JP)

(73) Assignee: Ricoh Company, Ltd., Tokyo (JP)

( * ) Notice: Subject to any disclaimer, the term of this patent is extended or adjusted under 35 U.S.C. 154(b) by 763 days.

(21) Appl. No.: 12/405,593

(22) Filed: Mar. 17, 2009

(65) Prior Publication Data

US 2009/0239747 A1 Sep. 24, 2009

(30) Foreign Application Priority Data

Mar. 18, 2008 (JP) ................................ 2008-070456

(51) Int. Cl.
*B41M 5/337* (2006.01)
*C07D 403/00* (2006.01)

(52) U.S. Cl. ....................................... 548/255; 503/209

(58) Field of Classification Search ........................ None
See application file for complete search history.

(56) References Cited

U.S. PATENT DOCUMENTS

| | | | |
|---|---|---|---|
| 6,048,387 | A | 4/2000 | Shibahashi et al. |
| 6,291,117 | B1 | 9/2001 | Hosaka et al. |
| 7,371,708 | B2 | 5/2008 | Arai et al. |
| 2002/0063244 | A1 | 5/2002 | Nakashima et al. |
| 2002/0072472 | A1 | 6/2002 | Furuya et al. |
| 2005/0106491 | A1 | 5/2005 | Henshall et al. |
| 2005/0176582 | A1 | 8/2005 | Arai et al. |
| 2007/0285488 | A1 | 12/2007 | Ishimi et al. |

FOREIGN PATENT DOCUMENTS

| | | |
|---|---|---|
| CN | 1660601 | 8/2005 |
| CN | 1958704 | 5/2007 |
| EP | 0131468 | 1/1985 |
| EP | 0908501 A1 | 4/1999 |
| EP | 1179435 A1 | 2/2002 |
| EP | 1552952 A1 | 7/2005 |
| EP | 1834796 A2 | 9/2007 |
| JP | 5-150433 | 6/1993 |
| JP | 6-53733 | 7/1994 |
| JP | 7-88471 | 9/1995 |
| JP | 9-34057 | 2/1997 |
| JP | 10-140089 | 5/1998 |
| JP | 2003-521550 | 7/2003 |
| JP | 2004-276410 | 10/2004 |
| JP | 2006-82252 | 3/2006 |
| JP | 3781587 | 3/2006 |
| JP | 2006-88445 | 4/2006 |
| JP | 2007-138184 | 6/2007 |
| JP | 4126364 | 5/2008 |
| WO | WO99/23151 | 5/1999 |
| WO | WO03/074285 A1 | 9/2003 |
| WO | WO2007/099053 | 9/2007 |

OTHER PUBLICATIONS

Jul. 2, 2010 Chinese official action in connection with counterpart Chinese patent application.

Jul. 7, 2009 European search report in connection with a counterpart European patent application No. 09 15 5382.

*Primary Examiner* — Bruce H Hess
(74) *Attorney, Agent, or Firm* — Cooper & Dunham LLP

(57) ABSTRACT

A heat resistance improver including a heat resistance improving component which has a benzotriazole skeleton having an electron attractive group and a reactive aliphatic hydroxyl group or a reactive aliphatic mercapto group, wherein the heat resistance improver is used in a reversible thermosensitive recording medium.

10 Claims, 2 Drawing Sheets

HEAT RESISTANCE IMPROVER AND REVERSIBLE THERMOSENSITIVE RECORDING MEDIUM

BACKGROUND OF THE INVENTION

1. Field of the Invention

The present invention relates to a heat resistance improver which is considerably resistant to heat and light applied during repetitive use outdoor and which is used in a reversible thermosensitive recording medium, and to a reversible thermosensitive recording medium.

2. Description of the Related Art

Conventionally known thermosensitive recording media employ color development reaction between an electron-donating color-developing compound (hereinafter may be referred to as a "color former" or "leuco dye") and an electron-accepting compound (hereinafter may be referred to as a "color developer"). With the development of office automation, the thermosensitive recording media have widely been used as output sheets for use in facsimiles, word processors and scientific measurement instruments. In recent years, they have also been used as magnetic thermosensitive cards such as prepaid cards and point cards. Thus, in view of environmental problems and recycling, a reversible thermosensitive recording medium capable of being overwritten as often as desired has been developed.

In order for the thermosensitive recording media to exhibit improved light resistance, an ultraviolet (UV) ray-cutting agent is incorporated into a layer constituting them. Examples of known ultraviolet (UV) ray-cutting agents include UV-reflecting agents and UV absorbers. Examples of the UV-reflecting agent include metal oxides such as zinc oxide. Examples of the UV absorbers include benzotriazole (BTA)-based UV absorbers, benzophenone (BP)-based UV absorbers, salicylic acid (SA)-based UV absorbers and cyanoacetic acid (CA)-based UV absorbers. Among them, BTA-based UV absorbers and BP-based UV absorbers are preferred, since their light absorption wavelength is advantageous from the viewpoint of improving light resistance of the media.

The reversible thermosensitive recording media are very advantageous in that they can be repeatedly used. However, in the reversible thermosensitive recording media containing the BTA-based or BP-based UV absorber, the UV absorber (UVA) is bled out after repetitive use, resulting in that the effect thereof cannot be attained for a long period of time.

In order to prevent the absorber from bleeding out, Japanese Patent Application Laid-Open (JP-A) No. 2004-276410 proposes use of a polymer formed from the UVA. Also, Japanese Patent (JP-B) No. 3781587 proposes that a reactive residue is introduced into the UVA itself, and the thus-obtained UVA is reacted with a crosslinking agent in the matrix for immobilization.

These can sufficiently prevent the absorber from bleeding out when the recording medium is used indoor under artificial light.

In recent years, reversible thermosensitive recording media have been increasingly required to be used as a visually recognized medium for RF-ID information, and have been increasingly used outdoor under natural sunlight in, for example, material management in logistics. The natural light is higher in UV dose than the artificial light. Thus, the above-described reversible thermosensitive recording media are not practically applicable outdoor, since they have insufficient UV absorbability.

Also, in addition to the above techniques of UV cutting, JP-A Nos. 2006-88445 and 2006-82252 disclose that a reversible thermosensitive recording medium is prevented from oxidation so as to exhibit improved light resistance. Specifically, these propose provision of a layer which contains a resin capable of forming a hydrogen bond and preventing permeation of oxygen. The formed reversible thermosensitive recording medium exhibits a certain light resistance under low humidity conditions, but exhibits no light resistance under high humidity conditions since the resin used has water solubility and water absorbability.

Also, in order for a UV absorber itself to exhibit enhanced UV absorbability, the UV absorber has been improved so as to absorb light having a longer wavelength. Such UV absorbers that absorb light having a longer wavelength are disclosed in, for example, JP-A No. 2003-521550, Japanese Patent Application Publication (JP-B) Nos. 06-53733 and 07-88471, and JP-A Nos. 09-34057, 10-140089, 05-150433 and 2007-138184.

Reversible thermosensitive recording media containing a UV absorber disclosed in the above literatures involve fogging caused by an erase bar, do not have surfaces resistant to repetitive use outdoor, and do not have sufficient light resistance and heat resistance with respect to formed images and images after erasure. Thus, demand has arisen for development of further improved reversible thermosensitive recording media.

BRIEF SUMMARY OF THE INVENTION

An object of the present invention is to provide a heat resistance improver which forms surfaces resistant to repetitive use outdoor, no fogging caused by an erase bar, and excellent light resistance and heat resistance with respect to formed images and images after erasure and which is suitably used for a reversible thermosensitive recording medium; and a reversible thermosensitive recording medium containing the heat resistance improver.

Means for solving the problems pertinent in the art are as follows.

<1> A heat resistance improver including:

a heat resistance improving component which has a benzotriazole skeleton having an electron attractive group and a reactive aliphatic hydroxyl group or a reactive aliphatic mercapto group, wherein the heat resistance improver is used in a reversible thermosensitive recording medium.

<2> The heat resistance improver according to <1> above, wherein the electron attractive group is any one selected from a halogen atom, —$NO_2$, —CN, —$CF_3$, $R^1$—$SO_2$—, $R^1$—CO—, $R^1$—OOC— and $R^1$NHCO—, where $R^1$ represents a hydrogen atom, a halogen atom, an alkyl group, a cycloalkyl group, an alkenyl group, an aryl group or an aralkyl group.

<3> The heat resistance improver according to any one of <1> and <2> above, wherein the heat resistance improving component is a compound represented by the following General Formula (1):

General Formula (1)

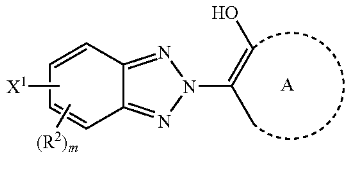

where A represents an aromatic ring, a condensed ring, a hetero aromatic ring or a hetero condensed ring each of which has, as a substituent, a reactive aliphatic hydroxyl group or a reactive aliphatic mercapto group and may have other substituent(s); $R^2$ represents a hydrogen atom, a halogen atom, an alkyl group, an alkyloxy group or a halogen atom; m is an integer of 0 to 3; and $X^1$ represents an electron attractive group selected from a halogen atom, —$NO_2$, —CN, —$CF_3$, $R^1$—$SO_2$—, $R^1$—CO—, $R^1$—OOC— and $R^1$NHCO—, where $R^1$ represents a hydrogen atom, a halogen atom, an alkyl group, a cycloalkyl group, an alkenyl group, an aryl group or an aralkyl group.

<4> The heat resistance improver according to any one of <1> to <3> above, wherein the heat resistance improving component is a compound represented by the following General Formula (2):

General Formula (2)

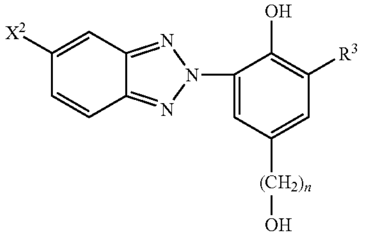

where $X^2$ represents a hydrogen atom, a halogen atom, —$NO_2$, —CN, —$CF_3$ or an alkyloxycarbonyl group; $R^3$ represents a hydrogen atom, a linear or branched alkyl group having 1 to 8 carbon atoms, —CHO or —CH═N—$R^4$, where $R^4$ represents an alkyl group, an aryl group, an alkenyl group or an aralkyl group each of which may have a substituent; and n is an integer of 1 to 8; with the proviso that when $R^3$ is a linear or branched alkyl group having 1 to 8 carbon atoms, $X^2$ is not a hydrogen atom.

<5> The heat resistance improver according to any one of <1> and <2> above, wherein the heat resistance improving component is a reactive hydroxyl group-containing polymer produced through polymerization of at least a compound represented by the following General Formula (3) and hydroxyalkyl(meth)acrylate:

General Formula (3)

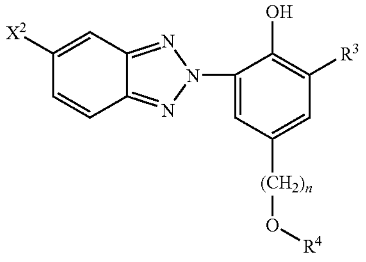

where $X^2$ represents a hydrogen atom, a halogen atom, —$NO_2$, —CN, —$CF_3$ or an alkyloxycarbonyl group; $R^3$ represents a hydrogen atom, a linear or branched alkyl group having 1 to 8 carbon atoms, —CHO or —CH═N—$R^4$, where $R^4$ represents an alkyl group, an aryl group, an alkenyl group or an aralkyl group each of which may have a substituent; n is an integer of 1 to 8; with the proviso that when $R^3$ is a linear or branched alkyl group having 1 to 8 carbon atoms, $X^2$ is not a hydrogen atom; and $R^4$ represents a polymerizable unsaturated hydrocarbon group.

<6> The heat resistance improver according to <5> above, wherein the heat resistance improving component is a compound represented by the following General Formula (4):

General Formula (4)

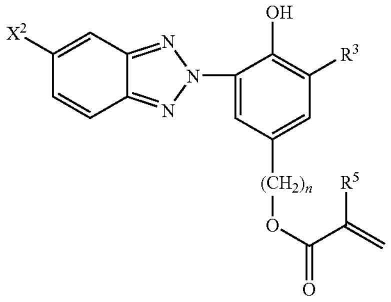

where $X^2$, n and $R^3$ have the same meanings as defined in General Formula (3); and $R^5$ represents a hydrogen atom or a methyl group.

<7> The heat resistance improver according to any one of <4> to <6> above, wherein the alkyloxycarbonyl group represented by $X^2$ is a linear or branched alkyloxycarbonyl group having 1 to 6 carbon atoms.

<8> A heat resistance improver including:

a heat resistance improving component which has a benzotriazole skeleton whose carbon atom is substituted with an electronegative atom and which has a reactive aliphatic hydroxyl group or a reactive aliphatic mercapto group, wherein the heat resistance improver is used in a reversible thermosensitive recording medium.

<9> The heat resistance improver according to <8> above, wherein the heat resistance improving component is a compound represented by the following General Formula (5):

General Formula (5)

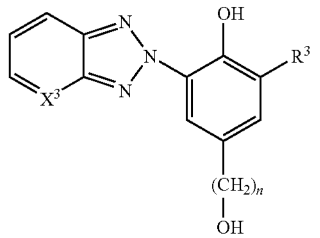

where $X^3$ represents an electronegative atom; $R^3$ represents a hydrogen atom, a linear or branched alkyl group having 1 to 8 carbon atoms, —CHO or —CH═N—$R^4$, where $R^4$ represents an alkyl group, an aryl group, an alkenyl group or an aralkyl group each of which may have a substituent; and n is an integer of 1 to 8.

<10> The heat resistance improver according to <9> above, wherein the heat resistance improving component is a compound represented by the following General Formula (6):

General Formula (6)

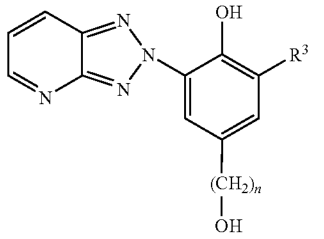

where $R^3$ and n have the same meanings as defined in General Formula (5).

<11> The heat resistance improver according to <8> above, wherein the heat resistance improving component is a reactive hydroxyl group-containing polymer produced through polymerization of at least a compound represented by the following General Formula (7) and hydroxyalkyl (meth)acrylate:

General Formula (7)

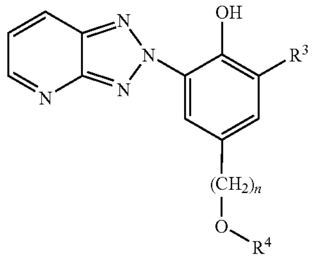

where $R^3$ represents a hydrogen atom, a linear or branched alkyl group having 1 to 8 carbon atoms, —CHO or —CH═N—$R^4$, where $R^4$ represents an alkyl group, an aryl group, an alkenyl group or an aralkyl group each of which may have a substituent; n is an integer of 1 to 8; and $R^4$ represents a polymerizable unsaturated hydrocarbon group.

<12> The heat resistance improver according to <11> above, wherein the heat resistance improving component is a polymer produced through polymerization between a compound represented by the following General Formula (8) and hydroxyalkyl(meth)acrylate:

General Formula (8)

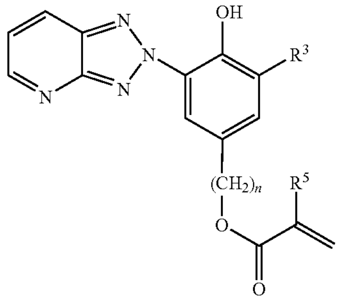

where $R^3$ and n have the same meanings as defined in General Formula (7); and $R^5$ represents a hydrogen atom or a methyl group.

<13> The heat resistance improver according to any one of <5> to <7>, <11> and <12> above, wherein the polymer has a mass average molecular weight of 1,000 to 200,000.

<14> The heat resistance improver according to any one of <5> to <7> and <11> to <13> above, wherein the polymer has a hydroxyl value of 100 mgKOH/g or higher and an acid value of 5 mgKOH/g or lower.

<15> A reversible thermosensitive recording medium including:

a support, a reversible thermosensitive recording layer which contains an electron-donating color-developing compound and an electron-accepting compound, and which reversibly changes in color tone depending on a change in temperature, and a heat resistance improving layer, the reversible thermosensitive recording layer and the heat resistance improving layer being laid over the support in this order, wherein the heat resistance improving layer includes the heat resistance improver according to any one of <1> to <14> above.

<16> The reversible thermosensitive recording medium according to <15> above, wherein the heat resistance improving layer has a transmittance of 20% or lower with respect to an ultraviolet ray having a wavelength of 390 nm.

<17> The reversible thermosensitive recording medium according to any one of <15> and <16> above, wherein the heat resistance improving layer includes a binder resin, and the binder resin is an ester polyol resin or an acrylic polyol resin.

<18> The reversible thermosensitive recording medium according to any one of <15> to <17> above, wherein the reactive aliphatic hydroxyl group or the reactive aliphatic mercapto group contained in the heat resistance improver is crosslinked with an isocyanate compound.

<19> The reversible thermosensitive recording medium according to any one of <15> to <18> above, further including a gas barrier layer.

The present invention can provide a heat resistance improver which forms surfaces resistant to repetitive use outdoor, no fogging caused by an erase bar, and excellent light resistance and heat resistance with respect to formed images and images after erasure and which is suitably used for a reversible thermosensitive recording medium; and a reversible thermosensitive recording medium containing the heat resistance improver. These can solve existing problems pertinent in the art.

DETAILED DESCRIPTION OF THE INVENTION

Heat Resistance Improver

Figure 1:
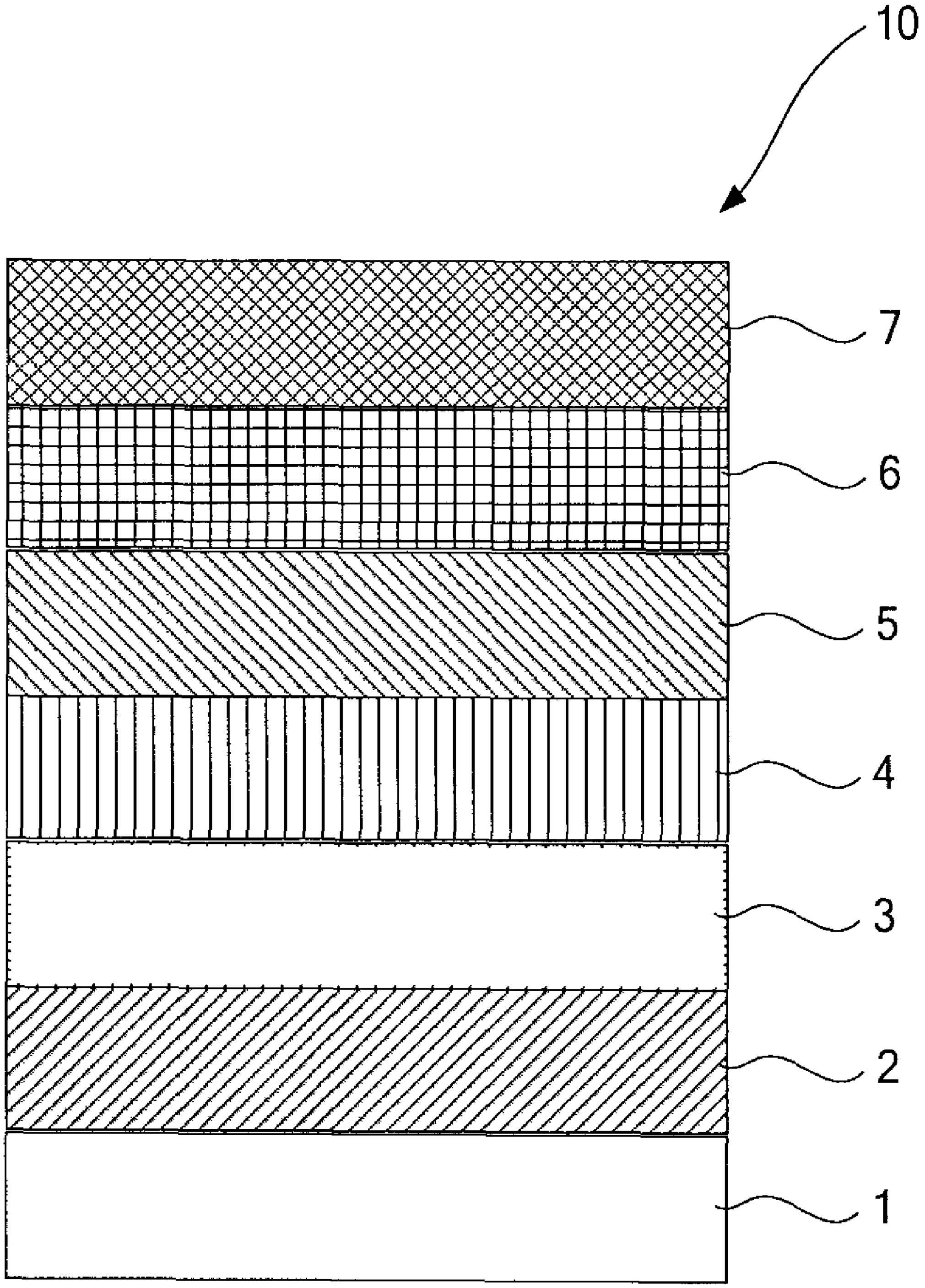
FIG. 1 is a cross-sectional view exemplarily showing a layer structure of a reversible thermosensitive recording medium of the present invention.

A heat resistance improver according to a first embodiment of the present invention is used in a reversible thermosensitive recording medium; and contains a heat resistance improving component which has a benzotriazole skeleton having an electron attractive group and a reactive aliphatic hydroxyl group or a reactive aliphatic mercapto group, and optionally contains other components in accordance with needs.

A heat resistance improver according to a second embodiment of the present invention is used in a reversible thermosensitive recording medium; and contains a heat resistance improving component which has a benzotriazole skeleton whose carbon atom is substituted with an electronegative atom and which has a reactive aliphatic hydroxyl group or a reactive aliphatic mercapto group, and optionally contains other components in accordance with needs.

Preferred examples of the electron attractive group include a halogen atom, $—NO_2$, —CN, $—CF_3$, $R^1—SO_2—$, $R^1—CO—$, $R^1—OOC—$ and $R^1NHCO—$ (where $R^1$ represents a hydrogen atom, a halogen atom, an alkyl group, a cycloalkyl group, an aryl group, a cycloalkyl group, an alkenyl group, an aryl group, an aralkyl group, or a group formed by combining these groups).

Examples of the alkyl group represented by $R^1$ include methyl, ethyl, n-propyl, iso-propyl, t-butyl, pentyl, hexyl, octyl and dodecyl.

Examples of the cycloalkyl group represented by $R^1$ include cyclopentyl and cyclohexyl.

Examples of the alkenyl group represented by $R^1$ include vinyl, 2-propenyl, 3-butenyl, 1-methyl-3-propenyl, 1-methyl-3-butenyl, 4-hexenyl and cyclohexenyl.

Examples of the aryl group represented by $R^1$ include phenyl, 1-naphthyl and 2-naphthyl.

Examples of the aralkyl group represented by $R^1$ include benzyl and phenethyl.

Examples of the reactive aliphatic hydroxyl group include hydroxyethyl, hydroxypropyl and hydroxybutyl.

Examples of the reactive aliphatic mercapto group include mercaptoethyl, mercaptopropyl and mercaptobutyl.

In a first embodiment, the heat resistance improver preferably contains, as a heat resistance improving component, a compound represented by the following General Formula (1), more preferably a compound represented by the following General Formula (2).

General Formula (1)

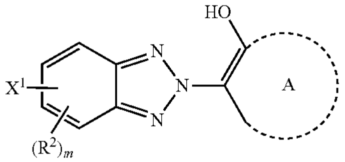

where A represents an aromatic ring, a condensed ring, a hetero aromatic ring or a hetero condensed ring, each of which has, as at a substituent, a reactive aliphatic hydroxyl group or a reactive aliphatic mercapto group and may have other substituent(s); $R^2$ represents a hydrogen atom, a halogen atom, an alkyl group, an alkyloxy group or a halogen atom; m is an integer of 0 to 3; and $X^1$ represents an electron attractive group selected from a halogen atom, $—NO_2$, —CN, $—CF_3$, $R^1—SO_2—$, $R^1—CO—$, $R^1—OOC—$ and $R^1NHCO—$ (where $R^1$ represents a halogen atom, a hydrogen atom, an alkyl group, a cycloalkyl group, an alkenyl group, an aryl group or an aralkyl group).

In General Formula (1), A represents an aromatic ring, a condensed ring, a hetero aromatic ring or a hetero condensed ring such as phenyl, naphthy, pyridyl, thiazolyl, oxazolyl, imidazolyl, quinolyl, benzothiazolyl, benzoxazolyl and benzimidazolyl.

Notably, groups represented by A have, as a substituent, a reactive aliphatic hydroxyl group or reactive aliphatic mercapto group. Examples of the aliphatic hydroxyl group include $—(CH_2)_n—OH$, where n is an integer of 1 to 8.

As described above, $R^2$ in General Formula (1) represents a hydrogen atom, an alkyl group, an alkyloxy group or a halogen atom.

Examples of the alkyl group represented by $R^2$ include methyl, ethyl, propyl, iso-butyl, t-butyl and di-t-octyl.

Examples of the alkyloxy group represented by $R^2$ include methoxy, ethoxy, propyloxy, sec-butoxy and methoxyethyloxy.

Examples of the halogen atom represented by $R^2$ include bromine, chlorine, and iodine.

$X^1$ represents an electron attractive group selected from the above-listed groups.

Notably, as described above, A, $X^1$ or both of A and $X^1$ have, as a substituent, an aliphatic hydroxyl group such as $—(CH_2)_n—OH$ (where n is an integer of 1 to 8).

General Formula (2)

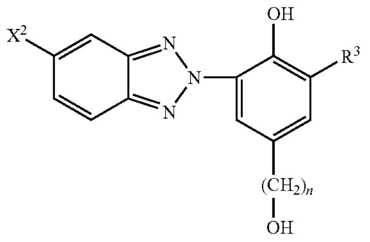

where $X^2$ represents a hydrogen atom, a halogen atom, $—NO_2$, —CN, $—CF_3$ or an alkyloxycarbonyl group; $R^3$ represents a hydrogen atom, a linear or branched alkyl group having 1 to 8 carbon atoms, —CHO or $—CH{=}N—R^4$ (where $R^4$ represents an alkyl group, an aryl group, an alkenyl group or an aralkyl group, each of which may have a substituent); n is an integer of 1 to 8; with the proviso that when $R^3$ is a linear or branched alkyl group having 1 to 8 carbon atoms, $X^2$ is not a hydrogen atom.

The alkyloxycarbonyl group represented by $X^2$ is preferably a linear or branched alkyloxycarbonyl group having 1 to 6 carbon atoms and is $R^1—O—$ of $R^1—OOC—$ in General Formula (1).

Examples of the linear or branched alkyl group having 1 to 8 carbon atoms represented by $R^3$ include methyl, ethyl, n-propyl, iso-propyl, n-butyl, iso-butyl, sec-butyl, t-butyl, n-pentyl, iso-pentyl, n-hexyl, n-octyl and di-t-octyl.

In the group $—CH{=}N—R^4$ represented by $R^3$ (where $R^4$ represents an alkyl group, an aryl group, an alkenyl group or an aralkyl group, each of which may have a substituent), the alkyl group, the aryl group, alkenyl group or aralkyl group represented by $R^4$ may be the same as those represented by $R^1$ in General Formula (1).

Next will be given non-limitative examples of specific compounds represented by General Formulas (1) and (2). Notably, in the examples, Me denotes a methyl group, Et denotes an ethyl group, Ph denotes a phenyl group, i-Pr denotes an isopropyl group, t-Bu denotes a tertiary butyl group, and t-Oct denotes a tertiary octyl group.

-continued
(A-1)
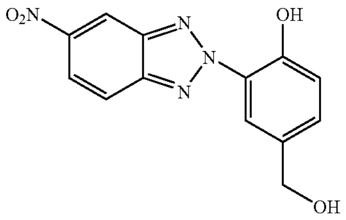
(A-2)
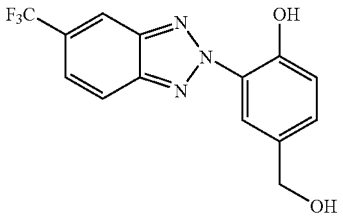
(A-3)
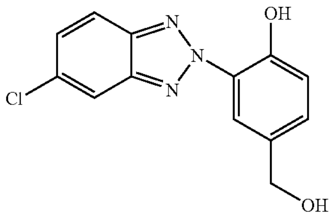
(A-4)
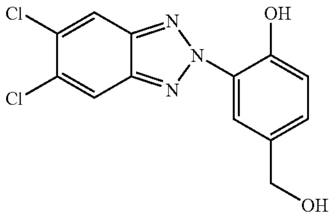
(A-5)
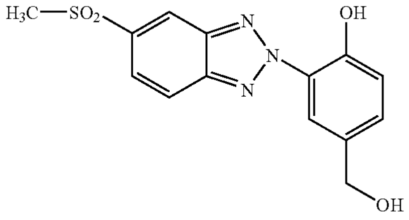
(A-6)
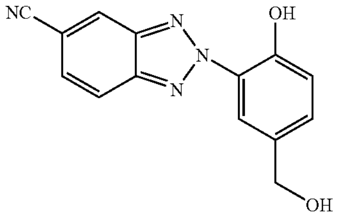
(A-7)
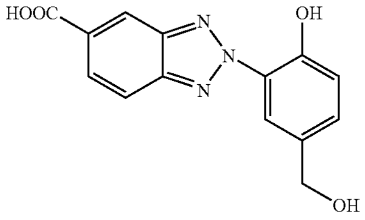
(A-8)
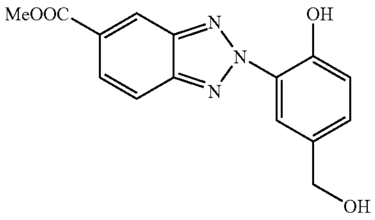
(A-9)
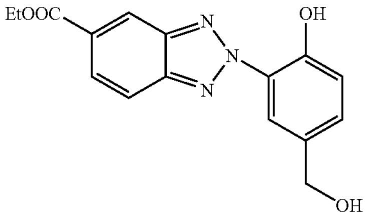
(A-10)
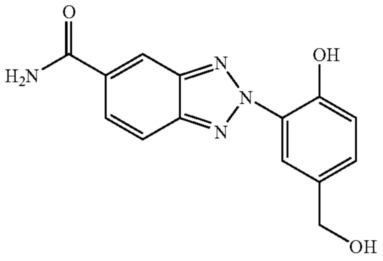
(A-11)
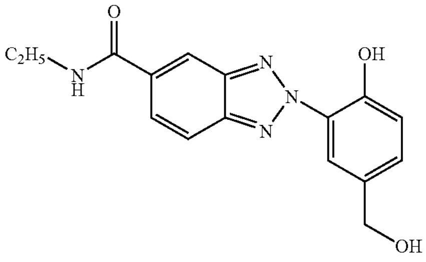
(A-12)
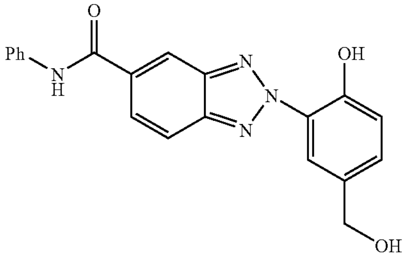
(A-13)
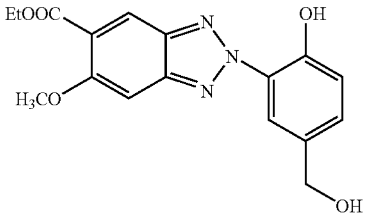

-continued
(A-14)
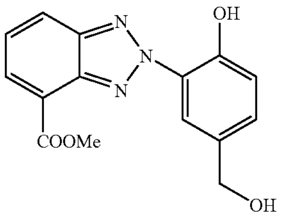
(A-15)
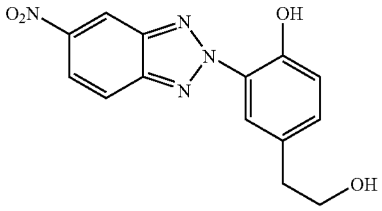
(A-16)
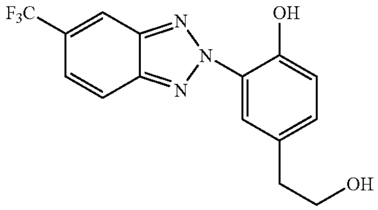
(A-17)
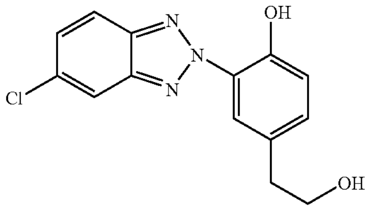
(A-18)
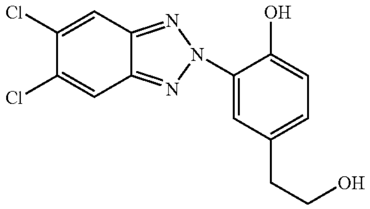
(A-19)
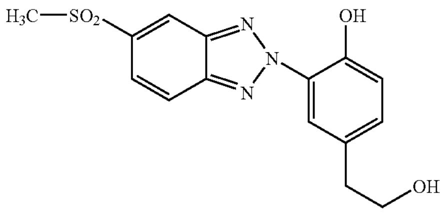
(A-20)
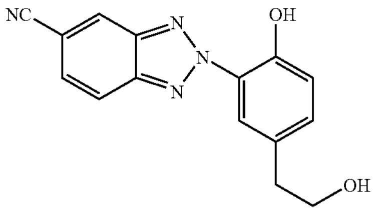
-continued
(A-21)
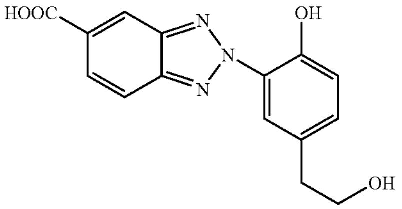
(A-22)
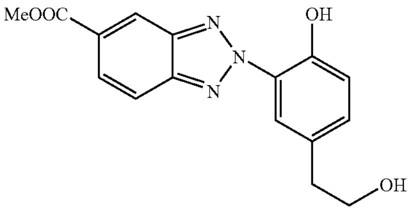
(A-23)
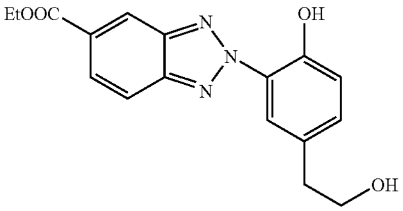
(A-24)
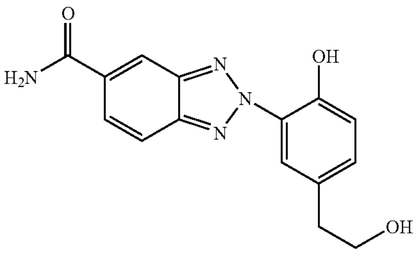
(A-25)
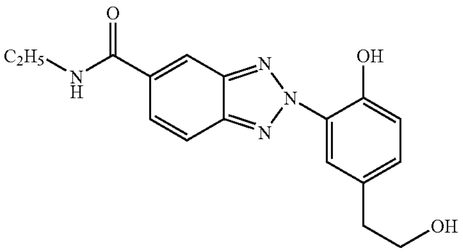
(A-26)
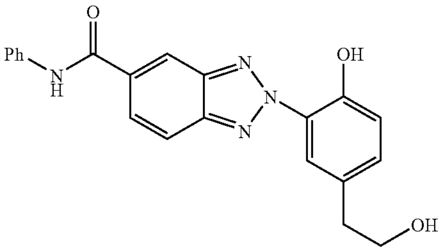
(A-27)
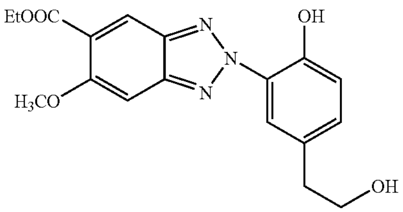

-continued
(A-28)
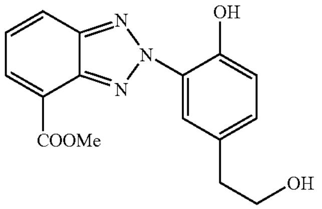
(B-1)
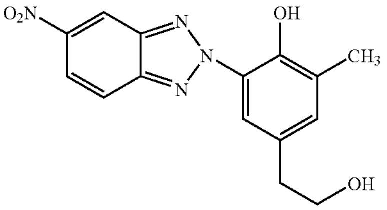
(B-2)
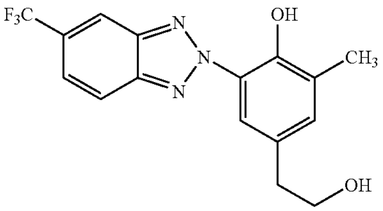
(B-3)
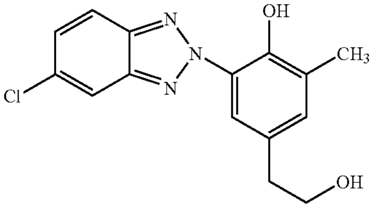
(B-4)
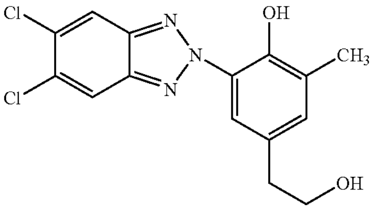
(B-5)
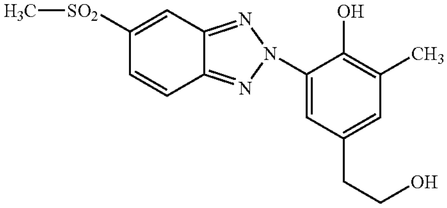
(B-6)
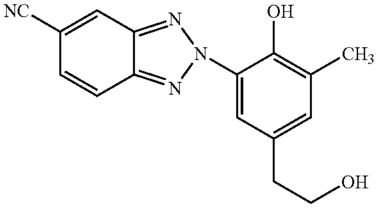
-continued
(B-7)
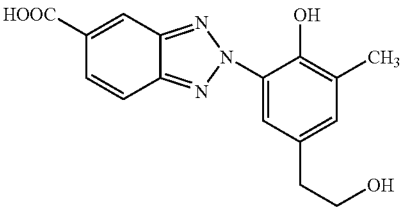
(B-8)
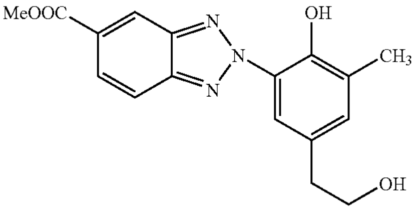
(B-9)
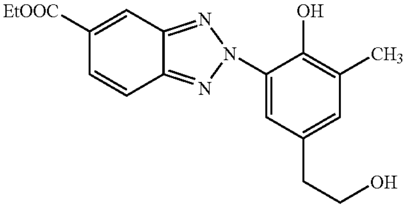
(B-10)
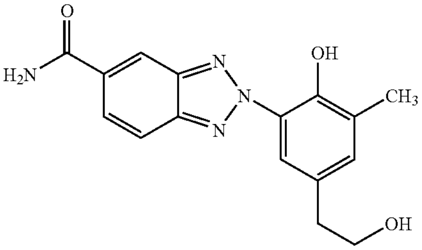
(B-11)
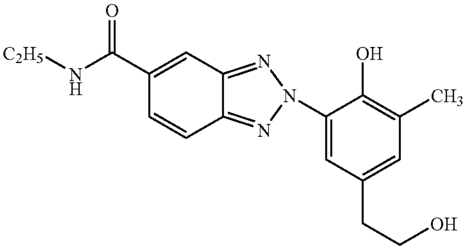
(B-12)
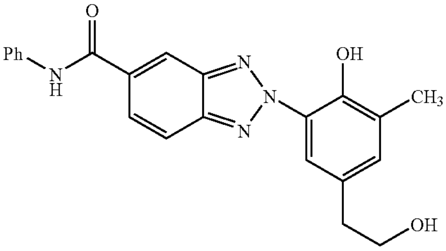
(B-13)
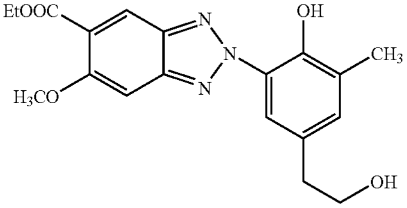

-continued
(B-14)
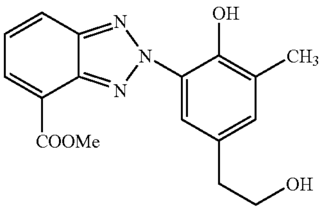
(B-15)
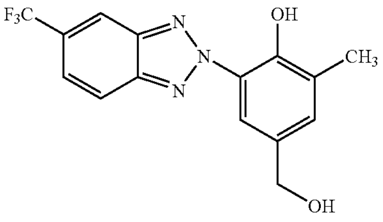
(C-1)
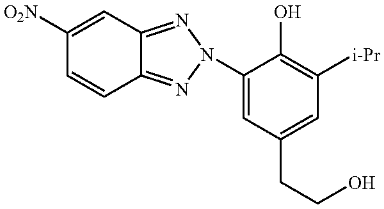
(C-2)
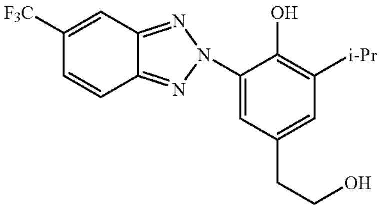
(C-3)
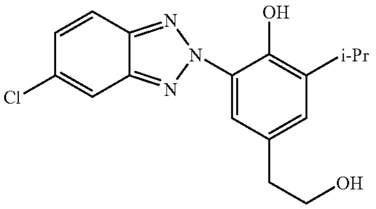
(C-4)
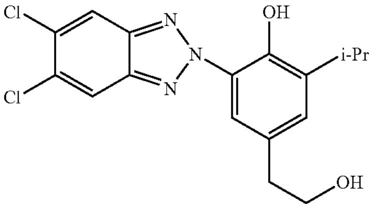
(C-5)
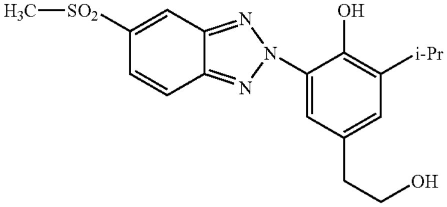
-continued
(C-6)
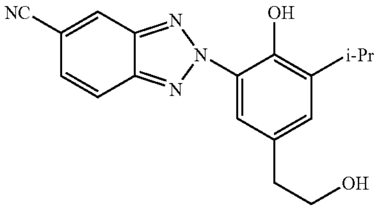
(C-7)
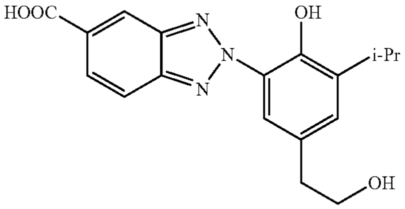
(C-8)
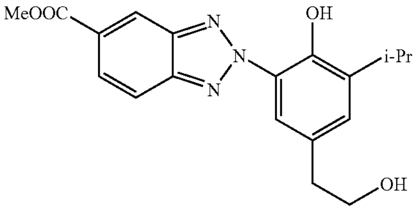
(C-9)
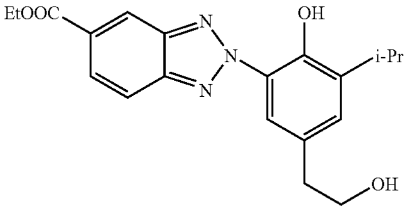
(C-10)
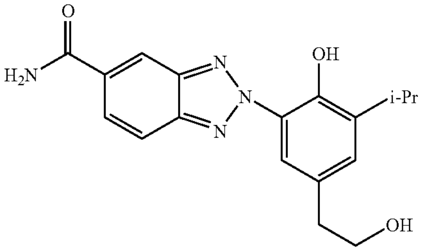
(C-11)
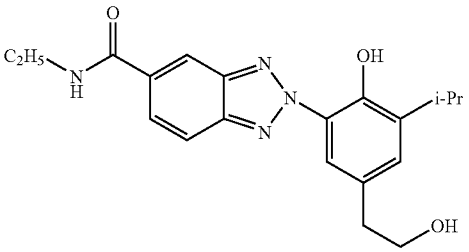
(C-12)
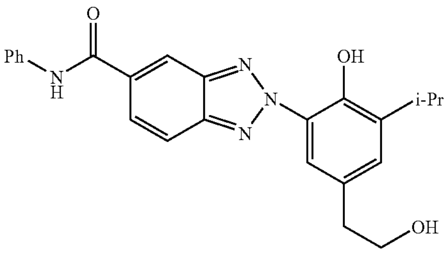

-continued
(C-13)
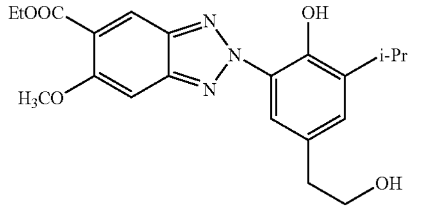
(C-14)
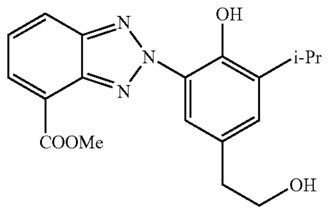
(D-1)
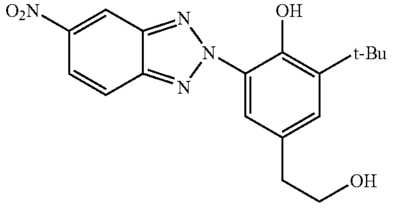
(D-2)
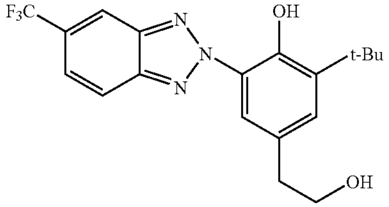
(D-3)
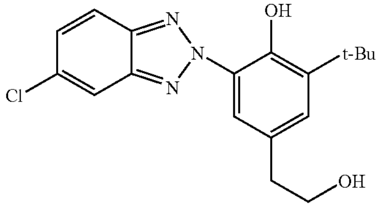
(D-4)
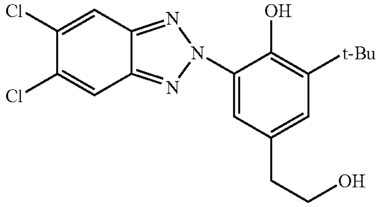
(D-5)
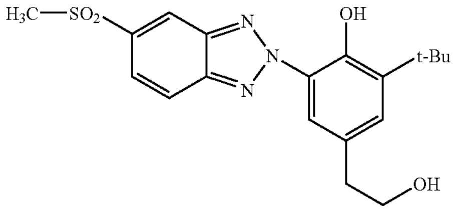
-continued
(D-6)
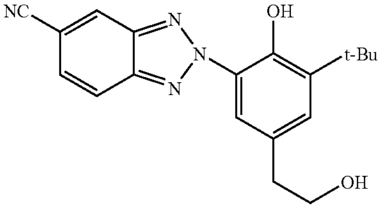
(D-7)
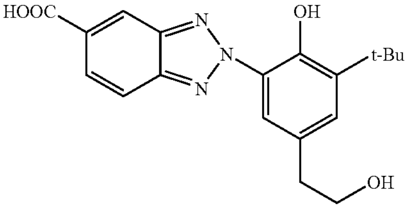
(D-8)
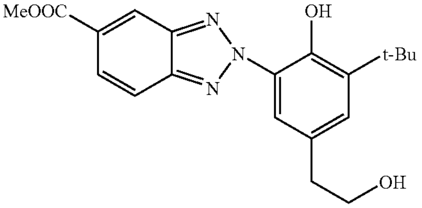
(D-9)
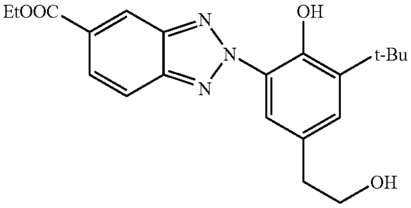
(D-10)
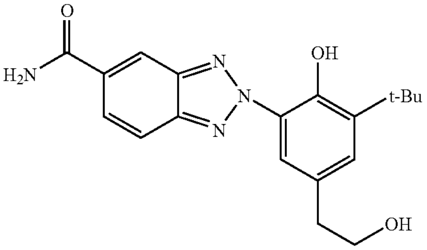
(D-11)
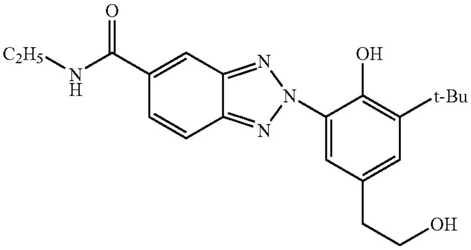
(D-12)
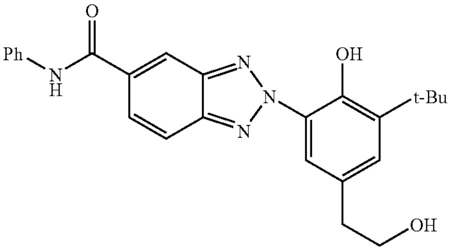

-continued
(D-13)
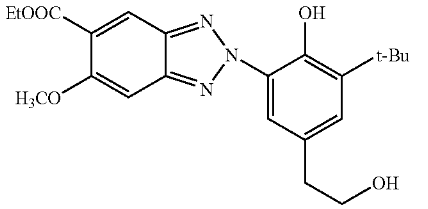
(D-14)
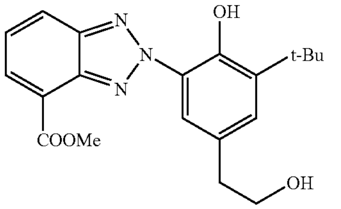
(E-1)
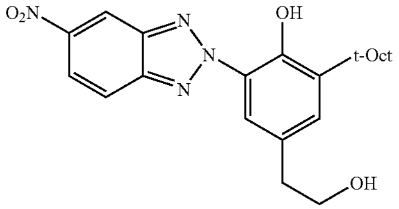
(E-2)
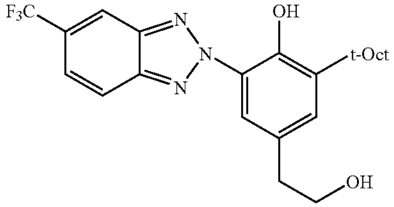
(E-3)
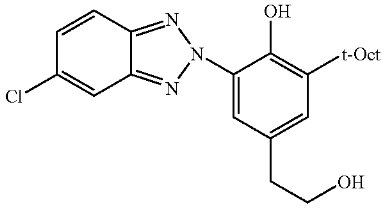
(E-4)
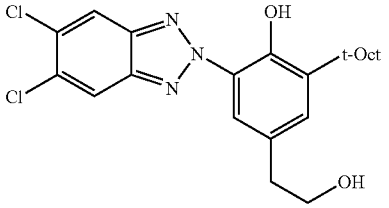
(E-5)
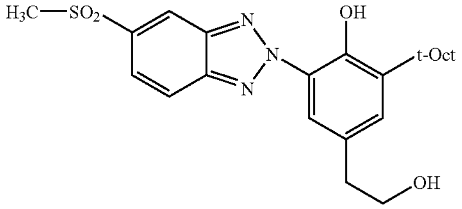
-continued
(E-6)
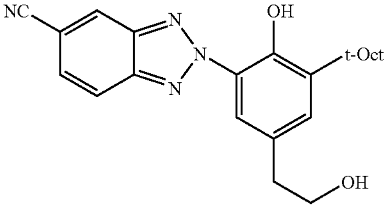
(E-7)
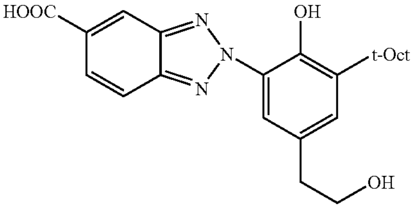
(E-8)
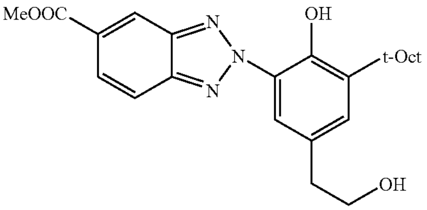
(E-9)
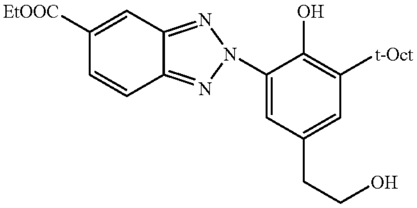
(E-10)
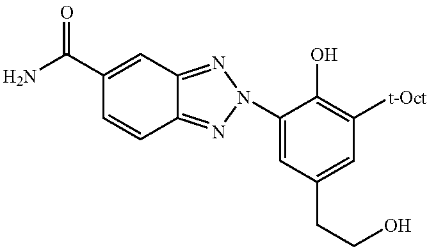
(E-11)
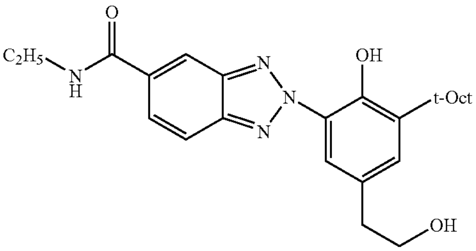
(E-12)
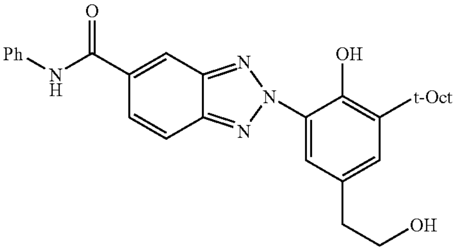

-continued
(E-13)
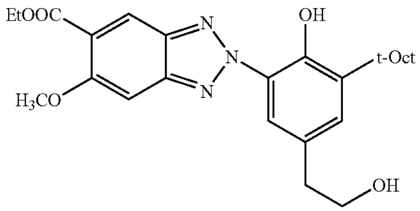
(E-14)
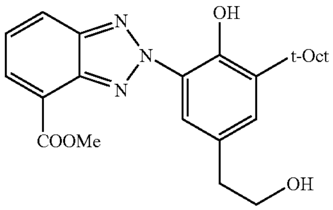
(F-1)
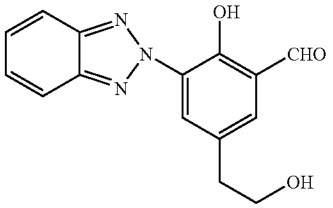
(F-2)
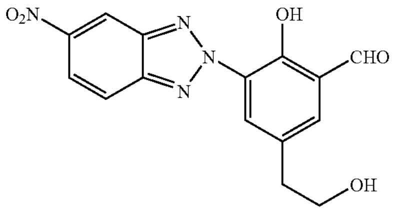
(F-3)
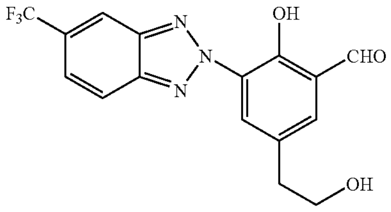
(F-4)
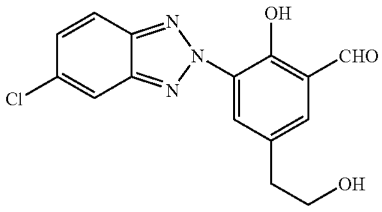
(F-5)
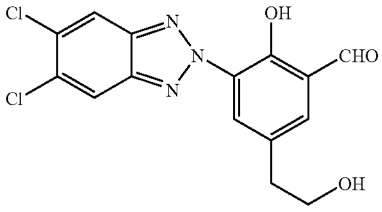
-continued
(F-6)
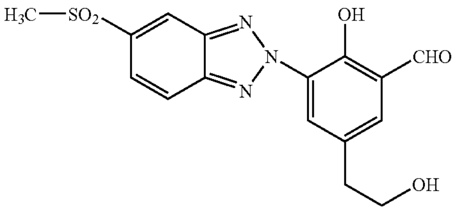
(F-7)
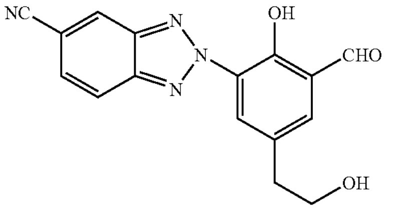
(F-8)
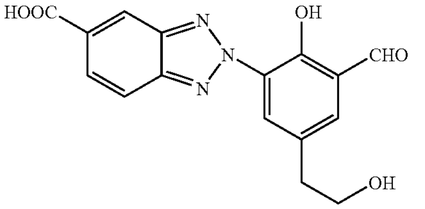
(F-9)
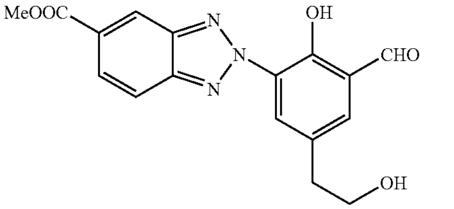
(F-10)
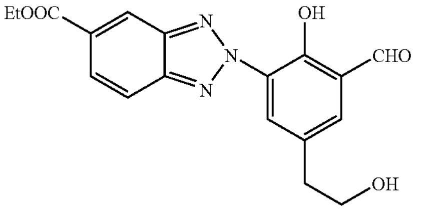
(F-11)
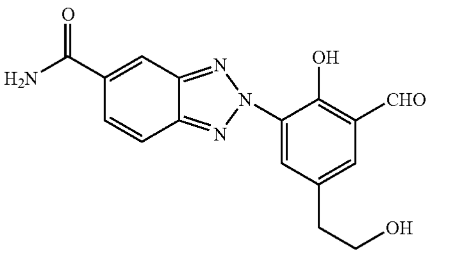
(F-12)
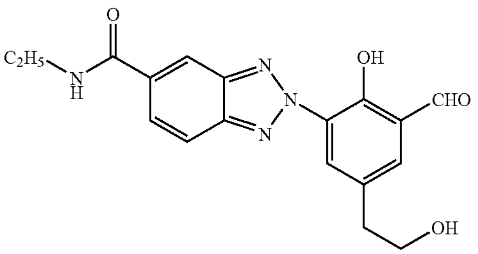

(F-13)
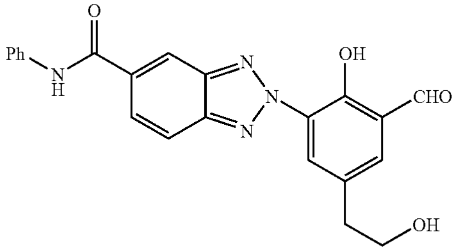
(F-14)
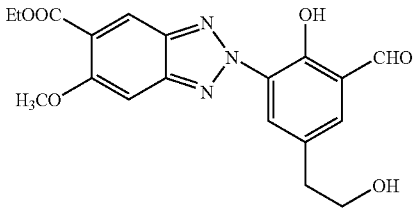
(F-15)
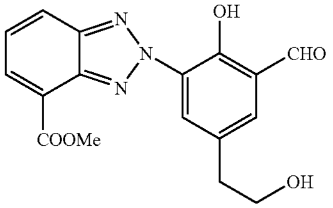
(G-1)
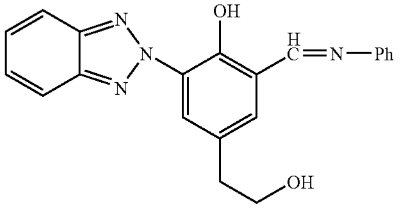
(G-2)
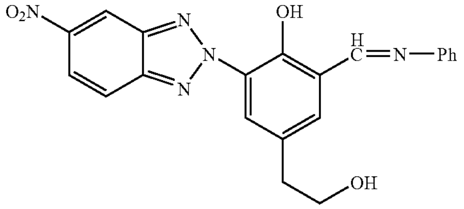
(G-3)
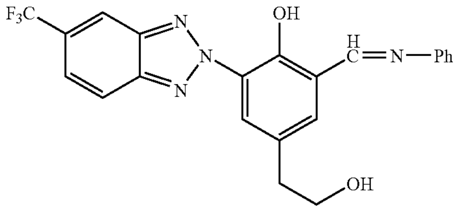
(G-4)
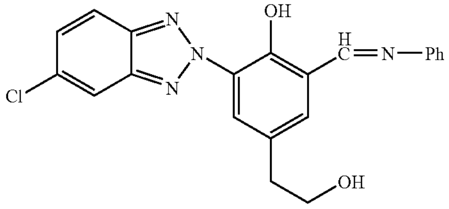
(G-5)
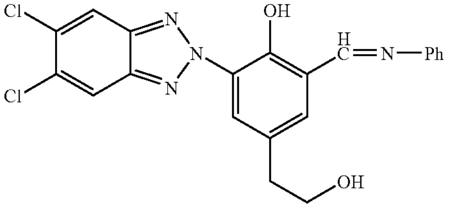
(G-6)
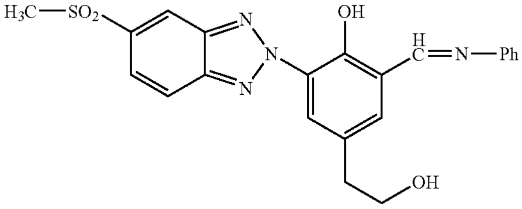
(G-7)
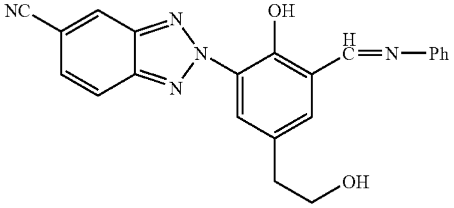
(G-8)
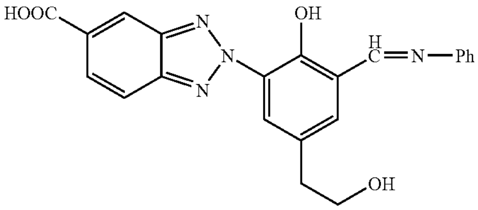
(G-9)
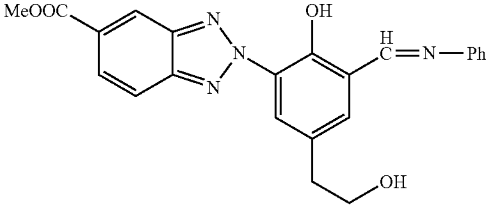
(G-10)
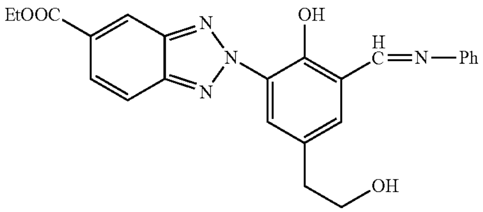
(G-11)
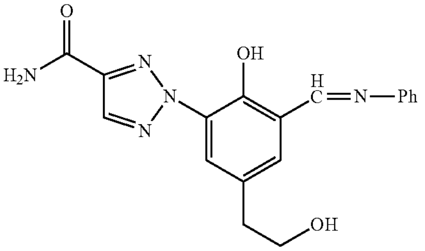

-continued
(G-12)
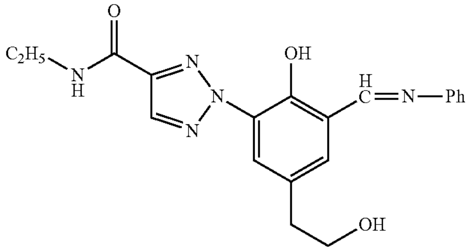
(G-13)
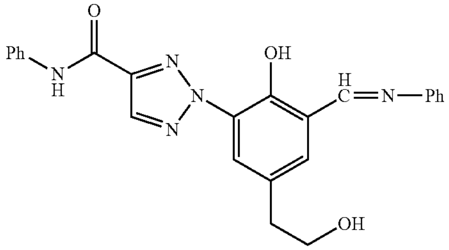
(G-14)
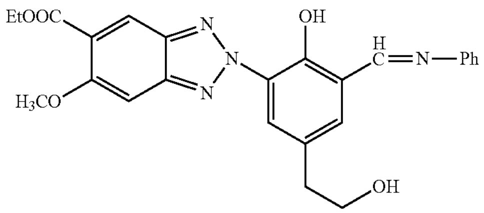
(G-15)
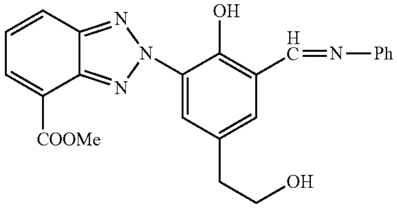
(H-1)
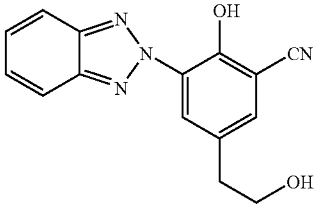
(H-2)
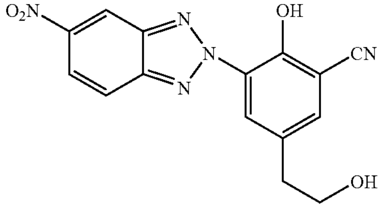
(H-3)
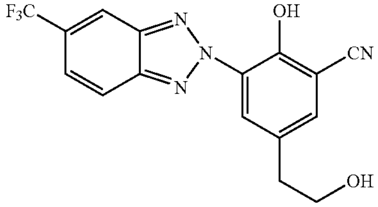
-continued
(H-4)
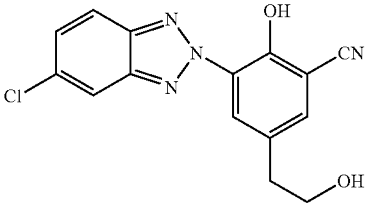
(H-5)
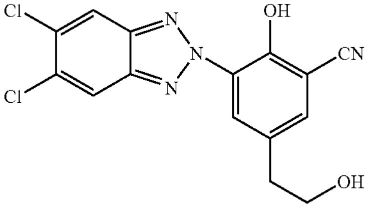
(H-6)
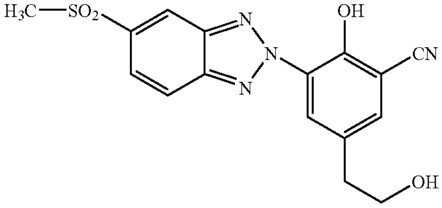
(H-7)
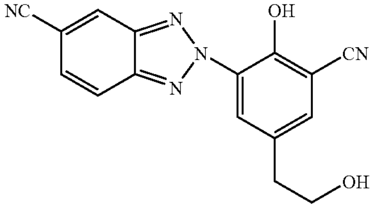
(H-8)
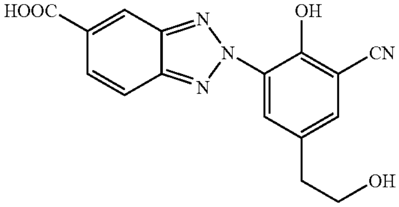
(H-9)
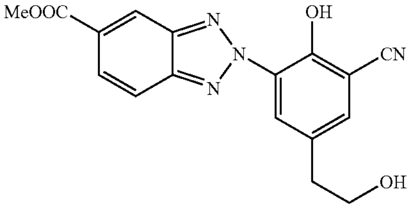
(H-10)
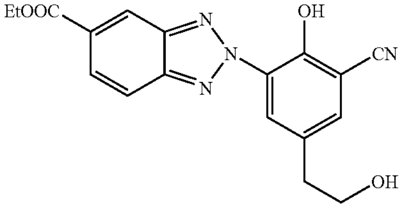

-continued
(H-11)
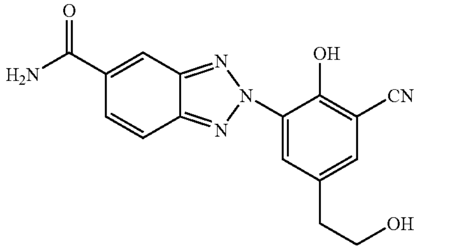
(H-12)
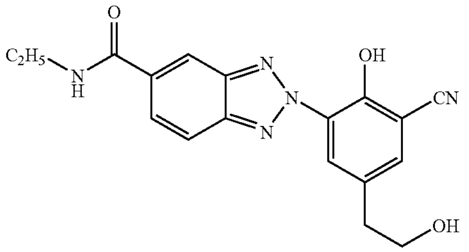
(H-13)
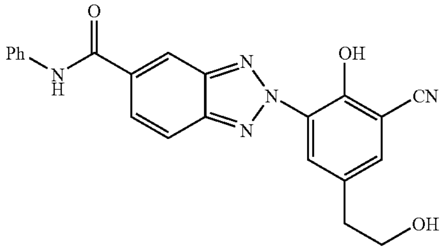
(H-14)
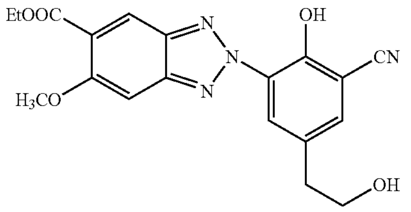
(H-15)
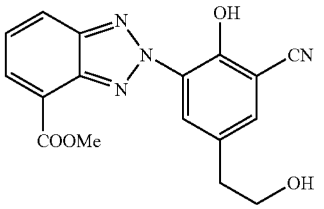
(I-1)
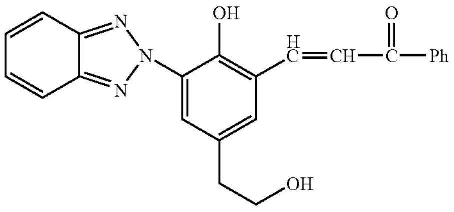
(I-2)
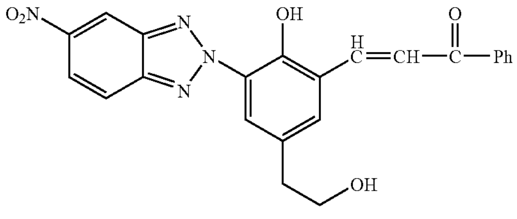
-continued
(I-3)
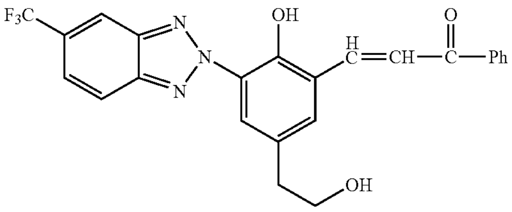
(I-4)
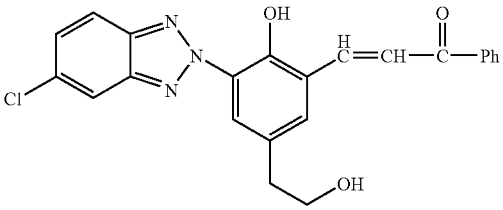
(I-5)
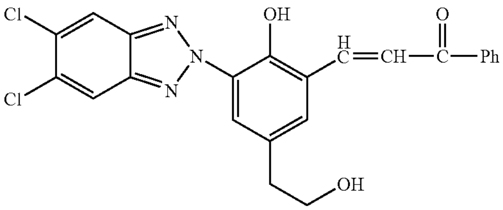
(I-6)
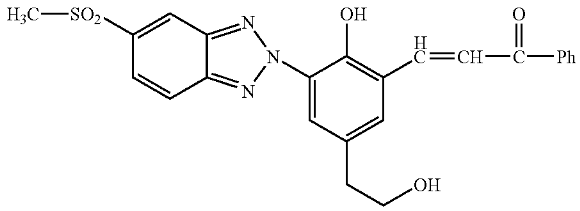
(I-7)
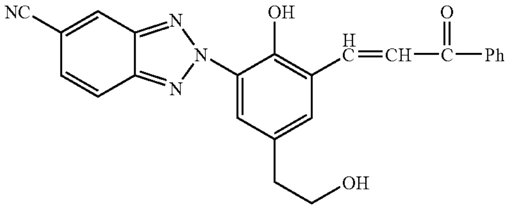
(I-8)
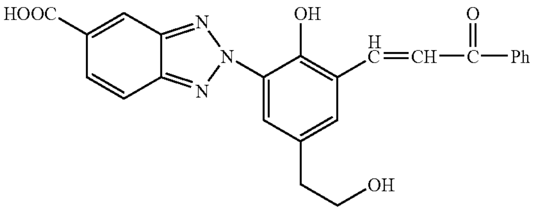
(I-9)
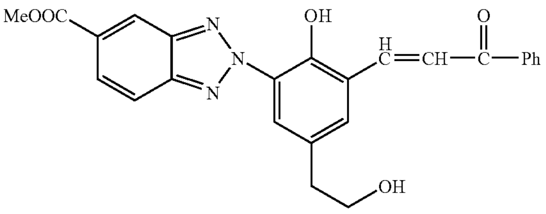

-continued
(I-10)
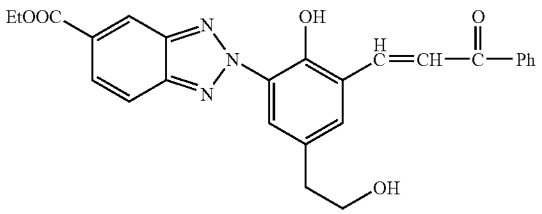
(I-11)
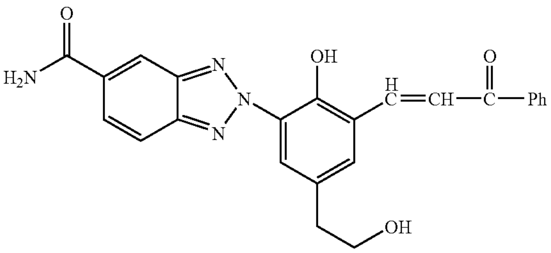
(I-12)
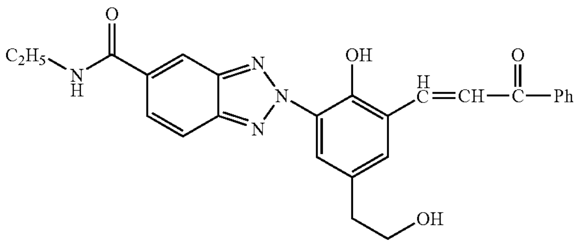
(I-13)
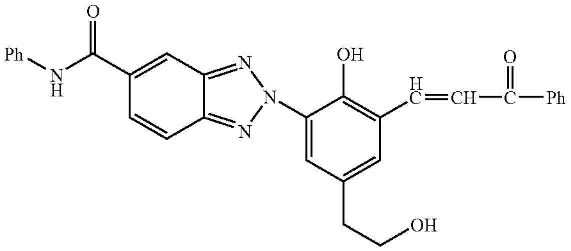
(I-14)
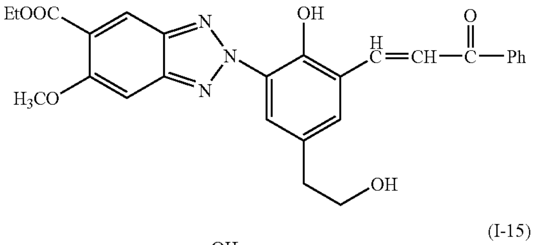
(I-15)
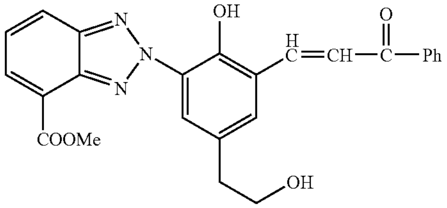
-continued
(J-1)
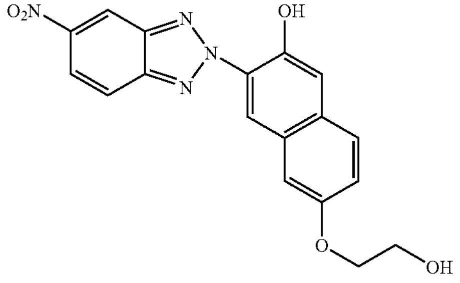
(J-2)
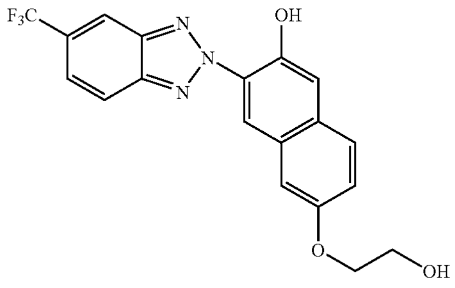
(J-3)
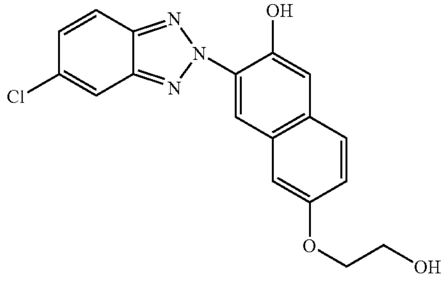
(J-4)
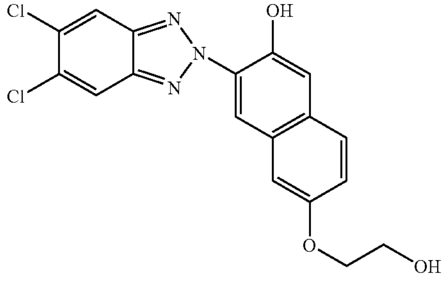
(J-5)
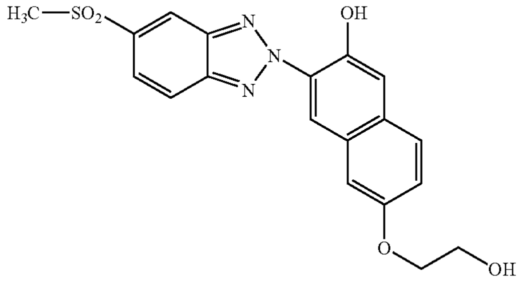

-continued
(J-6)
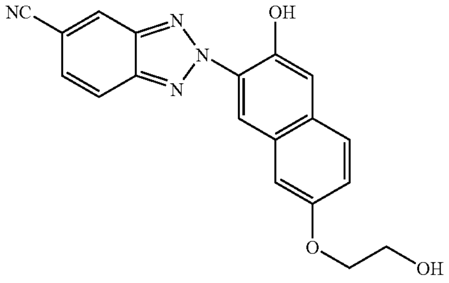
(J-7)
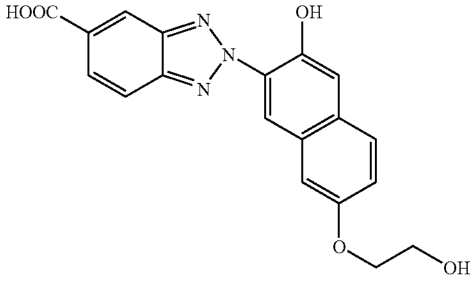
(J-8)
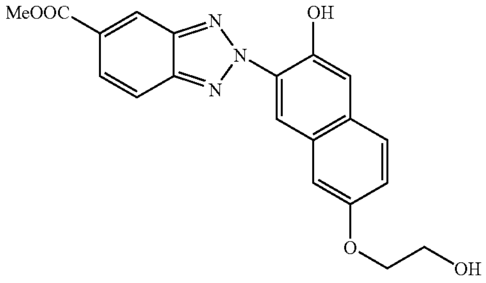
(J-9)
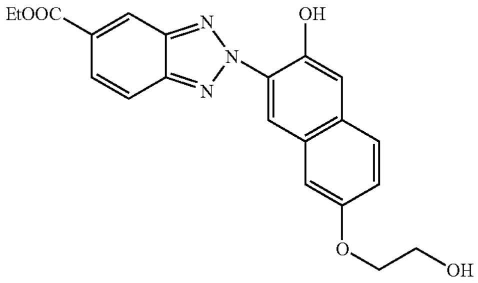
(J-10)
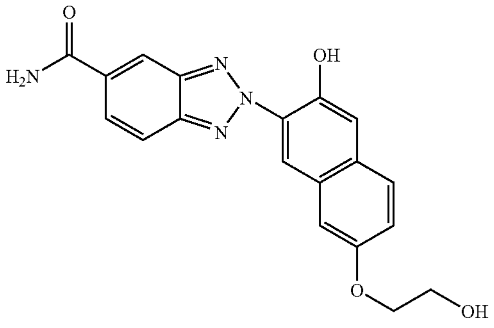
-continued
(J-11)
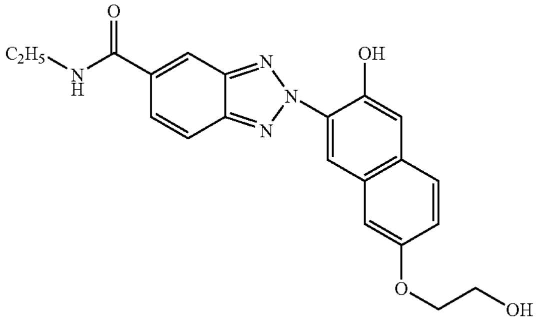
(J-12)
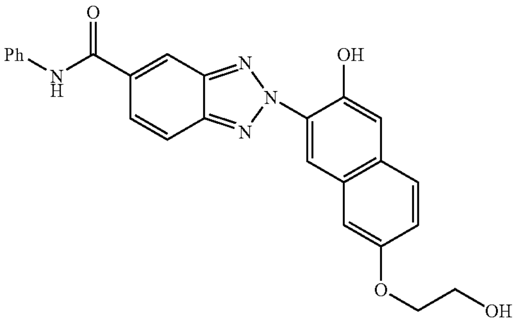
(J-13)
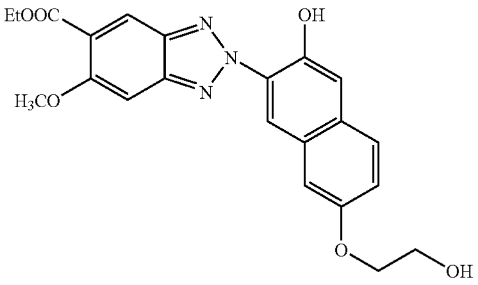
(J-14)
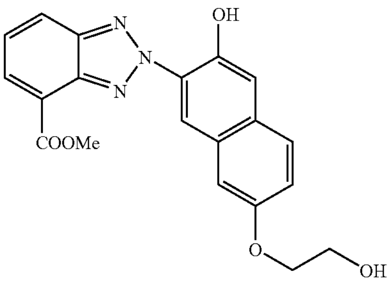
(J-15)
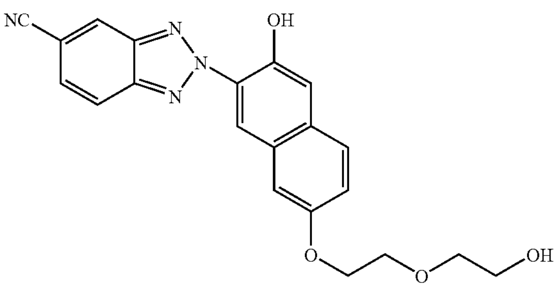

-continued
(J-16)
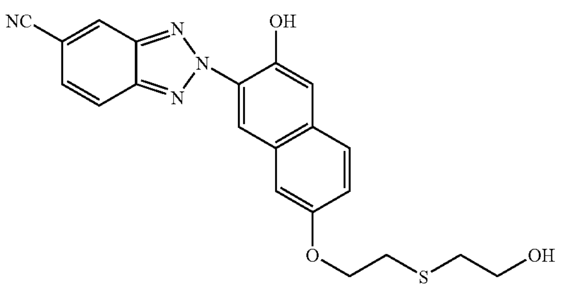
(J-17)
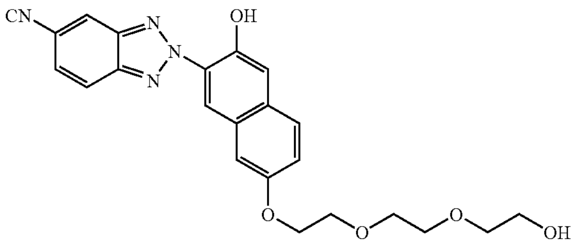
(K-1)
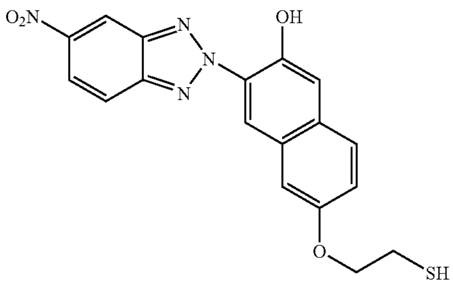
(K-2)
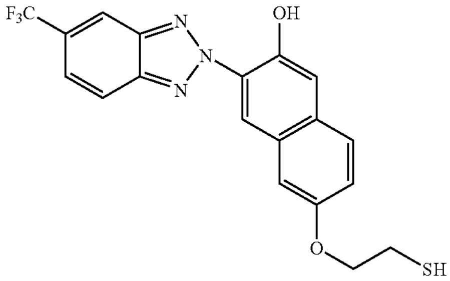
(K-3)
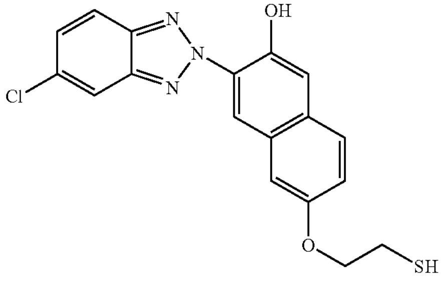
-continued
(K-4)
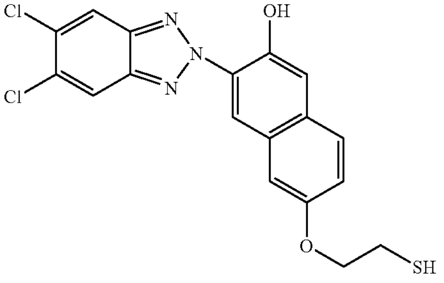
(K-5)
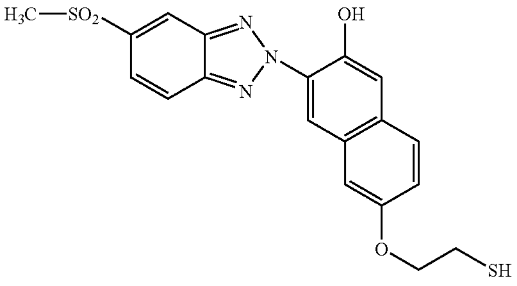
(K-6)
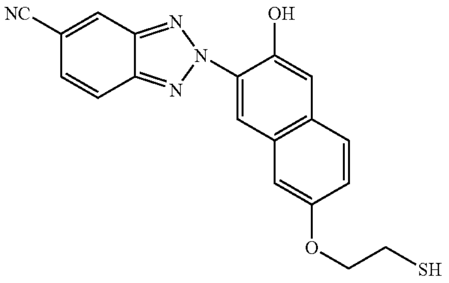
(K-7)
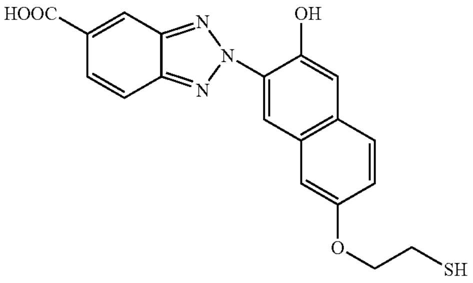
(K-8)
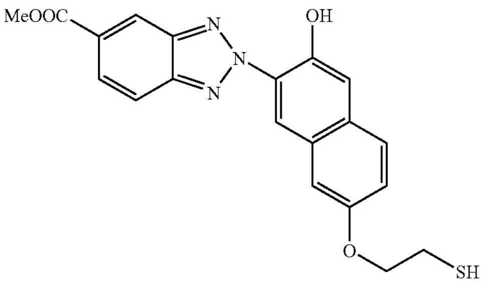

-continued
(K-9)
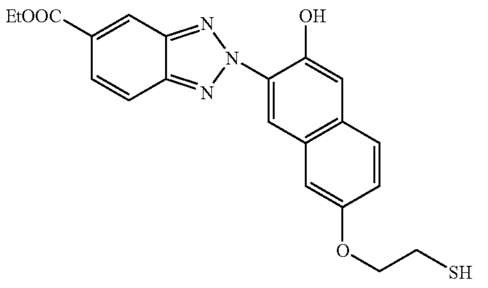
(K-10)
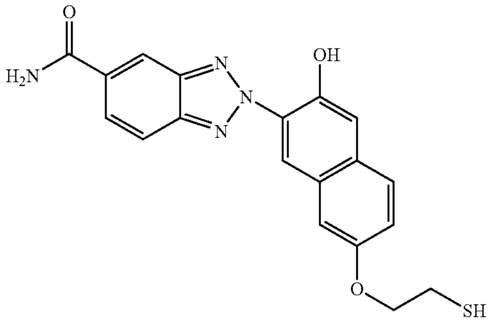
(K-11)
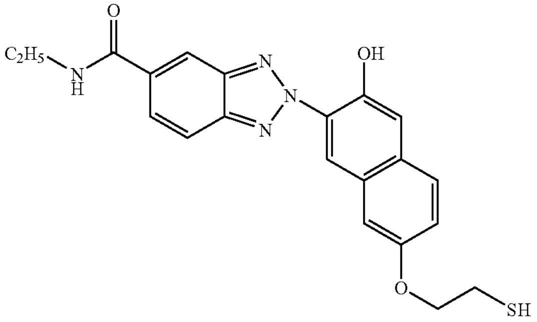
(K-12)
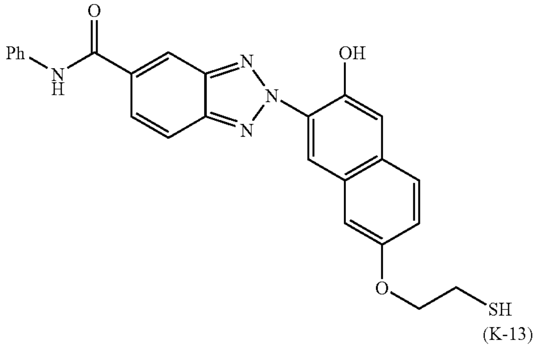
(K-13)
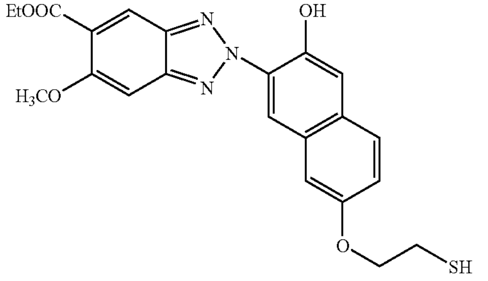
-continued
(K-14)
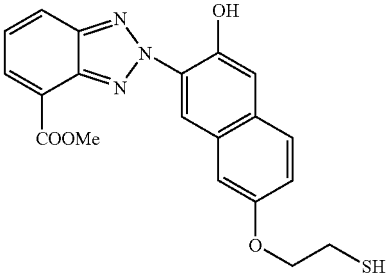
(K-15)
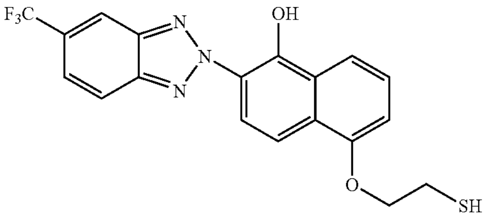
(L-1)
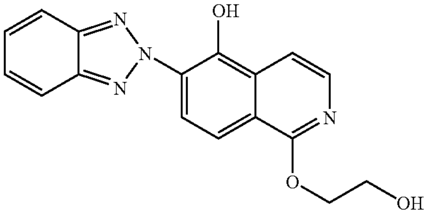
(L-2)
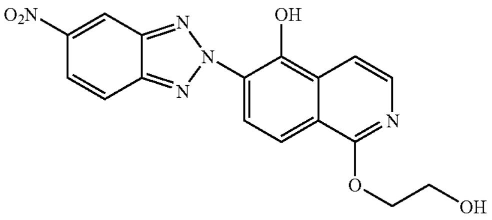
(L-3)
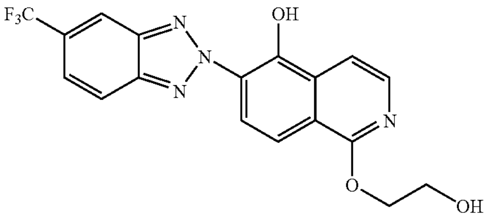
(L-4)
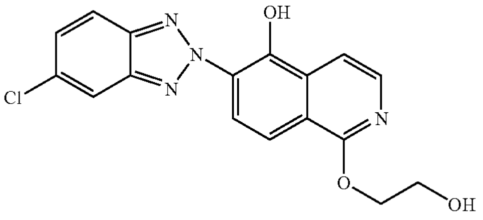

-continued
(L-5)
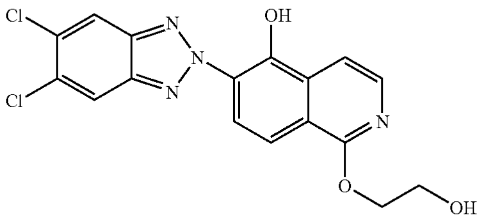
(L-6)
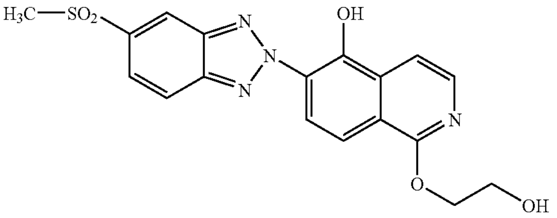
(L-7)
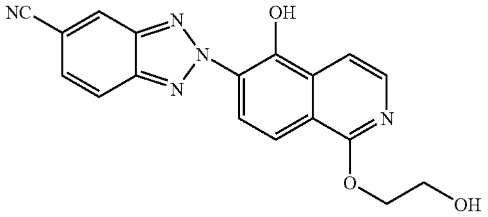
(L-8)
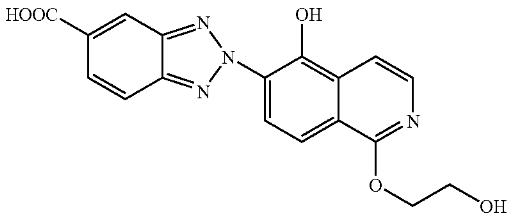
(L-9)
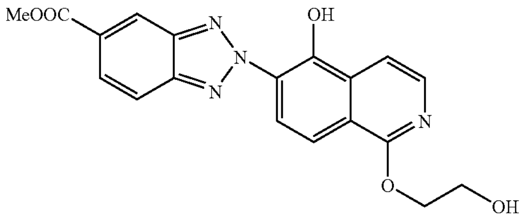
(L-10)
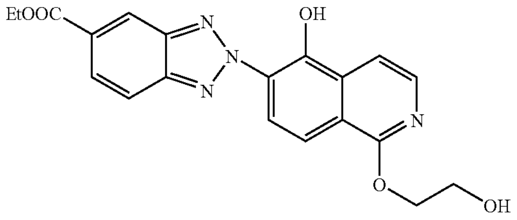
-continued
(L-11)
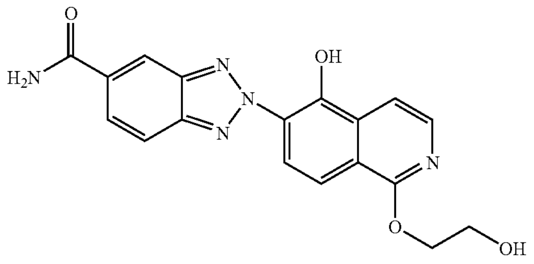
(L-12)
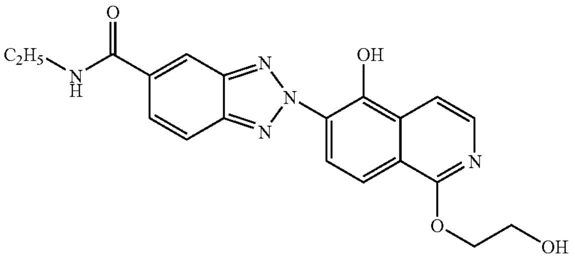
(L-13)
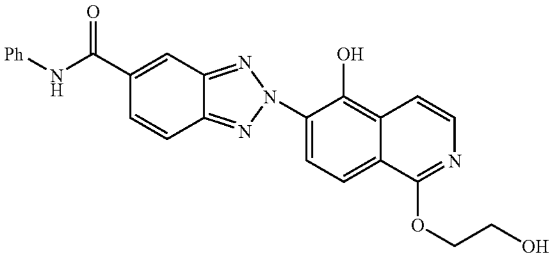
(L-14)
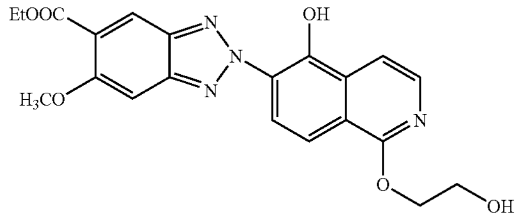
(L-15)
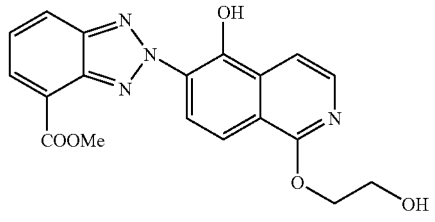
(M-1)
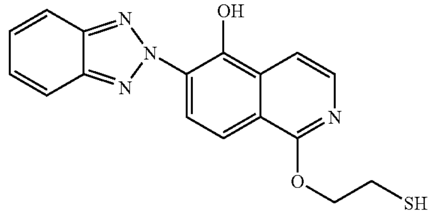

-continued
(M-2)
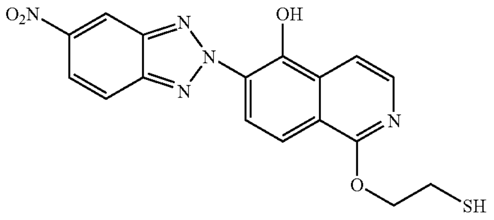
(M-3)
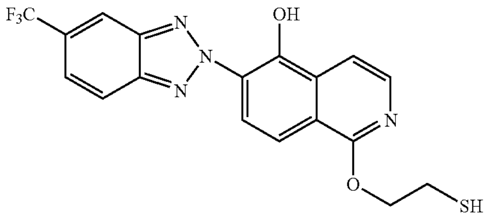
(M-4)
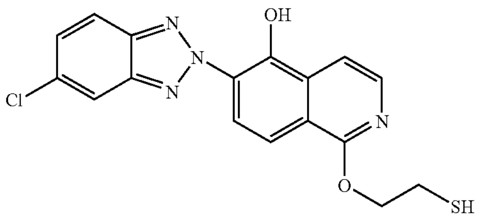
(M-5)
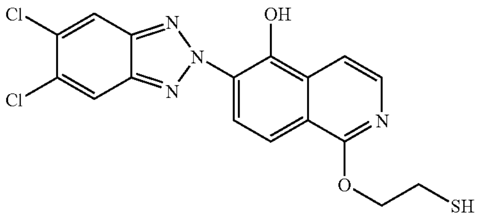
(M-6)
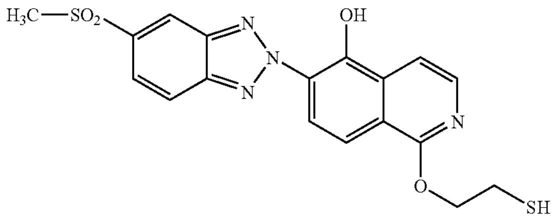
(M-7)
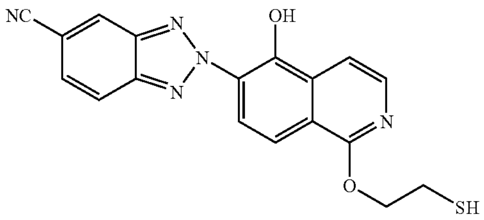
-continued
(M-8)
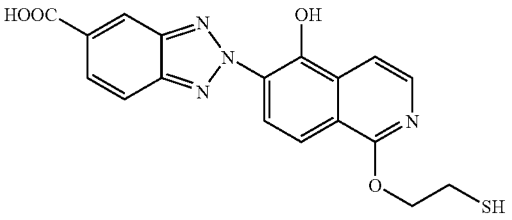
(M-9)
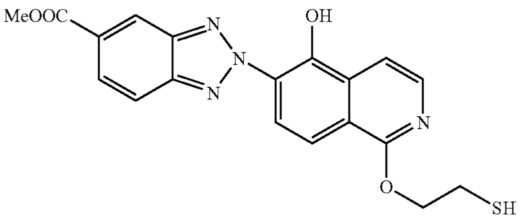
(M-10)
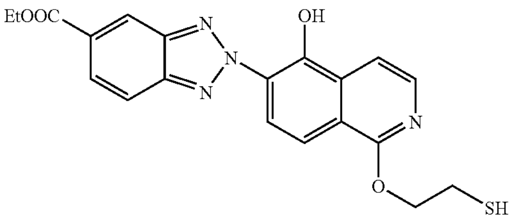
(M-11)
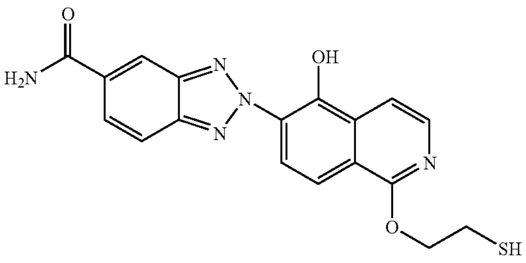
(M-12)
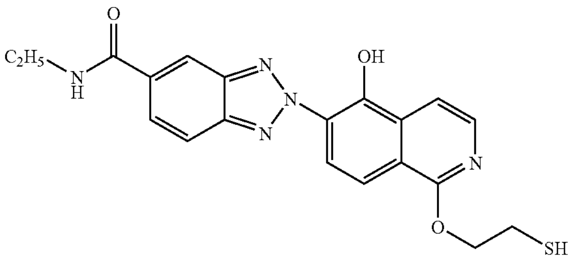
(M-13)
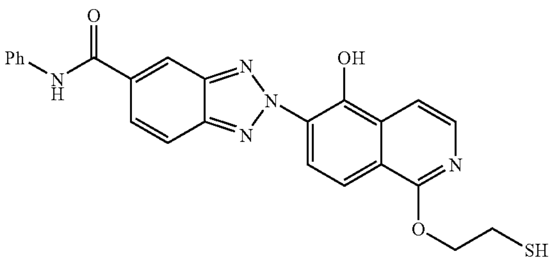

-continued (M-14)

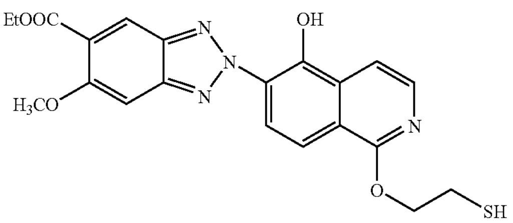

(M-15)

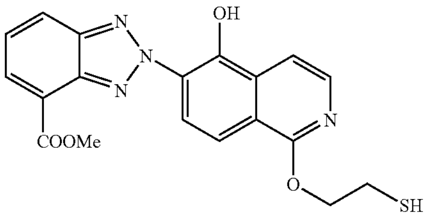

In a second embodiment, the heat resistance improver of the present invention preferably contains, as a heat resistance improving component, a compound represented by the following General Formula (5) or (6).

General Formula (5)

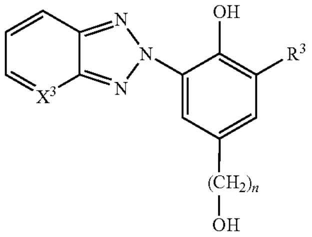

where $X^3$ represents an electronegative atom such as a nitrogen atom and an oxygen atom; $R^3$ represents a hydrogen atom, a linear or branched alkyl group having 1 to 8 carbon atoms, —CHO or —CH═N—$R^4$, where $R^4$ represents an alkyl group, an aryl group, an alkenyl group or an aralkyl group each of which may have a substituent; and n is an integer of 1 to 8.

General Formula (6)

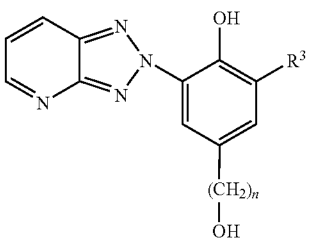

where $R^3$ and n have the same meanings as defined in General Formula (5).

Next will be given non-limitative examples of specific compounds represented by General Formulas (5) and (6).

(N-1)

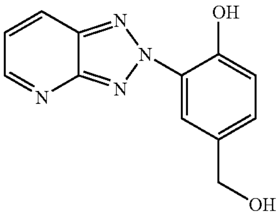

(N-2)

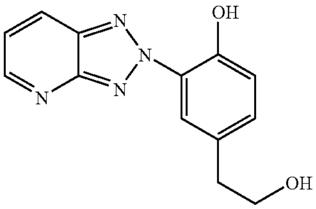

(N-3)

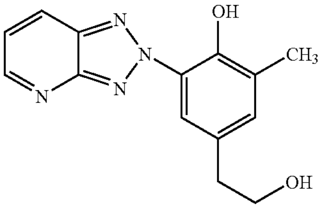

(N-4)

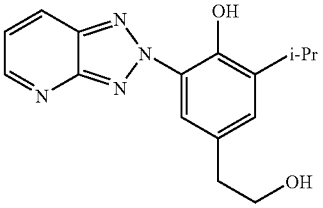

(N-5)

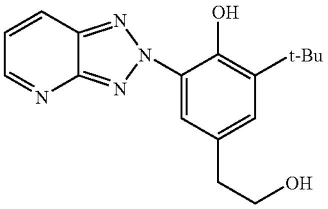

(N-6)

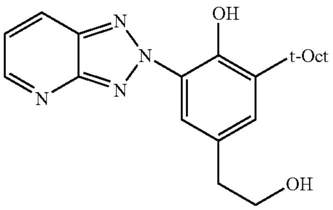

(N-7)

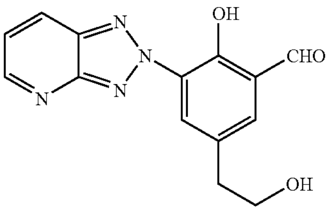

-continued (N-8)

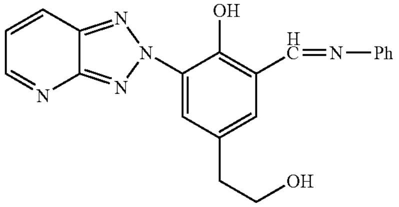

(N-9)

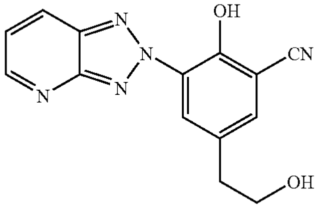

(N-10)

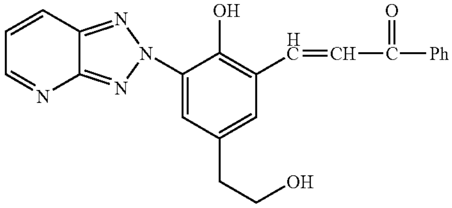

In a first embodiment, the heat resistance improver of the present invention may contain a heat resistance improving polymer as a heat resistance improving component.

The heat resistance improving polymer preferably is a reactive hydroxyl group-containing polymer produced through polymerization of at least a compound represented by the following General Formula (3) and hydroxyalkyl (meth)acrylate.

General Formula (3)

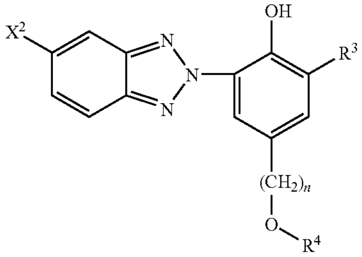

where $X^2$ represents a hydrogen atom, a halogen atom, —$NO_2$, —CN, —$CF_3$ or an alkyloxycarbonyl group; $R^3$ represents a hydrogen atom, a linear or branched alkyl group having 1 to 8 carbon atoms, —CHO or —CH═N—$R^4$, where $R^4$ represents an alkyl group, an aryl group, an alkenyl group or an aralkyl group each of which may have a substituent; n is an integer of 1 to 8; with the proviso that when $R^3$ is a linear or branched alkyl group having 1 to 8 carbon atoms, $X^2$ is not a hydrogen atom; and $R^4$ represents a polymerizable unsaturated hydrocarbon group.

Examples of the polymerizable unsaturated hydrocarbon group represented by $R^4$ in General Formula (3) include styryl, α-methylstyryl, α-methoxystyryl, m-bromostyryl, m-chlorostyryl, o-bromostyryl, o-chlorostyryl, p-bromostyryl, p-chlorostyryl, p-methylstyryl, p-methoxystyryl, isobutenyl, 3-methyl-1-butenyl, vinyl acetate group, acryloyl and mathacryloyl. Of these, acryloyl and mathacryloyl are particularly preferred, since these can be readily synthesized by reacting carboxylic acid chloride with a reactive aliphatic hydroxyl group.

The compound represented by General Formula (3) is preferably a compound represented by the following General Formula (4).

General Formula (4)

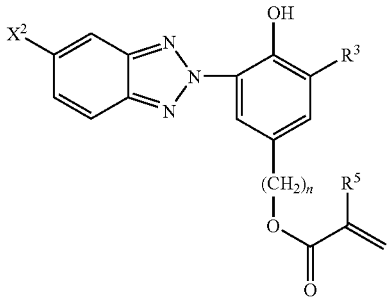

where $X^2$, n and $R^3$ have the same meanings as defined in General Formula (3); and $R^5$ represents a hydrogen atom or a methyl group.

The monomer represented by General Formula (3) or (4) is the same as the compound represented by General Formula (2), except that the hydroxyl group of the aliphatic hydroxyl group is substituted with the reactive group shown in General Formula (3) or (4), and may be the above-listed specific compounds.

In a second embodiment, the heat resistance improver of the present invention contains, as a heat resistance improving component, a heat resistance improving polymer produced through polymerization of a compound represented by the following General Formula (7) and hydroxyalkyl(meth)acrylate:

General Formula (7)

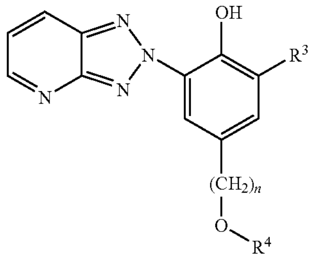

$R^3$ represents a hydrogen atom, a linear or branched alkyl group having 1 to 8 carbon atoms, —CHO or —CH═N—$R^4$, where $R^4$ represents an alkyl group, an aryl group, an alkenyl group or an aralkyl group each of which may have a substituent; n is an integer of 1 to 8; and $R^4$ represents a polymerizable unsaturated hydrocarbon group.

Compounds represented by General Formula (7) are preferably those represented by General Formula (8):

General Formula (8)

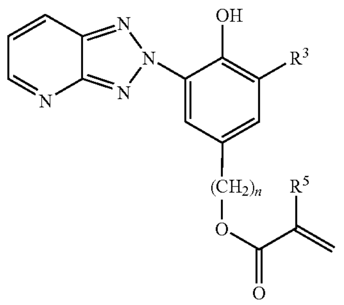

where $R^3$ and n have the same meanings as defined in General Formula (7); and $R^5$ represents a hydrogen atom or a methyl group.

The monomer represented by General Formula (7) or (8) is the same as the compound represented by General Formula (5) or (6), except that the hydroxyl group of the aliphatic hydroxyl group of the compound is substituted with the reactive group shown in General Formula (7) or (8), and may be the above-listed specific compounds.

The type of the hydroxyalkyl(meth)acrylate is not particularly limited and can be appropriately selected depending on the purpose. Examples thereof include hydroxyalkyl(C1 to C4) (meth)acrylates such as 2-hydroxyethyl(meth)acrylate, 3-hydroxypropyl (meth)acrylate, 2-hydroxypropyl(meth) acrylate and 4-hydroxybutyl (meth)acrylate; polyethylene glycol derivatives of (meth)acrylic acid; caprolactone adducts of (meth)acrylic acid; vinyl ether derivatives such as hydroxymethyl vinyl ether, hydroxyethyl vinyl ether and hydroxypropyl vinyl ether; and vinyl ketone derivatives such as hydroxymethyl vinyl ketone, hydroxyethyl vinyl ketone and hydroxypropyl vinyl ketone. These may be used alone or in combination. Among them, particularly preferred are p-hydroxystyren, 2-hydroxyethyl(meth)acrylate, 3-hydroxypropyl (meth)acrylate and polyethylene glycol derivatives of (meth)acrylic acid, which are easily available in general.

The polymerization initiator used in polymerization reaction performed for producing a heat resistance improving polymer is not particularly limited and may be those known in the art. The type of the polymerization reaction is also not particularly limited, and radical polymerization, anion polymerization and cation polymerization can be used, with radical polymerization being preferred. If necessary, the reaction system for the polymerization may be heated.

Examples of the polymerization initiator used for radical polymerization include peroxides such as hydrogen peroxide, cumene hydroperoxide, t-butyl hydroperoxide, dicumyl peroxide, di-t-butyl peroxide, benzoyl peroxide and lauroyl peroxide; persulfates such as potassium persulfate and ammonium persulfate; azo compounds such as 2,2'-azobisisobutylonitrile, 2,2'-azobis(2,4-dimethylvaleronitrile), 2,2'-azobis(4-methoxy-2,4-dimethylvaleronitrile), 2,2'-azobis(2-methylpropionamidine)dihydrochloride and 4,4'-azobis(4-cyanovaleric acid); and redox initiators such as a combination of hydrogen peroxide and a ferrous salt, a combination of a persulfate and sodium hydrogen sulfite, a combination of cumene hydroxyperoxide and a ferrous salt, a combination of benzoyl peroxide and diethylaniline, a combination of a peroxide and a metal alkyl, and a combination of oxygen and an organic metal alkyl.

In addition to the above, any polymerization initiators which generate active radicals through application of heat or light can be used for the radical polymerization, and can be appropriately selected depending on the purpose. Examples thereof include peroxides such as benzoyl peroxide and dibutyl peroxide; and azo polymerization initiators such as azobisisobutylonitrile.

These may be used alone or in combination.

The amount of the polymerization initiator used is not particularly limited, and can be appropriately determined depending on the various reaction conditions. Preferably, it is 0.1 mol % to 5 mol % with respect to the amount of the monomer used. Also, in order to control the polymerization degree of the formed copolymer, a chain transfer agent (e.g., dodecyl mercaptan) and/or a polymerization inhibitor (e.g., hydroquinone) may be added to the reaction system.

The polymerization reaction is performed at a temperature required for proceeding of polymerization reaction, preferably at room temperature to the boiling point of a solvent used. The polymerization reaction time is preferably 1 hour to 50 hours, more preferably 2 hours to 24 hours.

The solvent is not particularly limited, so long as it does not adversely affect the target reaction, and can be appropriately selected depending on the purpose. Examples thereof include aliphatic hydrocarbons such as petroleum ethers, hexane and heptane; aromatic hydrocarbons such as benzene, toluene and xylene; ketones such as acetone, methyl ethyl ketone and cyclohexanone; ethers such as diethyl ether, diisopropyl ether, dibutyl ether, tetrahydrofuran (THF) and dioxane; esters such as ethyl acetate, propyl acetate and butyl acetate; and amides such as N,N-dimethylformamide and N,N-dimethylacetamide. Of these, ethers, esters, ketones and other solvents, which are unreactive to an isocyanate compound, are particularly preferred, in consideration that the formed copolymer is crosslinked with an isocyanate compound and desired drying property after coating is attained. These solvents may be used alone or in combination.

The amount of the solvent used may be appropriately determined depending on the various reaction conditions. Preferably, the ratio of the mass of the solvent used to the mass of the monomer used is 0.2 to 500/1, more preferably 0.4 to 100/1, still more preferably 0.6 to 50/1.

The heat resistance improving polymer preferably has a mass average molecular weight of 1,000 to 200,000. In consideration of, for example, mutual solubility with a resin used, prevention of bleed out occurring over time, heat resistance, and adhesiveness of the layer containing the polymer to adjacent layers, the mass average molecular weight is more preferably 2,000 to 100,000, still more preferably 5,000 to 50,000.

The heat resistance improving polymer has a reactive aliphatic hydroxyl group, and preferably has a hydroxyl value of 100 mgKOH/g or higher, more preferably 120 mgKOH/g or higher. The crosslinking density of the polymer depends on the hydroxyl value thereof and thus, resistance to chemicals and physical properties of a coated film containing the polymer also depend on it. When the hydroxyl value is 100 mgKOH/g or higher, a coated film containing the polymer is improved in heat resistance, surface hardness and cracking resistance.

Here, whether or not a reversible thermosensitive recording medium is formed using a resin having a hydroxyl value of 100 mgKOH/g or higher can be confirmed by, for example, analyzing the amount of the remaining hydroxyl groups and the amount of the ether bonds.

The heat resistance improving polymer preferably has an acid value of 5 mgKOH/g or lower.

The hydroxyl value and acid value can be measured according to, for example, JIS K0070:1992.

As described above, the heat resistance improver of the present invention enables various recording media to have surfaces resistant to repetitive use outdoor, no fogging caused by an erase bar, and sufficient light resistance and heat resistance with respect to formed images and images after erasure. In particular, it is suitably used in a reversible thermosensitive recording medium described below.

(Reversible Thermosensitive Recording Medium)

A reversible thermosensitive recording medium of the present invention includes a support, a reversible thermosensitive recording layer formed on the support, and a heat resistance improving layer formed on the reversible thermosensitive recording layer; and, if necessary, includes a gas barrier layer, a protective layer, and appropriately selected other layers such as an undercoat layer and a primer layer. Each layer may have a single-layer structure or a multi-layer structure.

FIG. 1 shows a layer structure of a reversible thermosensitive recording medium 10 of the present invention, wherein reference numerals 1, 2, 3, 4, 5, 6 and 7 denote a support, an undercoat layer, a reversible thermosensitive recording layer, a heat resistance improving layer, a primer layer, a gas barrier layer and a protective layer, respectively. Each layer will next be described in detail.

<Heat Resistance Improving Layer>

The heat resistance improving layer contains a heat resistance improver of the present invention and, if necessary, further contains other components.

When the heat resistance improving component is a compound according to a first embodiment represented by General Formula (1) or (2), or a compound according to a second embodiment represented by General Formula (5) or (6), the heat resistance improving layer contains a binder resin. The binder resin is preferably an ester polyol resin or acrylic polyol resin.

Notably, when the heat resistance improving component is a heat resistance improving polymer according to a first or second embodiment, no binder resin is required to be used.

The binder resin contains a polyol resin and a compound crosslinkable with a hydroxyl group of the polyol resin.

Specific examples of the polyol resin include resins having a hydroxyl group reactive to a crosslinking agent (e.g., acrylic polyol resins, polyester polyol resins, polyether polyol resins, alkyd polyol resins, polyurethane polyol resins and polyvinyl butyral resins) and resins formed by copolymerizing a monomer having a group reactive to a crosslinking agent with another monomer. Of these, particularly preferred are acrylic polyol resins, polyester polyol resins and polyether polyol resins, since they can serve as a binder matrix exhibiting excellent dispersion capability.

The acrylic polyol resins may be conventionally known organic solvent-soluble polyol resins. Examples of the hydroxyl group-containing monomer constituting them include hydroxyethyl acrylate (HEA), hydroxypropyl acrylate (HPA), 2-hydroxyethyl methacrylate (HEMA), 2-hydroxypropyl methacrylate (HPMA), 2-hydroxybutyl monoacrylate (2-HBA) and 1,4-hydroxybutyl monoacrylate (1-HBA). Among these polyol resins, those having a primary hydroxyl group are conventionally preferably used, since they can easily proceed with crosslinking reaction. Thus, although there are a wide variety of polyol resins, limitation is imposed on their practical use. In the present invention, crosslinking reaction can be remarkably accelerated and thus, not only primary hydroxyl group-containing polyol resins but also secondary hydroxyl group-containing polyol resins can be used. Use of secondary hydroxyl group-containing polyol resins can easily control flexibility of a coated film among physical properties required for resins.

The polyester polyol resins are hydroxyl group-containing condensates formed between polybasic acids and polyhydric acids. Examples of the polybasic acid include aromatic polybasic acids such as phthalic acid, isophthalic acid, terephthalic acid, trimellitic acid and pyromellitic acid; and aliphatic polybasic acids such as succinic acid, glutaric acid, adipic acid, pimelic acid, azelaic acid and dimer acid. Also, acid anhydrides of these polybasic acids may be used.

Examples of the polyhydric alcohol include low-molecular-weight polyols such as ethylene glycol, diethylene glycol, triethylene glycol, propylene glycol, dipropylene glycol, propanediol, neopentyl glycol, glycerin, trimethylolethane, trimethylolpropane, diglycerol, pentaerythritol, dipentaerythritol, diacetone glycol and hexanetriol; high-molecular-weight polyols such as polyethylene glycol, polypropylene glycol and polybutylene glycol; polyester polyols formed from these polyols; condensates formed between hydroxyl carboxylic acids and a cyclic lactone; and products formed through ring-opening polymerization between hydroxyl carboxylic acids and a cyclic lactone (e.g., polybutylolactonediol and polycaprolactonediol).

Preferably, the reactive aliphatic hydroxyl group or the reactive aliphatic mercapto group contained in the heat resistance improver according to the first or second embodiment of the present invention is crosslinked with an isocyanate compound.

Examples of the isocyanate compound include modified products (e.g., urethane-modified products, allophanate-modified products, isocyanurate-modified products, burette-modified products, carbodiimide-modified products and blocked isocyanates) of known isocyanate monomers. Examples of the isocyanate monomer, which forms these modified products, include tolylene diisocyanate (TDI), 4,4'-diphenylmethane diisocyanate (MDI), xylylene diisocyanate (XDI), naphthylene diisocyanate (NDI), paraphenylene diisocyanate (PPDI), tetramethylxylylene diisocyanate (TMXDI), hexamethylene diisocyanate (HDI), dicyclohexylmethane diisocyanate (HMDI), isophorone diisocyanate (IPDI), lysine diisocyanate (LDI), isopropylidene bis(4-cyclohexylisocyanate) (IPC), cyclohexyl diisocyanate (CHDI) and tolidine diisocyanate (TODI). However, the isocyanate monomer which can be used in the present invention is not limited to the above-listed compounds.

Also, a catalyst may be used as a crosslinking accelerator (curing agent) in crosslinking reaction between the isocyanate compound and the reactive aliphatic hydroxyl group or the reactive aliphatic mercapto group. Examples of the crosslinking accelerator include tertiary amines (e.g., 1,4-diaza-bicyclo[2.2.2]octane) and metal compounds (e.g., organotin compound). All the crosslinking agent added do not need to participate in the crosslinking reaction. In other words, an unreacted curing agent may exist in the reaction system. Since this type of the crosslinking reaction proceeds with time, the presence of the unreacted curing agent does not indicate that the crosslinking reaction does not proceed at all. Even if the unreacted curing agent is detected, it does not mean that a crosslinked resin is absent. It can be confirmed by immersing the formed coated film in a solvent having high solubility whether or not the polymer is in a crosslinked state or non-crosslinked state. The polymer in a non-crosslinked state begins to dissolve in the solvent and does not remain as a solute, and therefore the presence or absence of a polymer structure of the solute may be analyzed. If the polymer structure is not confirmed in the solute, it is believed that the polymer is in a non-crosslinked state, making it possible to distinguish it from the polymer in a crosslinked state. The crosslinking degree can be expressed by a gel fraction.

The gel fraction refers to a ratio of a gel produced when resin (solute) is lack of independent mobility by the interaction in a solvent to produce an aggregated and solidified state (gel). The gel fraction of the resin is preferably 30% or higher, more preferably 50% or higher, still more preferably 70% or higher, particularly preferably 80% or higher. When the gel fraction is low, the formed reversible thermosensitive recording medium tends to degrade in its durability after repetitive use. Thus, the gel fraction is increased by mixing the resin with a resin curable with, for example, heat, UV and EB; or by crosslinking the resin itself.

The gel fraction is measured in the following manner. Specifically, a film is separated from a support, followed by weighing for the film (initial mass). Then, the film is interposed between 400-mesh wire gauzes and immersed in a solvent capable of dissolving uncrosslinked resin for 24 hours, followed by drying in vacuum and weighing (mass after drying).

From the obtained values, the gel faction can be calculated using the following Equation:

$$\text{Gel fraction (\%)}=(\text{mass after drying (g)})/(\text{initial mass (g)})\times 100$$

Notably, the mass of other components than the resin (e.g., particles of organic low-molecular-weight compounds), which are contained in the heat resistance improving layer, is not taken into account for calculation. When the mass of particles of organic low-molecular-weight compounds is not previously obtained, it may be calculated from a mass ratio of the resin to the particles of organic low-molecular-weight compounds. The mass ratio can be determined based on their specific gravities and a ratio of an area occupied with the resin to that occupied with the particles of organic low-molecular-weight compounds by observing a unit area of the cross section of the film through TEM, SEM, etc.

The method for forming the heat resistance improving layer is not particularly limited and can be appropriately selected depending on the purpose. Preferred examples thereof include (1) a method in which a support is coated with a heat resistance improving layer-coating liquid prepared by dissolving or dispersing in a solvent the binder resin, the heat resistance improver according to the first or second embodiment and the isocyanate compound, and then the solvent is evaporated to form a sheet in parallel with or before crosslinking; and (2) a method in which a support is coated with a heat resistance improving layer-coating liquid prepared by dissolving or dispersing in a solvent the heat resistance polymer according to the first or second embodiment and the isocyanate compound, and then the solvent is evaporated to form a sheet in parallel with or before crosslinking.

Also, in order for the heat resistance improving layer-coating liquid to exhibit high performances suited for a coating material, various pigments, defoamers, dispersants, slipping agents, antiseptics, crosslinking agents and plasticizers may be added thereto.

The method for applying the heat resistance improving layer-coating liquid is not particularly limited and can be appropriately selected depending on the purpose. For example, while a roll-shaped support is continuously conveyed, the coating liquid is applied on the support by known coating methods such as blade coating, wire bar coating, spray coating, air knife coating, bead coating, curtain coating, gravure coating, kiss coating, reverse roll coating, dip coating and die coating. Alternatively, a support is previously cut into sheets, and then while the sheets are conveyed, the coating liquid is applied onto them by the above coating method.

The resin in the heat resistance improving layer can be cured through heating, ultraviolet irradiation, or electron beam irradiation.

The ultraviolet irradiation may be performed by any known ultraviolet irradiation devices, and examples thereof include those equipped with a light source, a lighting fixture, a power supply, a cooling device, and/or a transfer device.

Examples of the light source include mercury lamps, metal halide lamps, gallium lamps, mercury-xenon lamps and flash lamps. The wavelength of the light source can be appropriately selected in consideration of an ultraviolet absorption wavelength of a photopolymerization initiator and a photopolymerization accelerator, which are added to a composition for a reversible thermosensitive recording medium.

The irradiation conditions of an ultraviolet ray are not particularly limited and can be appropriately selected depending on the purpose. For example, the transfer speed and the output of a lamp may be determined in consideration of the required irradiation energy for crosslinking of the resin.

The electron beam irradiation can be performed using known electron beam irradiation devices. The electron beam irradiation devices can be roughly classified into scanning (scanbeam)-type devices and non-scanning (areabeam)-type devices. The irradiation conditions can be determined according to, for example, the irradiation area and irradiation dose. Also, the irradiation dose of the electron beam can be determined from the following Equation 2 in consideration of the irradiation dose required for crosslinking the resin, the electron current, the irradiation width and the transfer speed.

<Equation 2>

$$D=(\Delta E/\Delta R)\cdot\eta\cdot I/(W\cdot V)$$

where D denotes a required irradiation dose (Mrad), $\Delta E/\Delta R$ denotes an average energy loss, $\eta$ denotes an efficiency, I denotes an electron current (mA), W denotes an irradiation width (cm), and V denotes a transfer speed (cm/s).

From an industrial point of view, the following Equation 3 obtained by simplifying Equation 2 is preferably used.

<Equation 3>

$$D\cdot V=K\cdot I/W$$

Here, a device rating is shown by Mrad·m/min, and about 20 mA to about 500 mA is selected as an electron current rating.

Regarding the heat resistance improving layer, its transmittance with respect to a UV ray having a wavelength of 390 nm is preferably 20% or lower, more preferably 15% or lower.

This UV transmittance (i.e., transmittance with respect to light of 390 nm) of the heat resistance improving layer is measured using a spectrophotometer with being set to a transmission mode. Here, the UV transmittance was measured in the following manner. Specifically, a heat resistance improving layer was formed on a transparent film having no absorption with respect to light of 390 nm, and its transmittance in the ultraviolet range was measured with Spectrophotometer U-4100 (product of Hitachi, Ltd.) using the same transparent film as reference.

The amount of the heat resistance improver according to the first embodiment contained in the heat resistance improving layer is preferably 30% by mass to 80% by mass, more preferably 50% by mass to 70% by mass.

The thickness of the heat resistance improving layer is not particularly limited and can be appropriately selected depending on the purpose. It is preferably 0.3 μm to 10.0 μm, more preferably 1.0 μm to 5.0 μm.

<Reversible Thermosensitive Recording Layer>

The reversible thermosensitive recording layer contains an electron-donating color-developing compound and an electron-accepting compound, and reversibly changes in color tone depending on a change in temperature.

The phrase "reversibly changes in color tone depending on a change in temperature" for the reversible thermosensitive recording layer means that a phenomenon of reversibly causing a visual change is observed depending on a change in temperature, and also means that a relatively color-developed state and a relatively color-erased state can be formed depending on the heating temperature and on the cooling speed after heating. Here, the visible change is classified into a change in color and a change in shape. In the present invention, a material causing a change in color is mainly used. The change in color is, for example, changes in transmittance, reflectance, absorption wavelength and scattering degree, and an actual reversible thermosensitive recording medium displays by combining these changes. More specifically, the reversible thermosensitive recording layer is not particularly limited, so long as it can reversibly change in transparency or color toner by the action of heat, and can be appropriately selected depending on the purpose. For example, the reversible thermosensitive recording layer is a layer which turns into a first color at a first specific temperature higher than ambient temperature, and turns into a second color after heating at a second specific temperature higher than the first specific temperature and then cooling. In the reversible thermosensitive recording layer, the first color is preferably different from the second color.

Specific examples include a material which becomes transparent at a first specific temperature and becomes opaque at a second specific temperature (JP-A No. 55-154198), a material which develops color at a second specific temperature and becomes colorless at a first specific temperature (e.g., JP-A Nos. 04-224996, 04-247985 and 04-267190), a material which becomes opaque at a first specific temperature and becomes transparent at a second specific temperature (e.g., JP-A No. 03-169590), and a material which turns into black, red, blue, etc. at a first specific temperature and becomes colorless at a second specific temperature (JP-A Nos. 02-188293 and 02-188294).

Figure 2:
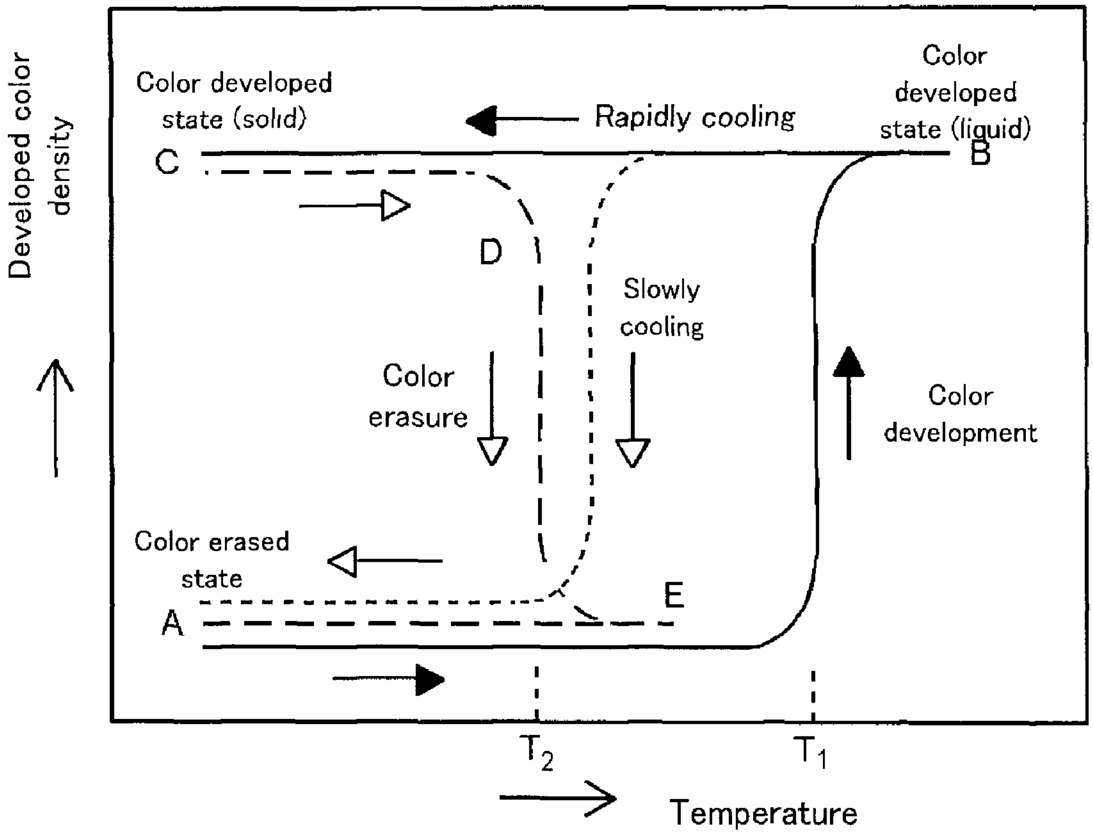
FIG. 2 is a chart in relation to color developing/erasing characteristics (color developing/erasing phenomenon) in a reversible thermosensitive recording medium of the present invention.

The reversible thermosensitive recording medium of the present invention can form a relatively color-developed state and a relatively color-erased state depending on the heating temperature or the cooling speed after heating. Here, a basic color developing/erasing phenomenon of a composition containing a color former and a color developer will be described. FIG. 2 shows a relation between the density of developed color and the temperature of the reversible thermosensitive recording medium. As the temperature of a recording medium in a color erased state (A) is raised, color is developed at a temperature T1 at which melting begins, to thereby attain a color developed (molten) state (B). When the recording medium in the color developed (molten) state (B) is rapidly cooled, the temperature thereof can be decreased to room temperature while maintaining the color developed state to attain a color developed (solidified) state (C). It depends on the cooling speed of the recording medium in the molten state whether or not this color developed state is attained. Specifically, color erasure is performed when the recording medium is slowly cooled and thus, the recording medium becomes in the color erased state (A) (i.e., the initial state) or in a state where the color density thereof is lower than the color developed (solidified) state (C) attained through rapid cooling of the medium. Meanwhile, as the recording medium in the color developed (solidified) state (C) is raised in temperature again, color erasure is performed at a temperature T2 lower than the color developing temperature (from D to E). In this state, when cooled, the recording medium becomes again in the color erased state (A) (i.e., the initial state). An actual color developing temperature and an actual color erasure temperature of the recording medium can be appropriately set depending on the purpose by appropriately selecting a color developer used and a color former used. In some cases, the color density of a recording medium in a molten color developed state is different from that of the recording medium obtained after rapid cooling.

In the reversible thermosensitive recording medium, the color developed state (C) attained after rapid cooling of a recording medium in a molten state is a state where a color developer and a color former are mixed with each other while the molecules thereof can be in contact with each other for reaction. The state is often a solid state. It is considered that this state is a state where a color developer and a color former are aggregated to maintain to develop color, and stable color development is obtained by formation of the aggregated structure. On the other hand, the color erased state is a state where they are phase-separated. Presumably, in this state, molecules of the color developer, the color former, or both of them are aggregated to form a domain or are crystallized, resulting in that they are stably phase-separated. In many cases, when they are phase-separated and the color developer is crystallized, complete color erasure is performed. In color erasure brought by slow cooling of a recording medium in a molten state or brought by heating of the recording medium in a color developed state (shown in FIG. 2), the aggregated structure changes at a temperature at which color erasure is observed, and a color developer and a color former are phase-separated and the color developer is crystallized.

In the reversible thermosensitive recording medium of the present invention, color development (recording) may be performed by heating the medium with a thermal head to a temperature at which a color developer and a color former are molten and mixed, and then rapidly cooling it. Meanwhile, color erasure is performed by slowly cooling the heated medium or heating the cooled medium to a temperature slightly lower than the color developing temperature. These methods are the same in that the color developer and the color former are phase-separated or the medium is temporarily maintained at a temperature at which at least one of them is crystallized. In order to avoid such phase separation and crystallization, the medium is rapidly cooled for color development. Here, in one composition, rapid cooling and slow cooling are in a relative relationship, and they vary according to a combination of the color former used and the color developer used.

—Electron-Accepting Compound—

The electron-accepting compound (color developer) is not particularly limited, so long as it can reversibly develop and erase color by the action of heat, and can be appropriately selected according to the purpose. Preferred examples thereof include compounds having in the molecule one or more of a structure selected from (i) a structure allowing an electron-donating color-developing compound (color former) to develop color (e.g., a phenolic hydroxyl group, a carboxyl group and a phosphoric acid group) and (ii) a structure controlling intermolecular force (e.g., a structure linked with a long chain hydrocarbon group). In the structure (ii), the linking moiety may be a hetero atom-containing di- or more valent linking group and also, the long chain hydrocarbon group may contain the same linking group, an aromatic group, or both of them. In particular, preferred are phenol compounds represented by the following General Formula (A).

General Formula.(A)

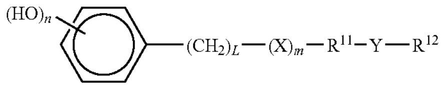

where L is a natural number of 0 to 2, m is an integer of 0 or 1, n is an integer of 1 to 3, X and Y each represent an N atom or O atom-containing divalent group, $R^{11}$ represents a substituted or unsubstituted aliphatic hydrocarbon group having 2 or more carbon atoms, and $R^{12}$ represents an aliphatic hydrocarbon group having 1 or more carbon atoms.

The aliphatic hydrocarbon group represented by $R^{11}$ or $R^{12}$ may be linear or branched and have an unsaturated bond. Examples of the substituent the hydrocarbon group may have include a hydroxyl group, halogen atoms and alkoxy group. When the total number of carbon atoms contained in groups $R^{11}$ and $R^{12}$ is 7 or less, stable color development or color erasure deteriorates. Thus, the total number is preferably 8 or more, more preferably 11 or more.

Preferred groups represented by $R^{11}$ are those represented by the following structural formulas.

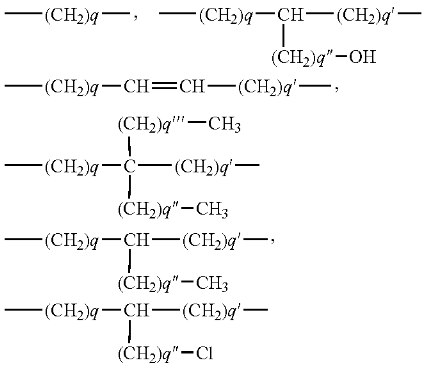

where each of q, q', q" and q"' is an integer satisfying the conditions: the total number of carbon atoms contained in the groups represented by $R^{11}$ is 2 or more. Among them, groups represented by $-(CH_2)_q-$ are particularly preferred.

Preferred groups represented by $R^{12}$ are those represented by the following structural formulas.

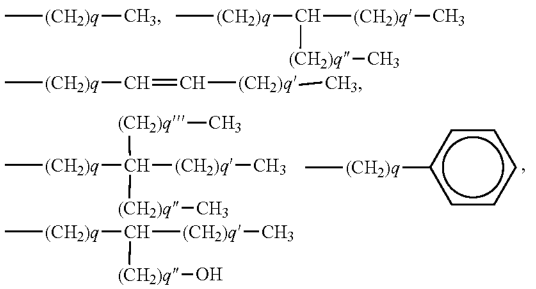

-continued

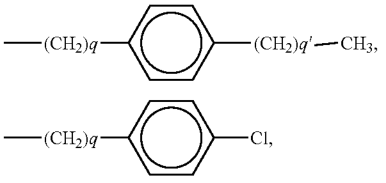

where each of q, q', q" and q"' is an integer satisfying the conditions: the total number of carbon atoms contained in the groups represented by $R^{12}$ is 1 or more. Among them, groups represented by $-(CH_2)_q-CH_3$ are particularly preferred.

In General Formula (A), each of X and Y represents a hetero atom-containing divalent organic group, and particularly preferably represents a nitrogen or oxygen atom-containing divalent organic group; e.g., divalent organic groups containing at least one selected from the groups having the following structural formulas.

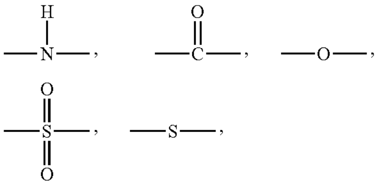

Preferred examples of the hetero atom-containing divalent organic group include those having the following structural formulas.

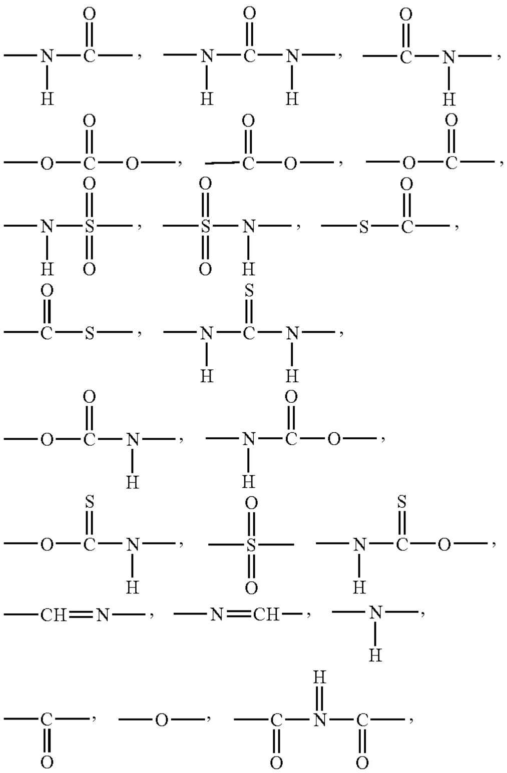

-continued
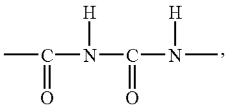,
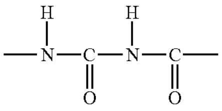
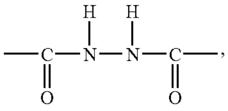,
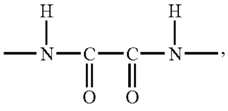,
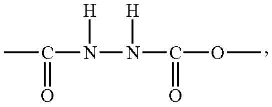,
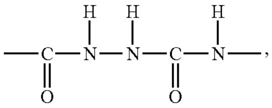,
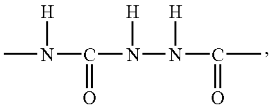,
-continued
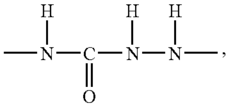,
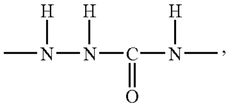,
Of these, particularly preferred are those having the following structural formulas.
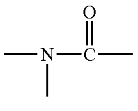,
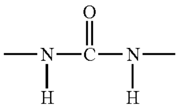
Examples of the phenol compound represented by General Formula (A) include compounds given below. However, the compound which can be used in the present invention is not limited thereto.
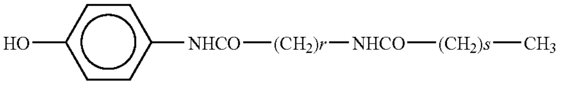
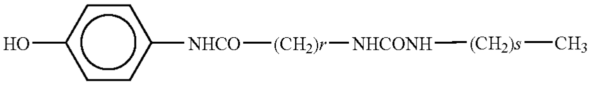
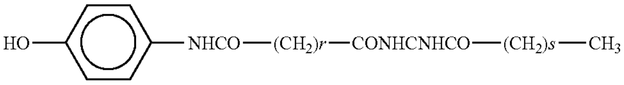
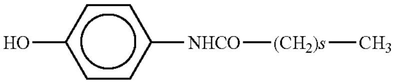
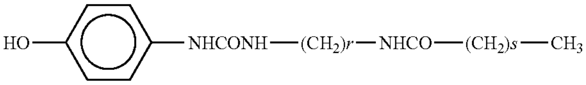
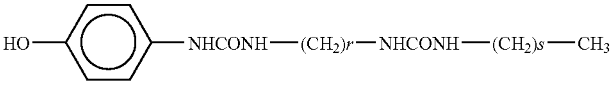
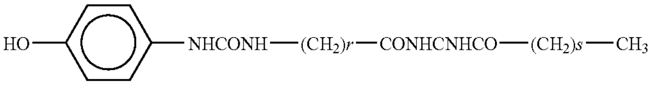
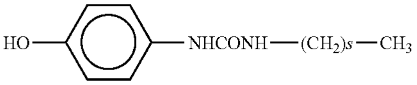
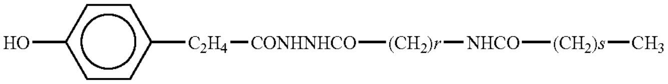
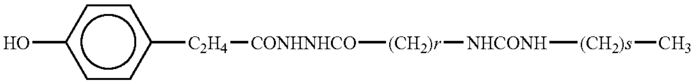
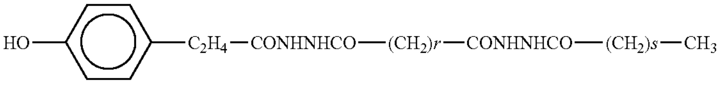
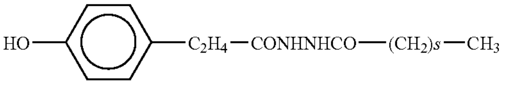

where r is an integer of 2 or more and s is an integer to 1 or more.

Electron-Donating Color-Developing Compound—

The electron-donating color-developing compound (color former) is not particularly limited and can be appropriately selected depending on the purpose. For example, leuco dyes are preferably used.

The leuco dye is preferably a fluoran compound or an azaphthalide compound. Examples thereof include
2-anilino-3-methyl-6-diethylaminofluoran,
2-anilino-3-methyl-6-di(n-butylamino)fluoran,
2-anilino-3-methyl-6-(N-n-propyl-N-methylamino)fluoran,
2-anilino-3-methyl-6-(N-isopropyl-N-methylamino)fluoran,
2-anilino-3-methyl-6-(N-isobutyl-N-methylamino)fluoran,
2-anilino-3-methyl-6-(N-n-amyl-N-methylamino)fluoran,
2-anilino-3-methyl-6-(N-sec-butyl-N-methylamino)fluoran,
2-anilino-3-methyl-6-(N-n-amyl-N-ethylamino)fluoran,
2-anilino-3-methyl-6-(N-iso-amyl-N-ethylamino)fluoran,
2-anilino-3-methyl-6-(N-n-propyl-N-isopropylamino)fluoran,
2-anilino-3-methyl-6-(N-cyclohexyl-N-methylamino)fluoran,
2-anilino-3-methyl-6-(N-ethyl-p-toluidino)fluoran,
2-anilino-3-methyl-6-(N-methyl-p-toluidino)fluoran,
2-(m-trichloromethylanilino)-3-methyl-6-diethylaminofluoran,
2-(m-trifluoromethylanilino)-3-methyl-6-diethylaminofluoran,
2-(m-trichloromethylanilino)-3-methyl-6-(N-cyclohexyl-N-methylamino)fluoran,
2-(2,4-dimethylanilino)-3-methyl-6-diethylaminofluoran,
2-(N-ethyl-p-toluidino)-3-methyl-6-(N-ethylanilino)fluoran,
2-(N-ethyl-p-toluidino)-3-methyl-6-(N-propyl-p-toluidino)fluoran,
2-anilino-6-(N-n-hexyl-N-ethylamino)fluoran,
2-(o-chloroanilino)-6-diethylaminofluoran,
2-(o-chloroanilino)-6-dibutylaminofluoran,
2-(m-trifluoromethylanilino)-6-diethylaminofluoran,
2,3-dimethyl-6-dimethylaminofluoran,
3-methyl-6-(N-ethyl-p-toluidino)fluoran,
2-chloro-6-diethylaminofluoran, 2-bromo-6-diethylaminofluoran,
2-chloro-6-dipropylaminofluoran, 3-chloro-6-cyclohexylaminofluoran,
3-bromo-6-cyclohexylaminofluoran,
2-chloro-6-(N-ethyl-N-isoamylamino)fluoran,
2-chloro-3-methyl-6-diethylaminofluoran,
2-anilino-3-chloro-6-diethylaminofluoran,
2-(o-chloroanilino)-3-chloro-6-cyclohexylaminofluoran,
2-(m-trifluoromethylanilino)-3-chloro-6-diethylaminofluoran,
2-(2,3-dichloroanilino)-3-chloro-6-diethylaminofluoran,
1,2-benzo-6-diethylaminofluoran,
3-diethylamino-6-(m-trifluoromethylanilino)fluoran,
3-(1-ethyl-2-methylindol-3-yl)-3-(2-ethoxy-4-diethylaminophenyl)-4-azaphthalide,
3-(1-ethyl-2-methylindol-3-yl)-3-(2-ethoxy-4-diethylaminophenyl)-7-azaphthalide,
3-(1-octyl-2-methylindol-3-yl)-3-(2-ethoxy-4-diethylaminophenyl)-4-azaphthalide,
3-(1-ethyl-2-methylindol-3-yl)-3-(2-methyl-4-diethylaminophenyl)-4-azaphthalide,
3-(1-ethyl-2-methylindol-3-yl)-3-(2-methyl-4-diethylaminophenyl)-7-azaphthalide,
3-(1-ethyl-2-methylindol-3-yl)-3-(4-diethylaminophenyl)-4-azaphthalide,
3-(1-ethyl-2-methylindol-3-yl)-3-(4-N-n-amyl-N-methylaminophenyl)-4-azaphthalide,
3-(1-methyl-2-methylindol-3-yl)-3-(2-hexyloxy-4-diethylaminophenyl)-4-azaphthalide,
3,3-bis(2-ethoxy-4-diethylaminophenyl)-4-azaphthalide, and
3,3-bis(2-ethoxy-4-diethylaminophenyl)-7-azaphthalide.

As the electron-donating color-developing compound (color former), in addition to the fluoran compounds and the azaphthalide compounds, conventionally known leuco dyes can be used. Examples thereof include
2-(p-acetylanilino)-6-(N-n-amyl-N-n-butylamino)fluoran,
2-benzylamino-6-(N-ethyl-p-toluidino)fluoran,
2-benzylamino-6-(N-methyl-2,4-dimethylanilino)fluoran,
2-benzylamino-6-(N-ethyl-2,4-dimethylanilino)fluoran,
2-benzylamino-6-(N-methyl-p-toluidino)fluoran,
2-benzylamino-6-(N-ethyl-p-toluidino)fluoran,
2-(di-p-methylbenzylamino)-6-(N-ethyl-p-toluidino)fluoran,
2-(α-phenylethylamino)-6-(N-ethyl-p-toluidino)fluoran,
2-methylamino-6-(N-methylanilino)fluoran,
2-methylamino-6-(N-ethylanilino)fluoran,
2-methylamino-6-(N-propylanilino)fluoran,
2-ethylamino-6-(N-methyl-p-toluidino)fluoran,
2-methylamino-6-(N-methyl-2,4-dimethylanilino)fluoran,
2-ethylamino-6-(N-ethyl-2,4-dimethylanilino)fluoran,
2-dimethylamino-6-(N-methylanilino)fluoran,
2-dimethylamino-6-(N-ethylanilino)fluoran,
2-diethylamino-6-(N-methyl-p-toluidino)fluoran,
2-diethylamino-6-(N-ethyl-p-toluidino)fluoran,
2-dipropylamino-6-(N-methylanilino)fluoran,
2-dipropylamino-6-(N-ethylanilino)fluoran,
2-amino-6-(N-methylanilino)fluoran,
2-amino-6-(N-ethylanilino)fluoran,
2-amino-6-(N-propylanilino)fluoran,
2-amino-6-(N-methyl-p-toluidino)fluoran,
2-amino-6-(N-ethyl-p-toluidino)fluoran,
2-amino-6-(N-propyl-p-toluidino)fluoran,
2-amino-6-(N-methyl-p-ethylanilino)fluoran,
2-amino-6-(N-ethyl-p-ethylanilino)fluoran,
2-amino-6-(N-propyl-p-ethylanilino)fluoran,
2-amino-6-(N-methyl-2,4-dimethylanilino)fluoran,
2-amino-6-(N-ethyl-2,4-dimethylanilino) fluoran,
2-amino-6-(N-propyl-2,4-dimethylanilino)fluoran,
2-amino-6-(N-methyl-p-chloroanilino)fluoran,
2-amino-6-(N-ethyl-p-chloroanilino)fluoran,
2-amino-6-(N-propyl-p-chloroanilino)fluoran,
1,2-benzo-6-(N-ethyl-N-isoamylamino)fluoran,
1,2-benzo-6-dibutylaminofluoran,
1,2-benzo-6-(N-methyl-N-cyclohexylamino)fluoran, and
1,2-benzo-6-(N-ethyl-N-toluidino)fluoran.

These compounds may be used alone or in combination. Also, reversible thermosensitive recording media assuming multi-color or full-color can be produced by laminating layers capable of developing colors having different color tones.

The ratio of the electron-donating color-developing compound (color former) to the electron-accepting compound (color developer) is not determined depending on a single factor since a suitable ratio varies depending on a combination of compounds to be used, and a molar ratio of the color developer to the color former is preferably 0.1/1 to 20/1, and more preferably 0.2/1 to 10/1. When the amount of the developer deviates from the above range, the density of developed color problematically decreases. Also, the color former and the color developer can be used in a state where they are encapsulated in a microcapsule.

—Color Erasure Accelerator—

In the present invention, by using the color developer in combination with a color erasure accelerator—a compound having at least one of an amide group, an urethane group and an urea group in the molecule, an intermolecular interaction is induced between the color erasure accelerator and the developer in the process of forming the erased state, and thus making it possible to remarkably increase the erasing rate.

The color erasure accelerator may be compounds having in the molecule at least one selected from an amide group, a urethane group and a urea group. In particular, the below-listed compounds are preferred.

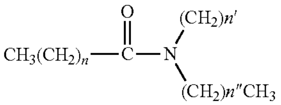

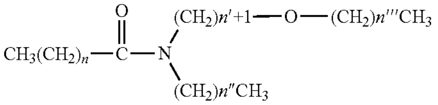

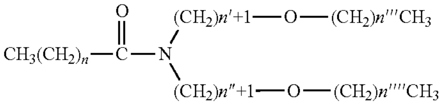

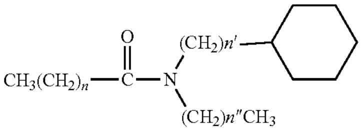

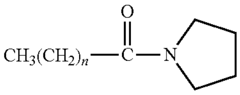

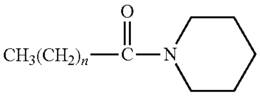

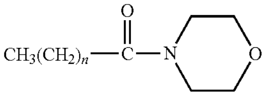

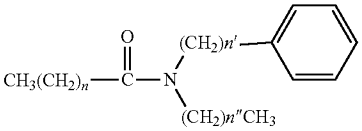

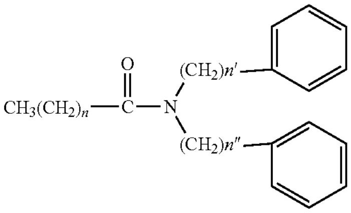

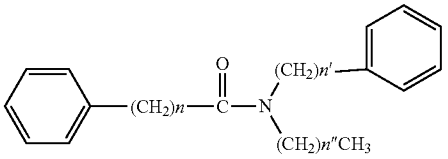

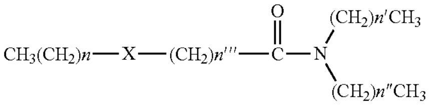

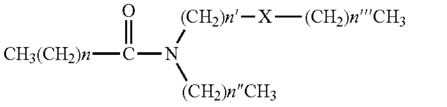

-continued

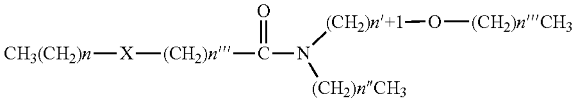

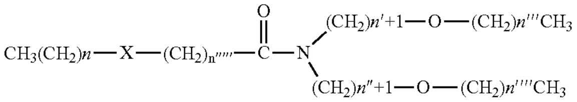

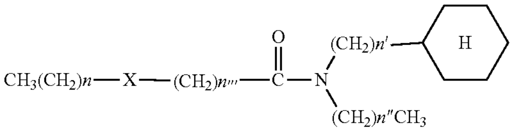

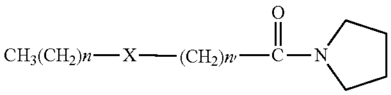

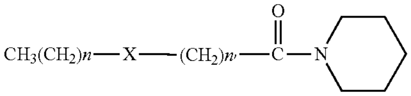

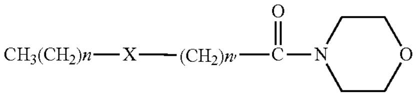

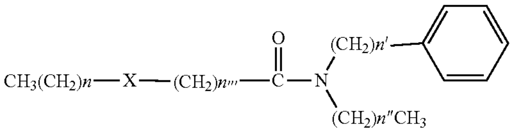

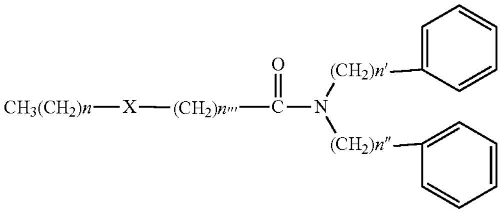

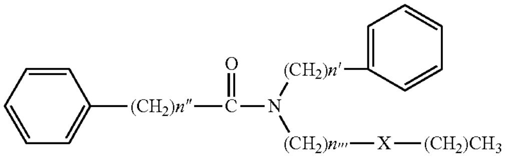

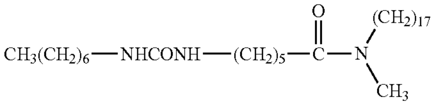

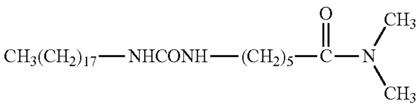

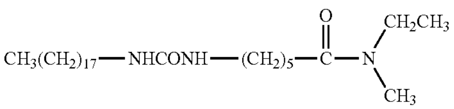

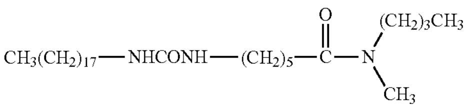

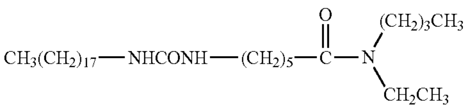

-continued

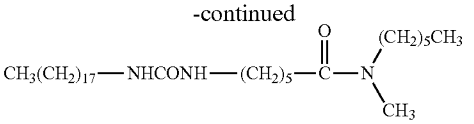

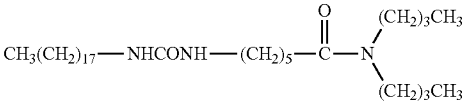

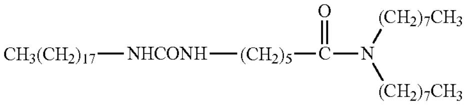

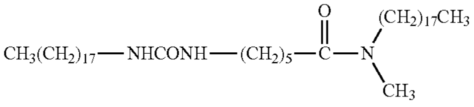

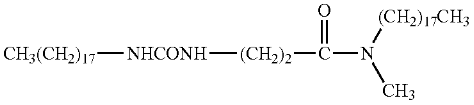

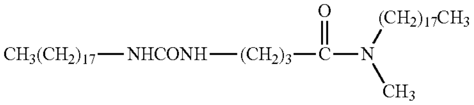

where each of n, n', n'', n''' and n'''' is an integer of 0 to 21, with the proviso that at least one of n, n', n'', n''' and n'''' is more than 5.

More specifically, preferred compounds are compounds (1) to (81).

(1) $C_{11}H_{23}CONHC_{12}H_{25}$,
(2) $C_{15}H_{31}CONHC_{16}H_{33}$,
(3) $C_{17}H_{35}CONHC_{18}H_{37}$,
(4) $C_{17}H_{35}CONHC_{18}H_{35}$,
(5) $C_{21}H_{41}CONHC_{18}H_{37}$,
(6) $C_{15}H_{31}CONHC_{18}H_{37}$,
(7) $C_{17}H_{35}CONHCH_2NHCOC_{17}H_{35}$,
(8) $C_{11}H_{23}CONHCH_2NHCOC_{11}H_{23}$,
(9) $C_7H_{15}CONHC_2H_4NHCOC_{17}H_{35}$,
(10) $C_9H_{19}CONHC_2H_4NHCOC_9H_{19}$,
(11) $C_{11}H_{23}CONHC_2H_4NHCOC_{11}H_{23}$,
(12) $C_{17}H_{35}CONHC_2H_4NHCOC_{17}H_{35}$,
(13) $(CH_3)_2CHC_{14}H_{35}CONHC_2H_4NHCOC_{14}H_{35}(CH_3)_2$,
(14) $C_{21}H_{43}CONHC_2H_4NHCOC_{21}H_{43}$,
(15) $C_{17}H_{35}CONHC_6H_{12}NHCOC_{17}H_{35}$,
(16) $C_{21}H_{43}CONHC_6H_{12}NHCOC_{21}H_{43}$,
(17) $C_{17}H_{33}CONHCH_2NHCOC_{17}H_{33}$,
(18) $C_{17}H_{33}CONHC_2H_4NHCOC_{17}H_{33}$,
(19) $C_{21}H_{41}CONHC_2H_4NHCOC_{21}H_{41}$,
(20) $C_{17}H_{33}CONHC_6H_{12}NHCOC_{17}H_{33}$,
(21) $C_8H_{17}NHCOC_2H_4CONHC_{18}H_{37}$,
(22) $C_{10}H_{21}NHCOC_2H_4CONHC_{10}H_{21}$,
(23) $C_{12}H_{25}NHCOC_2H_4CONHC_{12}H_{25}$,
(24) $C_{18}H_{37}NHCOC_2H_4CONHC_{18}H_{37}$,
(25) $C_{21}H_{43}NHCOC_2H_4CONHC_{21}H_{43}$,
(26) $C_{18}H_{37}NHCOC_6H_{12}CONHC_{18}H_{37}$,
(27) $C_{18}H_{35}NHCOC_4H_8CONHC_{18}H_{35}$,
(28) $C_{18}H_{35}NHCOC_8H_{16}CONHC_{18}H_{35}$,
(29) $C_{12}H_{25}OCONHC_{18}H_{37}$,
(30) $C_{13}H_{27}OCONHC_{18}H_{37}$,
(31) $C_{16}H_{33}OCONHC_{18}H_{37}$,
(32) $C_{18}H_{37}OCONHC_{18}H_{37}$,
(33) $C_{21}H_{43}OCONHC_{18}H_{37}$,
(34) $C_{12}H_{25}OCONHC_{16}H_{33}$,
(35) $C_{13}H_{27}OCONHC_{16}H_{33}$,
(36) $C_{16}H_{33}OCONHC_{16}H_{33}$,

(37) $C_{18}H_{37}OCONHC_{16}H_{33}$,
(38) $C_{21}H_{43}OCONHC_{16}H_{33}$,
(39) $C_{12}H_{25}OCONHC_{14}H_{29}$,
(40) $C_{13}H_{27}OCONHC_{14}H_{29}$,
(41) $C_{16}H_{33}OCONHC_{14}H_{29}$,
(42) $C_{18}H_{37}OCONHC_{14}H_{29}$,
(43) $C_{22}H_{45}OCONHC_{14}H_{29}$,
(44) $C_{12}H_{25}OCONHC_{12}H_{37}$,
(45) $C_{13}H_{27}OCONHC_{12}H_{37}$,
(46) $C_{16}H_{33}OCONHC_{12}H_{37}$,
(47) $C_{18}H_{37}OCONHC_{12}H_{37}$,
(48) $C_{21}H_{43}OCONHC_{12}H_{37}$,
(49) $C_{22}H_{45}OCONHC_{18}H_{37}$,
(50) $C_{18}H_{37}NHCOOC_2H_4OCONHC_{18}H_{37}$,
(51) $C_{18}H_{37}NHCOOC_3H_6OCONHC_{18}H_{37}$,
(52) $C_{18}H_{37}NHCOOC_4H_8OCONHC_{18}H_{37}$,
(53) $C_{18}H_{37}NHCOOC_6H_{12}OCONHC_{18}H_{37}$,
(54) $C_{18}H_{37}NHCOOC_8H_{16}OCONHC_{18}H_{37}$,
(55) $C_{18}H_{37}NHCOOC_2H_{40}C_2H_4OCONHC_{18}H_{37}$,
(56) $C_{18}H_{37}NHCOOC_3H_{60}C_3H_6OCONHC_{18}H_{37}$,
(57) $C_{18}H_{37}NHCOOC_{12}H_{24}OCONHC_{18}H_{37}$,
(58) $C_{18}H_{37}NHCOOC_2H_{40}C_2H_{40}C_2H_4OCONHC_{18}H_{37}$,
(59) $C_{16}H_{33}NHCOOC_2H_4OCONHC_{16}H_{33}$,
(60) $C_{16}H_{33}NHCOOC_3H_6OCONHC_{16}H_{33}$,
(61) $C_{16}H_{33}NHCOOC_4H_8OCONHC_{16}H_{33}$,
(62) $C_{16}H_{33}NHCOOC_6H_{12}OCONHC_{16}H_{33}$,
(63) $C_{16}H_{33}NHCOOC_8H_{16}OCONHC_{16}H_{33}$,
(64) $C_{18}H_{37}OCOHNC_6H_{12}NHCOOC_{18}H_{37}$,
(65) $C_{16}H_{33}OCOHNC_6H_{12}NHCOOC_{16}H_{33}$,
(66) $C_{14}H_{29}OCOHNC_6H_{12}NHCOOC_{14}H_{29}$,
(67) $C_{12}H_{25}OCOHNC_6H_{12}NHCOOC_{12}H_{25}$,
(68) $C_{10}H_{21}OCOHNC_6H_{12}NHCOOC_{10}H_{21}$,
(69) $C_8H_{17}OCOHNC_6H_{12}NHCOOC_8H_{17}$, (70)

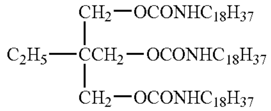

(71)

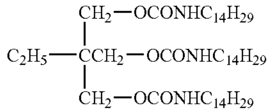

(72)

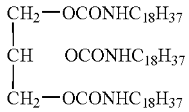

(73)

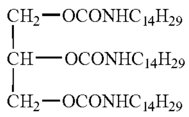

(74)

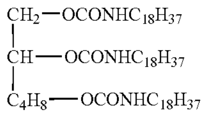

(75)

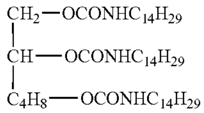

-continued (76)

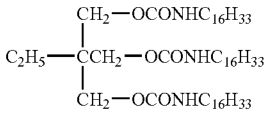

(77)

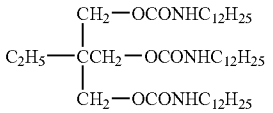

(78)

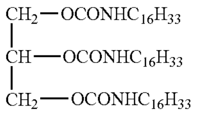

(79)

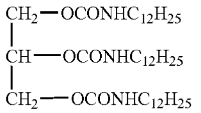

(80)

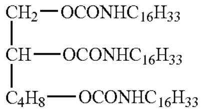

(81)

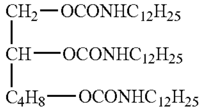

The amount of the color erasure accelerator added is preferably 0.1 parts by mass to 300 parts by mass, more preferably 3 parts by mass to 100 parts by mass, per 100 parts by mass of the color developer. When it is less than 0.1 parts by mass, the effect commensurate with the addition of the color erasure accelerator may not be obtained; whereas it is more than 300 parts by mass, the density of developed color may be decreased.

The reversible thermosensitive recording layer may contain, in addition to the above components, a binder resin; and, if necessary, may contain various additives used for improving coating property of a reversible thermosensitive recording layer-coating liquid and for improving color development/erasure properties. Examples of the additive include crosslinking agents, crosslinking accelerators, fillers, lubricants, surfactants, conductivity-imparting agents, bulking agents, antioxidants, photostabilizers, color development stabilizers and plasticizers.

The binder resin is not particularly limited and can be appropriately selected depending on the purpose. Examples thereof include polyvinyl chloride resins, polyvinyl acetate resins, vinyl chloride-vinyl acetate copolymers, ethyl cellulose, polystyrene resins, styrene copolymers, phenoxy resins, polyester resins, aromatic polyester resins, polyurethane resins, polycarbonate resins, polyacrylate resins, polymethacrylate resins, acrylic copolymers, maleic acid-based copolymers, polyvinyl alcohol resins, modified polyvinyl alcohol resins, hydroxyethyl cellulose, carboxymethyl cellulose and starches.

These binder resins play a role in maintaining materials of a composition to be uniformly dispersed so as to prevent localizing thereof due to application of heat upon recording and erasing. Thus, the binder resin used preferably has high heat resistance. The binder resin used is preferably a crosslinking agent-containing curable resin which can be cured by, for example, heat, ultraviolet ray and electron beam (hereinafter referred to as a "resin in a crosslinked state"). The reversible thermosensitive recording layer containing the curable resin is improved in heat resistance and film strength. In addition, a reversible thermosensitive recording medium containing the layer is improved in durability after repetitive use.

The curable resin is not particularly limited and can be appropriately selected depending on to the purpose. Examples thereof include resins having a group capable of reacting with a crosslinking agent (e.g., acrylic polyol resins, polyester polyol resins, polyurethane polyol resins, phenoxy resins, polyvinyl butyral resins, cellulose acetate propionate and cellulose acetate butyrate) and resins produced by copolymerizing a monomer reactive to a crosslinking agent with another monomer. Among them, acrylic polyol resins, polyester polyol resins, and polyurethane polyol resins are particularly preferred.

The curable resin preferably has a hydroxyl value of 70 mgKOH/g or higher, more preferably 90 mgKOH/g or higher, since a coated film is improved in durability, surface hardness and cracking resistance. The crosslinking density of the resin depends on the hydroxyl value thereof and thus, resistance to chemicals and physical properties of a coated film containing the resin also depend on it.

The acrylpolyol resin can be synthesized by a known solution polymerization method, suspension polymerization method or emulsion polymerization method using a (meth) acrylate monomer, an unsaturated monomer having a carboxyl group, an unsaturated monomer having a hydroxyl group, and other ethylenically unsaturated monomers. Examples of the unsaturated monomer having a hydroxyl group include hydroxyethyl acrylate (HEA), hydroxypropyl acrylate (HPA), 2-hydroxyethyl methacrylate (HEMA), 2-hydroxypropyl methacrylate (HPMA), 2-hydroxybutyl monoacrylate (2-HBA), and 1,4-hydroxybutyl monoacrylate (1-HBA). Among them, 2-hydroxyethyl methacrylate is particularly preferred, since a monomer having a primary hydroxyl group can provide a coated film with better cracking resistance and durability.

The crosslinking agent is not particularly limited and can be appropriately selected depending on the purpose from conventionally known isocyanate compounds, amines, phenols, epoxy compounds, etc. In particular, isocyanate compounds are preferred.

The isocyanate compound is not particularly limited and can be appropriately selected from those known in the art depending on the purpose. Examples thereof include modified products (e.g., urethane-modified products, allophanate-modified products, isocyanurate-modified products, burette-modified products, carbodiimide-modified products and blocked isocyanates) of isocyanate monomers. Examples of the isocyanate monomer, which forms these modified products, include tolylene diisocyanate (TDI), 4,4'-diphenylmethane diisocyanate (MDI), xylylene diisocyanate (XDI), naphthylene diisocyanate (NDI), paraphenylene diisocyanate (PPDI), tetramethylxylylene diisocyanate (TMXDI), hexamethylene diisocyanate (HDI), dicyclohexylmethane diisocyanate (HMDI), isophorone diisocyanate (IPDI), lysine diisocyanate (LDI), isopropylidene bis(4-cyclohexylisocyanate) (IPC), cyclohexyl diisocyanate (CHDI) and tolidine diisocyanate (TODI).

Also, a catalyst may be used as a crosslinking accelerator in crosslinking reaction. Examples of the crosslinking accelerator include tertiary amines (e.g., 1,4-diaza-bicyclo[2.2.2]octane) and metal compounds (e.g., organotin compound). All the crosslinking agent added do not need to participate in the crosslinking reaction. In other words, an unreacted crosslinking agent may exist in the reaction system. Since this type of the crosslinking reaction proceeds with time, the presence of the unreacted crosslinking agent does not indicate that the crosslinking reaction does not proceed at all. Even if the unreacted crosslinking agent is detected, it does not mean that a crosslinked resin is absent. It can be confirmed by immersing the formed coated film in a solvent having high solubility whether or not the polymer is in a crosslinked state or non-crosslinked state. The polymer in a non-crosslinked state begins to dissolve in the solvent and does not remain as a solute, and therefore the presence or absence of a polymer structure of the solute may be analyzed. If the presence of the polymer structure is not confirmed in the solute, it is believed that the polymer is in a non-crosslinked state, making it possible to distinguish it from the polymer in a crosslinked state. The crosslinking degree can be expressed by a gel fraction.

The gel fraction refers to a ratio of a gel produced when resin (solute) is lack of independent mobility by the interaction in a solvent to produce an aggregated and solidified state (gel). The gel fraction of the resin is preferably 30% or higher, more preferably 50% or higher, still more preferably 70% or higher, particularly preferably 80% or higher. When the gel fraction is low, the formed reversible thermosensitive recording medium tends to degrade in its durability after repetitive use. Thus, the gel fraction is increased by mixing the resin with a resin curable through application of, for example, heat, ultraviolet (UV) ray and electron beam (EB); or by crosslinking the resin itself.

The gel fraction is measured in the following manner. Specifically, a film is separated from a support, followed by weighing for the film (initial mass). Then, the film is interposed between 400-mesh wire gauzes and immersed in a solvent capable of dissolving uncrosslinked resin for 24 hours, followed by drying in vacuum and weighing (mass after drying).

From the obtained values, the gel faction can be calculated using the following Equation 1.

$$\text{Gel fraction (\%)} = (\text{mass after drying (g)})/(\text{initial mass (g)}) \times 100 \qquad \text{<Equation 1>}$$

Notably, the mass of other components than the resin (e.g., particles of organic low-molecular-weight compounds), which are contained in the reversible thermosensitive recording layer, is not taken into account for calculation. When the mass of particles of organic low-molecular-weight compounds is not previously obtained, it may be calculated from a mass ratio of the resin to the particles of organic low-molecular-weight compounds. The mass ratio can be determined based on their specific gravities and a ratio of an area occupied with the resin to that occupied with the particles of organic low-molecular-weight compounds by observing a unit area of the cross section of the layer through transmission electron microscopy (TEM), scanning electron microscopy (SEM), etc.

In measurement for the gel fraction of a sample in which a reversible thermosensitive recording layer is formed on a support and other layers (e.g., a protective layer) are formed on the reversible thermosensitive recording layer; or a sample in which other layers are formed between a support and a reversible thermosensitive recording layer, first, the thicknesses of the reversible thermosensitive recording layer and the other layers are measured by observing its cross-section through transmission electron microscopy (TEM), scanning electron microscopy (SEM), etc., and then a surface portion corresponding to the thickness of the other layers is scraped to expose the surface of the reversible thermosensitive recording layer. Thereafter, the reversible thermosensitive recording layer is peeled off and the gel fraction thereof is measured similar to the above.

In measurement for the gel fraction of a sample in which a protective layer made of an ultraviolet curable resin is formed on the thermosensitive recording layer, an undesirable influence on the gel fraction must be prevented by scraping a surface portion corresponding to the protective layer and scraping a small portion of the thermosensitive recording layer surface so as to prevent contamination of the protective layer to the greatest extent possible.

The filler can be roughly classified into inorganic fillers and organic fillers.

Examples of the inorganic filler include calcium carbonate, magnesium carbonate, silicic acid anhydride, alumina, iron oxide, calcium oxide, magnesium oxide, chromium oxide, manganese oxide, silica, talc and mica.

Examples of the organic filler include silicone resins, cellulose resins, epoxy resins, nylon resins, phenol resins, polyurethane resins; urea resins, melamine resins, polyester resins, polycarbonate resins, styrene resins (e.g., polystyrene resins, styrene-isoprene copolymers, and styrene-vinylbenzene copolymers), acrylic resins (e.g., vinylidene chloride-acryl, acrylurethane and ethyleneacryl), polyethylene resins, formaldehyde resins (e.g., benzoguanamine formaldehyde and melamine formaldehyde), polymethyl methacrylate resins and polyvinyl chloride resins.

These may be used alone or in combination. When these fillers are used in combination, a combination of an inorganic filler and an organic filler is not particularly limited. The shape of the filler is spherical, granular, tabular and needle shapes.

In general, the amount of the filler added is preferably 5% by volume to 50% by volume.

The lubricant is not particularly limited and can be appropriately selected from those known in the art depending on the purpose. Examples thereof include synthetic waxes such as ester waxes, paraffin waxes and polyethylene waxes; vegetable waxes such as hardened castor oil; animal waxes such as hardened tallow; higher alcohols such as stearyl alcohol and behenyl alcohol; higher fatty acids such as margaric acid, lauric acid, myristic acid, palmitic acid, stearic acid and behenic acid; higher fatty acid esters such as sorbitan fatty acid esters; and amides such as stearic acid amides, oleic acid amides, lauric acid amides, ethylenebisstearamides, methylenebisstearamides and methylolstearamides.

The amount of the lubricant incorporated into the reversible thermosensitive recording layer is preferably 0.1% by volume to 95% by volume, more preferably 1% by volume to 75% by volume.

The surfactant is not particularly limited and can be appropriately selected depending on the purpose. Examples thereof include anionic surfactants, cationic surfactants, nonionic surfactant and amphoteric surfactants.

The plasticizer is not particularly limited and can be appropriately selected depending on the purpose. Examples thereof include phosphate esters, fatty acid esters, phthalate esters, dibasic acid esters, glycols, polyester plasticizers and epoxy plasticizers.

The method for forming the reversible thermosensitive recording layer is not particularly limited and can be appropriately selected depending on the purpose. Preferred examples thereof include (1) a method in which a support is coated with a reversible thermosensitive recording layer-coating liquid prepared by dissolving or dispersing in a solvent the binder resin, the electron-donating color-developing compound and the electron-accepting compound, and then the solvent is evaporated to form a sheet in parallel with or before crosslinking; (2) a method in which only the binder resin is dissolved in a solvent, then the electron-donating color-developing compound and the electron-accepting compound are dispersed in the resultant solution to prepare a reversible thermosensitive recording layer-coating liquid, then the thus-prepared coating liquid is applied onto a support, and then the solvent is evaporated to form a sheet in parallel with or before crosslinking; and (3) a method in which the binder resin, the electron-donating color-developing compound and the electron-accepting compound are mixed with one another through melting without using a solvent, and then the thus-molten mixture is formed into a sheet, followed by cooling and crosslinking. In these methods, it is also possible to form the coating liquid into a sheet-shaped reversible thermosensitive recording medium without using a support.

The solvent used in the method (1) or (2) varies depending on the types of the binder resin, the electron-donating color-developing compound and the electron-accepting compound and can not be determined depending on a single factor. Examples thereof include tetrahydrofuran, methyl ethyl ketone, methyl isobutyl ketone, chloroform, carbon tetrachloride, ethanol, toluene and benzene. The electron-accepting compound is dispersed in the form of particles in the reversible thermosensitive recording layer.

Also, in order for the reversible thermosensitive recording layer-coating liquid to exhibit high performances suited for a coating material, various pigments, defoamers, pigments, dispersants, slipping agents, antiseptics, crosslinking agents and plasticizers may be added thereto.

The method for applying the reversible thermosensitive recording layer-coating liquid is not particularly limited and can be appropriately selected depending on the purpose. For example, while a roll-shaped support is continuously conveyed, the coating liquid is applied on the support by known coating methods such as blade coating, wire bar coating, spray coating, air knife coating, bead coating, curtain coating, gravure coating, kiss coating, reverse roll coating, dip coating and die coating. Alternatively, a support is previously cut into sheets, and then while the sheets are conveyed, the coating liquid is applied on the sheets by the above coating method.

The drying conditions for the reversible thermosensitive recording layer-coating liquid are not particularly limited and can be appropriately determined depending on the purpose. For example, the coating liquid is dried at room temperature to 140° C. for about 10 min to about 1 hour.

The resin in the reversible thermosensitive recording layer can be cured through heating, ultraviolet irradiation, or electron beam irradiation.

The ultraviolet irradiation may be performed by any known ultraviolet irradiation devices, and examples thereof include those equipped with a light source, a lighting fixture, a power supply, a cooling device, and/or a transfer device.

Examples of the light source include mercury lamps, metal halide lamps, gallium lamps, mercury-xenon lamps and flash lamps. The wavelength of the light source can be appropriately selected in consideration of an ultraviolet absorption wavelength of a photopolymerization initiator and a photopolymerization accelerator, which are added to a composition for a reversible thermosensitive recording medium.

The irradiation conditions of an ultraviolet ray are not particularly limited and can be appropriately selected depending on the purpose. For example, the transfer speed and the output of a lamp may be determined in consideration of the required irradiation energy for crosslinking of the resin.

The electron beam irradiation can be performed using known electron beam irradiation devices. The electron beam irradiation devices can be roughly classified into scanning (scanbeam)-type devices and non-scanning (areabeam)-type devices. The irradiation conditions can be determined according to, for example, the irradiation area and irradiation dose. Also, the irradiation dose of the electron beam can be determined from the following Equation 2 in consideration of the irradiation dose required for crosslinking the resin, the electron current, the irradiation width and the transfer speed.

<Equation 2>

$$D=(\Delta E/\Delta R)\cdot\eta\cdot I/(W\cdot V)$$

where D denotes a required irradiation dose (Mrad), ΔE/ΔR denotes an average energy loss, η denotes an efficiency, I denotes an electron current (mA), W denotes an irradiation width (cm), and V denotes a transfer speed (cm/s).

From an industrial point of view, the following Equation 3 obtained by simplifying Equation 2 is preferably used.

<Equation 3>

$$D\cdot V=K\cdot I/W$$

Here, a device rating is shown by Mrad·m/min, and about 20 mA to about 500 mA is selected as an electron current rating.

The thickness of the reversible thermosensitive recording layer is not particularly limited and can be appropriately selected depending on the purpose. For example, it is 1 μm to 20 μm, more preferably 3 μm to 15 μm.

When the thickness of the reversible thermosensitive recording layer is too small, the density of developed color decreases and thus, image contrast of the formed image may be lower. Whereas when the thickness of the reversible thermosensitive recording layer is too large, thermal distribution is broad in the layer. Thus, some portions do not reach a color developing temperature and cannot develop color, potentially resulting in failure to attain an intended color density.

<Gas Barrier Layer>

The gas barrier layer contains an inorganic layered compound and, as a binder resin, at least one selected from a polyvinyl alcohol polymer and an ethylene-vinyl alcohol polymer; and, if necessary, further contains other components.

The gas barrier layer prevents gas permeation by virtue of hydrogen bonding ability of hydroxyl groups contained in the binder resin. However, the binder resin containing in the molecule a hydroxyl group exhibits high water absorbability and thus, the gas barrier layer is degraded in gas barrier performance at high humidity conditions. Incorporation of an inorganic layered compound into the gas barrier layer increases the length of a gas passageway to prevent gas permeation, whereby an electron-donating color-developing compound contained in the reversible thermosensitive recording layer can be prevented from decomposition through oxidation.

Preferred examples of the binder resin include polyvinyl alcohol polymers. Examples of the polyvinyl alcohol polymer include polyvinyl alcohols, derivatives thereof and modified products thereof. These may be used alone or in combination.

The polyvinyl alcohol polymer preferably has a polymerization degree of 100 to 5,000, more preferably 500 to 3,000.

Also, the polyvinyl alcohol polymer preferably has a saponification degree of 60 mol % or higher, more preferably 75 mol % or higher.

Examples of the polyvinyl alcohol derivative include polyvinyl alcohol derivatives in which about 40 mol % of the hydroxyl groups are acetalized. Examples of the polyvinyl alcohol-modified product include polyvinyl alcohol-modified products obtained through copolymerization of carboxyl group-containing monomers, amino group-containing monomers, etc.

Polyvinyl alcohol polymers are advantageous in that they have very high gas barrier performance under dry conditions. However, under high humidity conditions, polyvinyl alcohol polymers are degraded in their gas barrier property more considerably than ethylene-vinyl alcohol copolymers. Thus, when a gas barrier layer containing a polyvinyl alcohol polymer is used under high humidity conditions, a coating liquid therefor preferably contains a larger amount of an inorganic layered compound described below.

Examples of the ethylene-vinyl alcohol copolymer which can be used include products obtained by saponifying an ethylene-vinyl acetate copolymer.

Specific examples of the product obtained by saponifying an ethylene-vinyl acetate copolymer include compounds obtained by saponifying an ethylene-vinyl acetate copolymer (i.e., copolymerized product between ethylene and vinyl acetate) and compounds obtained by saponifying an ethylene-vinyl acetate-based copolymers (i.e., copolymerized product among ethylene, vinyl acetate and other monomer(s)).

In materials used for forming the gas barrier layer, it is preferred that ethylene account for 20 mol % to 60 mol % of all monomers to be copolymerized for forming an ethylene-vinyl acetate-based copolymer. When ethylene accounts for lower than 20 mol % of the all monomers, gas barrier performance of the formed gas barrier layer degrades at high humidity. Whereas when ethylene accounts for higher than 60 mol % of the all monomers, gas barrier performance of the formed gas barrier layer tends to degrade.

In the ethylene-vinyl acetate-based copolymer, the saponification degree of the vinyl acetate component is preferably 95 mol % or more. When the saponification degree is less than 95 mol %, the formed gas barrier layer tends to exhibit insufficient gas barrier performance and oil resistance. Also, the ethylene-vinyl acetate-based copolymer is preferably reduced in molecular weight through treatment with a peroxide or the like, from the viewpoint of attaining more stable dissolution stability in a solvent.

The solvent which can be used for preparing a gas barrier layer composition may be aqueous or non-aqueous solvents capable of dissolving polyvinyl alcohol polymers and/or ethylene-vinyl alcohol-based copolymers. Preferably, water giving low harmful effects to the environment is used, since the gas barrier layer composition contains a polyvinyl alcohol polymer as a gas barrier resin (binder resin).

Also, when an ethylene-vinyl alcohol copolymer is used as a binder resin, it is preferred that a gas barrier composition be prepared using a solvent mixture of water and a lower alcohol, and a end-modified ethylene-vinyl alcohol-based copolymer which has been reduced in molecular weight through treatment with a peroxide or the like. The solvent mixture is preferably a mixture containing 50% by mass to 85% by mass of water and 15% by mass to 50% by mass of at least one lower alcohol selected from ethyl alcohol, n-propyl alcohol, iso-propyl alcohol, n-butyl alcohol, iso-butyl alcohol, sec-butyl alcohol and tert-butyl alcohol, since the ethylene-vinyl alcohol-based copolymer can dissolve therein to an appropriate level, and the solid content of the resultant mixture can be appropriately maintained. When the lower alcohol content of the solvent mixture is more than 50% by mass, the below-described inorganic layered compound is insufficiently cleaved during dispersion. Notably, among lower alcohols having 2 to 4 carbon atoms, n-propyl alcohol and iso-propyl alcohol are preferred.

—Inorganic Layered Compound—

The inorganic layered compound is not particularly limited. Inorganic layered compounds which are swollen and cleaved in a dispersion medium are preferably used. Examples thereof include kaolinite-group minerals having a 1:1 phyllosilicate structure, antigorite-group minerals belonging to the serpentine group, smectite-group minerals, vermiculite-group minerals (hydrous silicate minerals) and mica-group minerals.

Specific examples include kaolinite, nacrite, dickite, halloysite, hydrated halloysite, antigorite, chrysotile, pyrophyllite, montmorillonite, beidellite, saponite, hectorite, sauconite, stevensite, tetrasilicic mica, sodium tainiolite, muscovite, margarite, talc, vermiculite, phologopite, xanthophyllite and chlorite. These may be naturally-occurring or synthetic products. In addition, scale-like silica and the like may also be used. These may be used alone or in combination. Among them, montmorillonite is particularly preferred, since a gas barrier layer exhibiting good gas barrier performance can be obtained from a gas barrier layer-coating composition containing it.

The naturally-occurring inorganic layered compound has a relatively large size after dispersed in the binder resin. Thus, when it is used, desired gas barrier performance is easily obtained. However, inorganic metal ions contained as an impurity therein in a trace amount are degraded through oxidation caused by thermal energy applied during image formation of a recording medium of the present invention, undesirably causing formation of a colored component. As a result, when the image formed on the recording medium of the present invention is erased, the colored component can be viewed after erasure and thus, the image quality is considerably impaired. In order to overcome this problem, preferably, an alkali metal or an alkaline earth metal is added to a mixture of a naturally-occurring inorganic layered compound and a gas barrier resin to prevent degradation through oxidation caused by inorganic metal ions (impurities).

The synthetic inorganic layered compound contains no impurities (i.e., inorganic metal ions) and does not cause degradation of the formed image quality. However, the synthetic inorganic layered compound has a small particle diameter. As a result, use of it shortens the length of a gas passageway and thus, desired gas barrier performance may not be obtained.

In the present invention, a naturally-occurring inorganic layered compound or a synthetic inorganic layered compound may be used. In order to attain preferred gas barrier performance, the mixing ratio of a binder resin used to an inorganic layered compound used is determined in consideration of the above description in relation to properties of the naturally-occurring inorganic layered compound and the synthetic inorganic layered compound.

In the gas barrier layer, the mass ratio (on a solid basis) of the binder resin to the inorganic layered compound is preferably 30:70 to 99:1, more preferably 30:70 to 50:50. When the amount of the inorganic layered compound used is small, sufficient gas barrier performance cannot be attained. When the amount of the inorganic layered compound used is too large, the formed gas barrier layer is decreased in strength and adhesiveness to other layers. It is also reduced in transparency, potentially giving adverse effects to an image formed through thermosensitive recording.

The gas barrier layer containing the inorganic layered compound, which is formed from a composition therefor, is preferably improved in adhesiveness to adjacent layers. In order that formation/erasure of an image can be performed many times on the reversible thermosensitive recording medium of the present invention, one or more modifiers (e.g., a silane coupling agent, a titanium coupling agent, an isocyanate compound and an aziridine compound) may be optionally incorporated into the gas barrier layer.

Examples of the silane coupling agent include vinyl group-containing alkoxysilanes such as vinyltrimethoxysilane, vinyltriethoxysilane, N-β-(N-vinylbenzylaminoethyl)-γ-aminopropyltrimethoxysilane, vinyltriacetoxysilane and 3-propyltrimethoxysilane methacrylate; epoxy group-containing alkoxysilanes such as 3-glycidoxypropyltrimethoxysilane, 3-glycidoxypropylmethyldimethoxysilane and 2-(3,4-epoxycyclohexyl)ethyltrimethoxysilane; amino group- and/or imino group-containing alkoxysilanes such as 3-aminopropyltriethoxysilane, 3-N-(2-aminoethyl)aminopropyltrimethoxysilane and 3-N-(2-aminoethyl)aminopropylmethyldimethoxysilane; isocyanate alkoxysilanes such as triethoxysilylpropyl isocyanate; mercapto group-containing alkoxysilanes such as γ-mercaptopropyltrimethoxysilane; and ureido group-containing alkoxysilanes such as γ-ureidopropyltriethoxysilane. Among the compounds specifically shown above, amino group-containing trialkoxysilane compounds and mercapto group-containing trialkoxysilane compounds are preferred, since they rapidly react with organic residues adjacent to the gas barrier layer. Furthermore, amino group-containing trimethoxysilane compounds and mercapto group-containing trimethoxysilane compounds are more preferred, since they rapidly react with inorganic layered compounds contained in the gas barrier layer.

Examples of the aziridine compound include trimethylolpropane tris(3-aziridinyl propionate), trimethylolpropane tris [3-(2-methyl-aziridinyl)-propionate], trimethylolpropane tris(2-aziridinyl butyrate), tris(1-aziridinyl)phosphine oxide, pentaerythritol tris-3-(1-aziridinyl propionate), pentaerythritol tetrakis-3-(1-aziridinyl propionate) and 1,6-bis(1-aziridinocarbamoyl)hexamethylenediamine.

Examples of the isocyanate compound include aliphatic or alicyclic diisocyanates such as hydrogenated TDI, hydrogenated XDI, hydrogenated MDI, hexamethylene diisocyanate (HDI), isophorone diisocyanate (IPDI) and xylylene diisocyanate (XDI); tri- or higher functional polyisocyanates of burette type, isocyanurate type, adduct type, etc., which are derivatives of aliphatic and alicyclic diisocyanates; aliphatic isocyanate compounds such as isocyanate-containing oligomers and isocyanate-containing polymers; aromatic diisocyanates such as phenylene diisocyanate (PDI), toluene diisocyanate (TDI), naphthalene diisocyanate (NDI) and 4,4'-diisocyanate diphenylmethane (MDI); tri- or higher functional polyisocyanates of burette type, isocyanurate type, adduct type, etc., which are derivatives of aromatic diisocyanates; and aromatic isocyanate compounds such as isocyanate-containing oligomers and isocyanate-containing polymers.

The gas barrier layer composition generally contains, as a solvent, water for dissolving an aqueous polymer. In formation of the gas barrier layer, preferably, the isocyanate compound does not react with water, and is cured after coating of the composition. Thus, preferred are self-emulsified polyisocyanate compounds which are dispersed in water and which are produced by introducing a hydrophilic group into the skeleton of isocyanate compounds. Isocyanate compounds having a hydrophobic group are prevented from reacting with water before coating of the composition, which is preferred.

Similar to the isocyanate compound, the carbodiimide compound is preferably a water-dispersible emulsified compound. Preferred are carbodiimide compounds which are modified so as to have hydrophilicity as follows: a urethanization reaction between an isocyanato-end carbodiimide compound and a polyol compound is performed for chain elongation; and then the product is modified at its end with a hydrophilic oligomer so as to have hydrophilicity. This is because they exhibit desired stability and desired crosslinking property.

The gas barrier layer-coating liquid is prepared from the above components by, for example, the following methods: (1) a method in which a binder resin is dissolved in the above solvent; an inorganic layered compound (which may be previously swollen and cleaved in a dispersion medium such as water) is added to/mixed with the resultant solution; and the inorganic layered compound is dispersed using an agitator, a disperser, etc.; and (2) a method in which an inorganic layered compound is swollen and cleaved in a dispersion medium such as water, followed by further cleavage of the inorganic layered compound using an agitator, a disperser, etc.; and a solution prepared by dissolving a binder resin in the above solvent is added to/mixed with the resultant dispersion (solution). In these methods, when a naturally-occurring inorganic layered compound is used, a compound containing an alkali metal ion or alkaline earth metal ion (e.g., magnesium hydroxide and calcium hydroxide) is added to the mixture.

The agitator and disperser are not particularly limited and commonly-used agitators and dispersers may be used. Use of them enables the inorganic layered compound to be uniformly dispersed in the dispersion. In particular, high-pressure dispersers, ultrasonic dispersers, etc. are preferably used, since a transparent, stable inorganic layered compound dispersion can be prepared. Examples is of the high-pressure disperser include NANOMIZER (trade name, manufactured by Nanomizer Co., Ltd.), MICROFLUIDIZER (trade name, manufactured by Microfluidics), ALTIMIZER (trade name, manufactured by Sugino Machine Limited), DEBEE (trade name, manufactured by BEE International, Inc.) and NIRO SOAVI HOMOGENIZER (trade name, manufactured by Niro Soavi). These high-pressure dispersers are preferably used at 1 MPa to 100 MPa to perform a dispersion treatment. When the pressure is higher than 100 MPa, the inorganic layered compound is easily pulverized, resulting in shortening the length of a gas passageway. As a result, a desired gas barrier-property may not be obtained. When the pressure is lower than 1 MPa, the inorganic layered compound is not sufficiently dispersed or a time-consuming dispersion treatment must be performed, which is not preferred.

The silane coupling agent, isocyanate compound, aziridine compound and carbodiimide compound, which are used for enhancing adhesiveness of the gas barrier layer to adjacent layers, are preferably added to a dispersion of the binder resin and the inorganic layered compound.

In order to enhance adhesiveness of the gas barrier layer to adjacent layers, the gas barrier layer is preferably made to adhere to adjacent layers via an adhesive layer (primer layer) formed of any of an adhesive or anchor coat agent. Examples of the adhesive include those used for lamination, such as isocyanate-based adhesives, urethane-based adhesives and acrylic-based adhesives. Examples of the anchor coat agent include those used for lamination, such as titanium-based anchor coat agents, isocyanate-based anchor coat agents, imine-based anchor coat agents and polybutadiene-based anchor coat agents. Also, these adhesives and anchor coat agents may contain materials for improving adhesiveness (e.g., a cross-linking agent).

Next will be described a method for forming the gas barrier layer and the optionally provided primer layer from the above materials.

For forming the gas barrier layer on the reversible thermosensitive recording layer, a gas barrier layer composition is applied onto the reversible thermosensitive recording layer whose surface has optionally been coated with an adhesive or anchor coat agent, followed by drying under heating. The coating method for the gas barrier layer composition may be a commonly-used coating method such as roll coating using a gravure cylinder or the like, the doctor knife method, air knife-nozzle coating, bar coating, spray coating and dip coating. These may be used in combination.

The gas barrier layer preferably has a thickness of 0.1 μm to 5 μm. More preferably, the thickness is 0.1 μm to 0.5 μm, from the viewpoint of forming a gas barrier layer having high transparency. When the thickness is small than 0.1 μm, the formed gas barrier layer may not exhibit desired gas barrier performance and desired property of preventing permeation of an organic solvent. When the thickness is more than 5 μm, gas barrier performance cannot be improved and the formed gas barrier layer may not have sufficient transparency.

<Support>

The shape, structure and size of the support are not particularly limited and can be appropriately determined depending on the purpose. For example, the support has a tabular shape. It may have a single-layer structure or a multi-layer structure. The size thereof can be appropriately determined in consideration of, for example, the size of the reversible thermosensitive recording medium.

Examples of the material for the support include inorganic materials and organic materials. Examples of the inorganic material include glass, quartz, silicone, silicon oxide, aluminum oxide, $SiO_2$ and metals. Examples of the organic material include paper, cellulose derivatives (e.g., cellulose triacetate), synthetic paper polyethylene terephthalates, polycarbonates, polystyrenes and polymethyl methacrylates. These may be used alone or in combination.

In particular, polyethylene terephthalates and PET-G films each having a Haze as measured according to JIS K7105 of 10% or less are preferably used as a support for the purpose of forming a sheet providing a high clear image.

In order for the support to have improved adhesiveness to a layer coated thereon, it is preferably subjected to surface modification by, for example, a corona discharge treatment, an oxidation treatment (using, for example, chromic acid), an etching treatment, an easy-adhesion treatment and an antistatic treatment. The support is preferably whitened by incorporating a white pigment (e.g., titanium oxide) thereinto.

The thickness of the support is not particularly limited and can be appropriately selected depending on the purpose. Preferably, it is 10 μm to 2,000 μm, more preferably 20 μm to 1,000 μm.

The support may have a magnetic reversible thermosensitive recording layer on at least a surface over which the reversible thermosensitive recording layer is formed and a surface over which no reversible thermosensitive recording layer is formed. The reversible thermosensitive recording medium of the present invention can be attached to other media via, for example, an adhesive layer.

<Undercoat Layer>

The undercoat layer is provided between the reversible thermosensitive recording layer and the support, in order for the formed medium to have a higher sensitivity; i.e., to effectively utilize heat applied, in order to improve adhesiveness between the support and the reversible thermosensitive recording layer, and in order to prevent materials contained in the reversible thermosensitive recording layer from penetrating into the support. The undercoat layer contains at least hollow particles and a binder resin and, if necessary, further contains other components.

Examples of the hollow particles include single-hollow particles in which one hollow portion is present in each particle, and multi-hollow particles in which a lot of hollow portions are present in each particle. These may be used alone or in combination.

The material for forming the hollow particles is not particularly limited and can be appropriately selected depending on the purpose. Preferred examples thereof include thermoplastic resins. The hollow particles may be appropriately synthesized or may be commercially available. Examples of commercially available products thereof include MICROSPHERE R-300 (product of Matsumoto Yushi-Seiyaku Co., Ltd.), ROPAQUE HP1055 and ROPAQUE HP433J (these products are of Zeon Corporation) and SX866 (product of JSR Corporation).

The amount of the hollow particles incorporated into the undercoat layer is not particularly limited and can be appropriately selected depending on the purpose. For example, it is preferably 10% by mass to 80% by mass.

The binder resin may be the same resins as used in the reversible thermosensitive recording layer or the layer containing a polymer having a UV ray absorbing structure.

In addition, an undercoat layer may contain at least one of various organic fillers and inorganic fillers such as calcium carbonate, magnesium carbonate, titanium oxide, silicon oxide, aluminum hydroxide, kaolin and talc.

Notably, the undercoat layer may contain a lubricant, a surfactant, a dispersant and other agents.

The thickness of the undercoat layer is not particularly limited and can be appropriately selected depending on the purpose. It is preferably 0.1 μm to 20 μm, more preferably 0.5 μm to 5 μm.

<Protective Layer>

The protective layer contains a binder resin, a releasing agent and a UV ray absorber; and, if necessary, further contains other components.

The binder resin may be the same resins as used in the reversible thermosensitive recording layer or the layer containing a polymer having a UV ray absorbing structure. In particular, preferred are resins curable with, for example, heat, UV ray and electron beam, with thermosetting resins and UV curable resins being more preferred, with UV curable resins being particularly preferred.

Examples of the releasing agent include silicones having a polymerizable group, silicone-grafted polymer, waxes, zinc stearate and silicone oil.

The amount of the releasing agent used is preferably 0.01% by mass to 50% by mass, more preferably 0.1% by mass to 40% by mass, based on the total mass of the resin component of the protective layer. Although the releasing agent exhibits its effect even in a small amount, the effect commensurate with the addition cannot be obtained when the amount thereof is less than 0.01% by mass. Whereas when the amount thereof exceeds 50% by mass, adhesiveness of the protective layer to a layer provided thereunder may be problematically degraded.

The UV ray absorber may be the same as those used in a layer containing a polymer having a UV ray absorbing structure. Among them, organic UV ray absorbers are particularly preferred. The amount of the UV ray absorber added is preferably 0.5% by mass to 10% by mass based on the total mass of the resin component of the protective layer.

Examples of the other components include conventionally known additives such as surfactants, leveling agents and antistatic agents.

A solvent used for preparing a protective layer-coating liquid, a disperser for the coating liquid, a coating method for forming the protective layer, a drying method, a curing method etc. may be the solvent, disperser and known methods used in formation of the reversible thermosensitive recording layer.

The thickness of the protective layer is preferably 0.1 μm to 20 μm, more preferably 0.5 μm to 10 μm, still more preferably 1.5 μm to 6 μm. When the thickness is less than 0.1 μm, the protective layer is broken when erasing and printing of recorded images are repeatedly performed, resulting in that sufficient durability is not attained. In addition, the protective layer having such a thickness may be easily attacked by a chemical, potentially allowing the reversible thermosensitive recording medium to lose its intrinsic function. Whereas when the thickness is more than 20 μm, only blurred images having poor dot reproducibility (definition of printed image) can be obtained. Furthermore, energy required for printing and erasing may increase due to poor thermal conductivity, leading to increase of load on the devices used.

The shape of the reversible thermosensitive recording medium of the present invention is not particularly limited. It can be formed into any shape according to the applications, and is formed into, for example, a card, sheet, label or roll.

The card-shaped medium is used as, for example, a prepaid card, a point card and a credit card. The sheet-shaped medium having a general document size (e.g. A4 size) can be used for trial printing with a printing/erasing device. Also, the sheet-shaped medium having a sheet size larger than a card size can be widely used for forming a temporarily used document, since printing is performed in a wider area. Specifically, it can be used as, for example, a general document, an instruction for process management, a circulating document and a material for conference.

The roll-shaped medium can be used as a display board, a notice board and an electronic blackboard, with being mounted to a device equipped with a printing/erasing section. Such a display device is preferably used in a clean room without dusts and contaminants.

In the reversible thermosensitive recording medium of the present invention, an irreversible thermosensitive recording layer may be used in combination. In this case, developed color tones of the reversible and irreversible thermosensitive recording layers may be the same or different. Also, in the reversible thermosensitive recording medium, a portion or the entire of the reversible thermosensitive recording layer surface facing opposite to the support, or a portion of the reversible thermosensitive recording layer surface facing the support may be provided with a colored layer capable of irreversibly showing information (e.g., any patterns) through, for example, offset printing and gravure printing, or through printing using an inkjet printer, a thermal transfer printer, a sublimation-type printer, etc. Furthermore, an OP varnish layer made mainly of a curable resin may be provided on a portion or the entire of the colored layer. Examples of the pattern formed include characters, figures, designs, photographs, and information detected with an infrared ray. Alternatively, a dye or pigment can be incorporated into any of the constituent layers for coloring.

Furthermore, the reversible thermosensitive recording medium of the present invention can be provided with a hologram for security. It can also be provided with a design (e.g., human images, company marks and symbol marks) as a relief or intaglio irregularities so as to impart design properties thereto.

Image formation/erasure for the reversible thermosensitive recording medium can be performed using a known image processing apparatus.

Preferred examples of the image processing apparatus include those including an image forming unit configured to form images on a reversible thermosensitive recording medium, and an image erasing unit configured to erase the formed images. In particular, from the viewpoint of shortening the processing time, preferred are image processing apparatuses including an image forming/erasing unit configured to serve both as an image forming unit and as an image erasing unit. Specific examples thereof include (1) image processing apparatuses in which an image can be processed by changing the level of energy applied to a thermal head; (2) image processing apparatuses whose image forming unit is a thermal head and whose image erasing unit is selected from press-contact type units configured to bond a heating element (e.g., a thermal head, a ceramic heater (i.e., a heating element produced by screen-printing a heat element on an alumina support), a hot stamp, a heat roller and a heat block) and non-contact type units using warm air, an infrared ray, a laser beam, etc.; and (3) image processing apparatuses in which an image can be processed by changing the level of energy applied with a non-contact mode using a laser beam, the image forming unit is a non-contact mode using, for example, a laser beam, and the image erasing unit is selected from press-contact type units configured to bond a heating element (e.g., a thermal head, a ceramic heater (i.e., a heating element produced by screen-printing a heat element on an alumina support), a hot stamp, a heat roller and a heat block) and non-contact type units using warm air, an infrared ray, a laser beam, etc.

EXAMPLES

The present invention will next be described by way of examples, which should not be construed as limiting the present invention thereto.

Synthesis Example 1

Synthesis of Compound (A-21)

<Preparation of Diazonium Salt>

A 1 L-beaker equipped with a thermometer was charged with 3-amino-4-chlorobenzoic acid (25.0 g), 32% hydrochloric acid (400 g) and distilled water (250 g), followed by stirring under reflux. The reaction mixture was heated for 30 min until dissolution of the aminobenzoic acid serving as a starting material was confirmed. After termination of heating, the internal temperature was cooled to −5° C. After cooling, an aqueous sodium nitrite solution (sodium nitrite (11.7 g)/distilled water (18.0 g)) was added dropwise to the resultant mixture so that the internal temperature did not exceed 0° C. After completion of dropwise addition, the reaction mixture was stirred at the same temperature for 15 min, to thereby prepare aqueous diazonium salt solution (A) of interest.

<Diazo Coupling Reaction>

A 3 L-beaker equipped with a thermometer was charged with 4-hydroxyphenetol (23.15 g), pellets of sodium hydroxide (6.7 g) and methanol (375 mL), followed by stirring for dissolution at room temperature. Subsequently, a 30% aqueous sodium hydroxide solution (375 mL) was added to the resultant mixture, and then the internal temperature was cooled to −5° C. After cooling, aqueous diazonium salt solution (A) was gradually added to the mixture so that the internal temperature did not exceed 0° C. After completion of dropwise addition, the reaction mixture was further stirred for 1 hour under cooling. After removal of the coolant used, the reaction mixture was further stirred for 1 hour, and then completion of reaction was confirmed through TLC. After completion of reaction, concentrated hydrochloric acid was carefully added to the reaction mixture under stirring to adjust the pH to 1. The precipitated crystals were collected through filtration, and then the thus-obtained crude crystals were stirred three times using distilled water (500 mL) for washing. The thus-obtained crude crystals were recrystallized from isopropyl alcohol (IPA), to thereby produce 30 g of diazo compound (B) of interest as red-brown crystals (yield: 64%).

<Synthesis of Compound (A-21)>

A 300-mL three-necked flask equipped with a stirrer, a thermometer and a condenser was charged with diazo compound (B) (15.0 g), sodium azide (6.3 g) and N,N-dimethylformamide (DMF) (150 mL), followed by stirring with heating at an internal temperature of 140° C. for 6 hours. After disappearance of starting materials had been confirmed through TLC, 1N diluted hydrochloric acid was added to the resultant reaction mixture to adjust the pH of the reaction system to 3. The precipitated crystals were collected through filtration, and the thus-collected crystals were stirred twice under heating using distilled water (200 mL) for washing. The obtained crude crystals were recrystallized from IPA, to thereby produce 11.9 g of Compound (A-21) of interest (yield: 85%). The thus-produced compound was found to have a melting point of 254.1° C.

Synthesis Example 2

Synthesis of Compound (A-23)

A 100-mL three-necked flask equipped with a stirrer, a thermometer and a condenser was charged with Compound (A-21) (7.0 g), powder of sodium hydrogen carbonate (2.95 g), ethyl iodide (5.47 g) and N,N-dimethylacetamide (DMA) (70 mL), followed by stirring under heating in an oil bath (85° C.) for 2 hours. After disappearance of starting materials had been confirmed through TLC, 1N diluted hydrochloric acid was added to the reaction mixture. Thereafter, the resultant mixture was stirred with a stirring bar to precipitate crystals. The thus-obtained crystals were collected through filtration, and the thus-collected crystals were stirred twice under heating using distilled water (50 mL) for washing. The obtained crude crystals were recrystallized from IPA, to thereby produce 7.0 g of a compound of interest (yield: 91%). The thus-produced compound was found to have a melting point of 155.2° C. and a λmax (methylene chloride) of 350.5 nm.

Synthesis Example 3

Synthesis of Compound (F-1)

A 500-mL three-necked flask equipped with a stirrer, a thermometer and a condenser was charged with 2-[2-hydroxy-5-(1-hydroxyethyl)phenyl]-2H-benzotriazole (7.3 g), hexamethyltetramine (4.2 g) and trifluoromethanesulfonic acid (80 mL), followed by stirring under reflux for one day. After disappearance of starting materials had been confirmed through TLC, the reaction mixture was mixed with ice (200 g) and the resultant mixture was extracted twice with methylene chloride (50 mL). The methylene chloride layers were combined, and the thus-combined layer was washed sequentially with saturated sodium hydrogen carbonate and saturated brine. The formed organic layer was dried with sodium sulfate anhydrate. After removal of sodium sulfate anhydrate, the organic layer was dried with an evaporator to yield crude crystals. The obtained crude crystals were recrystallized from ethyl acetate, to thereby produce 7.0 g of Compound (F-1) of interest (yield: 86%). The thus-produced compound was found to have a λmax (methylene chloride) of 356.5 nm.

Synthesis Example 4

Synthesis of Compound (G-1)

A 100-mL three-necked flask equipped with a stirrer, a thermometer and a condenser was charged with Compound (G-1) (5.4 g), aniline (2.0 g), glacial acetic acid (1 drop) and ethanol (50 mL), followed by stirring under reflux for 1 hour. After disappearance of starting materials had been confirmed through TLC, the reaction mixture was cooled to room temperature to precipitate crystals. The thus-precipitated crystals were collected through filtration and recrystallized from ethanol, to thereby produce 5.5 g of Compound (G-1) of interest. The obtained compound was found to have λmax (methylene chloride) of 356.0 nm.

Synthesis Example 5

Synthesis of Compound (H-1)

A 1,000-mL three-necked flask equipped with a stirrer, a thermometer and a condenser was charged with the above-synthesized Compound (F-1) (50.0 g), sodium formate (19.4 g), 4-methoxyphenol (1.8 g) and formic acid (500 mL), followed by dissolution under stirring at an internal temperature of 30° C. After termination of heating, hydroxylamine hydrochloride (19.8 g) was added to the flask. The resultant mixture was refluxed under stirring for 6 hours, and then completion of reaction was confirmed through TLC. After completion of reaction, the reaction mixture was cooled to room temperature and was extracted twice with ethyl acetate (500 mL). The ethyl acetate layers were combined with each other, and the resultant mixture was washed sequentially with saturated sodium hydrogen carbonate and saturated brine. The obtained organic layer was dried with sodium sulfate anhydrate. After removal of sodium sulfate anhydrate through filtration, the organic layer was dried with an evaporator to yield crude crystals. The obtained crude crystals were recrystallized from isopropyl ether (IPE), to thereby produce 43.6 g of Compound (H-1) of interest (yield: 86%). The thus-produced compound was found to have a melting point of 153.5° C. and a λmax (chloroform) of 341.5 nm.

Synthesis Example 6

Synthesis of Compound (I-1)

A 500-mL eggplant-shaped flask was charged with the above-synthesized Compound (F-1) (12.7 g), acetophenone (8.1 g) and 30% aqueous sodium hydroxide solution (150 mL), followed by reaction for 6 hours using an ultrasonic apparatus. After disappearance of starting materials had been confirmed through TLC, 1N diluted hydrochloric acid was added to the reaction mixture so that the pH of the reaction system was adjusted to 1. The precipitated crystals were collected through filtration and then washed twice under stirring and heating with distilled water (500 mL). The obtained crude crystals were recrystallized from IPA, to thereby produce 11.8 g of Compound (I-1) of interest (yield: 68%). The thus-produced compound was found to have a melting point of 92.38° C. and a λmax (methylene chloride) of 346.5 nm.

Synthesis Example 7

Synthesis of Compound (A-16)

<Preparation of Diazonium Salt>

A 2 L-beaker equipped with a thermometer was charged with 3-amino-4-chlorobenzotrifluoride (25.0 g), 32% hydrochloric acid (110 g) and distilled water (500 g), followed by stirring under reflux. The reaction mixture was heated for 30 min until dissolution of the 3-amino-4-chlorobenzotrifluoride serving as a starting material was confirmed. After termination of heating, the internal temperature was cooled to −5° C. After cooling, an aqueous sodium nitrite solution (sodium nitrite (10.6 g)/distilled water (18.0 g)) was added dropwise to the resultant mixture so that the internal temperature did not exceed 0° C. After completion of dropwise addition, the reaction mixture was stirred at the same temperature for 15 min, to thereby prepare aqueous diazonium salt solution (C) of interest.

<Diazo Coupling Reaction>

A 3 L-beaker equipped with a thermometer was charged with 4-hydroxyphenetol (20.3 g), pellets of sodium hydroxide (5.9 g) and methanol (375 mL), followed by stirring for dissolution at room temperature. Subsequently, a 30% aqueous sodium hydroxide solution (375 mL) was added to the resultant mixture, and then the internal temperature was cooled to −5° C. After cooling, aqueous diazonium salt solution (C) was gradually added to the mixture so that the internal temperature did not exceed 0° C. After completion of dropwise addition, the reaction mixture was further stirred for 1 hour under cooling. After removal of the coolant used, the reaction mixture was further stirred for 1 hour, and then completion of reaction was confirmed through TLC. After completion of reaction, concentrated hydrochloric acid was carefully added to the reaction mixture under stirring to adjust the pH to 1. The precipitated crystals were collected through filtration, and then the thus-obtained crude crystals were stirred three times using distilled water (500 mL) for washing. The thus-obtained crude crystals were recrystallized from isopropyl alcohol (IPA), to thereby produce 30 g of diazo compound (D) of interest as red-brown crystals (yield: 70%).

<Cyclization Reaction>

A 300-mL three-necked flask equipped with a stirrer, a thermometer and a condenser was charged with diazo compound (D) (10.0 g), sodium azide (3.9 g) and N,N-dimethylformamide (DMF) (150 mL), followed by stirring under heating for 6 hours at an internal temperature of 140° C. After disappearance of starting materials had been confirmed through TLC, 1N diluted hydrochloric acid was added to the reaction mixture so that the pH of the reaction system was adjusted to 7. The resultant mixture was extracted twice with ethyl acetate (200 mL). The ethyl acetate layers were combined with each other, and the mixture was washed sequentially with saturated sodium hydrogen carbonate and saturated brine. The obtained organic layer was dried with sodium sulfate anhydrate. After removal of sodium sulfate anhydrate through filtration, the organic layer was dried with an evaporator. The residue was purified through silica gel column chromatography (tetrahydrofuran/hexane=15/1), to thereby produce 3.6 g of Compound (A-16) of interest (yield: 38%).

The thus-produced compound was found to have a melting point of 117.8° C. and a $\lambda_{max}$(methylene chloride) of 346.5 nm.

Synthesis Example 8

Synthesis of Compound (N-1)

<Preparation of Diazonium Salt>

A 2 L-beaker equipped with a thermometer was charged with 3-amino-2-chloropyridine (25.0 g), 32% hydrochloric acid (167 g) and distilled water (800 g), followed by stirring under reflux. The reaction mixture was heated for 30 min until dissolution of the 3-amino-2-chloropyridine serving as a starting material was confirmed. After termination of heating, the internal temperature was cooled to −5° C. After cooling, an aqueous sodium nitrite solution (sodium nitrite (16.1 g)/distilled water (30.0 g)) was added dropwise to the resultant mixture so that the internal temperature did not exceed 0° C. After completion of dropwise addition, the reaction mixture was stirred at the same temperature for 15 min, to thereby prepare aqueous diazonium salt solution (E) of interest.

<Diazo Coupling Reaction>

A 3 L-beaker equipped with a thermometer was charged with 4-hydroxyphenetol (30.9 g), pellets of sodium hydroxide (9.0 g) and methanol (500 mL), followed by stirring for dissolution at room temperature. Subsequently, a 30% aqueous sodium hydroxide solution (500 mL) was added to the resultant mixture, and then the internal temperature was cooled to −5° C. After cooling, aqueous diazonium salt solution (E) was gradually added to the mixture so that the internal temperature did not exceed 0° C. After completion of dropwise addition, the reaction mixture was further stirred for 1 hour under cooling. After removal of the coolant used, the reaction mixture was further stirred for 1 hour, and then completion of reaction was confirmed through TLC. After completion of reaction, 1N diluted hydrochloric acid was carefully added to the reaction mixture under stirring to adjust the pH to 7. The precipitated crystals were collected through filtration, and then the thus-obtained crude crystals were stirred three times using distilled water (500 mL) for washing. The thus-obtained crude crystals were recrystallized from isopropyl ether (IPE), to thereby produce 33 g of diazo compound (F) of interest as red-brown crystals (yield: 66%).

<Cyclization Reaction>

A 300-mL three-necked flask equipped with a stirrer, a thermometer and a condenser was charged with diazo compound (F) (10.0 g), sodium azide (4.7 g) and N,N-dimethylformamide (DMF) (150 mL), followed by stirring under heating for 6 hours at an internal temperature of 140° C. After disappearance of starting materials had been confirmed through TLC, 1N diluted hydrochloric acid was added to the reaction mixture so that the pH of the reaction system was adjusted to 7. The resultant mixture was extracted twice with ethyl acetate (200 mL). The ethyl acetate layers were combined with each other, and the mixture was washed sequentially with saturated sodium hydrogen carbonate and saturated brine. The obtained organic layer was dried with sodium sulfate anhydrate. After removal of sodium sulfate anhydrate through filtration, the organic layer was dried with an evaporator. The residue was purified through silica gel column chromatography (hexane/ethyl acetate=15/1), to thereby produce 3.2 g of Compound (N-1) of interest (yield: 35%). The thus-produced compound was found to have a melting point of 139.5° C. and a λmax (methylene chloride) of 354.0 nm.

Synthesis Example 9

Synthesis of Monomer for Forming Heat Resistance Improving Polymer (Heat Resistance Improving Polymer-Forming Monomer) from Compound A-23

A 1,000-mL three-necked flask equipped with a stirrer, a thermometer and a condenser was charged with Compound (A-23) (32.7 g), triethylamine (11.1 g) and tetrahydrofuran (THF) (400 mL). Under cooling with ice water, methacryloyl chloride (11.0 g) was added dropwise to the resultant mixture with a dropping funnel. After completion of dropwise addition, the reaction mixture was stirred at the same temperature for 30 min, and then disappearance of starting materials was confirmed through TLC. After completion of reaction, the reaction mixture was mixed with 2% diluted hydrochloric acid (500 mL) to precipitate crystals. The thus-precipitated crystals were collected through filtration and stirred using distilled water (200 mL) for washing. The obtained crystals were recrystallized from ethyl acetate, to thereby produce 26.1 g of a polymerizable monomer of interest. The thus-produced polymerizable monomer was found to have a melting point of 84.5° C.

Synthesis Example 10

Synthesis of Heat Resistance Improving Polymer-Forming Monomer from Compound F-1

Similar to Synthesis Example 9, a heat resistance improving polymer-forming monomer was synthesized from Compound F-1. The thus-produced monomer was found to have a melting point of 134.8° C.

Synthesis Example 11

Synthesis of Heat Resistance Improving Polymer-Forming Monomer from Compound G-1

Similar to Synthesis Example 9, a heat resistance improving polymer-forming monomer was synthesized from Compound G-1. The thus-produced monomer was found to have a melting point of 73.0° C.

Synthesis Example 12

Synthesis of Heat Resistance Improving Polymer-Forming Monomer from Compound H-1

Similar to Synthesis Example 9, a heat resistance improving polymer-forming monomer was synthesized from Compound H-1. The thus-produced monomer was found to have a melting point of 153.5° C.

Synthesis Example 13

Synthesis of Heat Resistance Improving Polymer-Forming Monomer from Compound I-1

Similar to Synthesis Example 9, a heat resistance improving polymer-forming monomer was synthesized from Compound I-1. The thus-produced monomer was found to have a melting point of 95.3° C.

Synthesis Example 14

Synthesis of Heat Resistance Improving Polymer-Forming Monomer from Compound N-1

Similar to Synthesis Example 9, a heat resistance improving polymer-forming monomer was synthesized from Compound N-1. The thus-produced monomer was found to have a melting point of 82.0° C.

Synthesis Example 15

Synthesis of Heat Resistance Improving Polymer

A 50-mL four-necked flask equipped with a stirrer, a thermometer and a condenser was charged with the polymerizable monomer synthesized in Synthesis Example 9 (9.45 g), hydroxyethyl methacrylate (4.05 g), 1-dodecyl mercaptan (0.68 g), methyl ethyl ketone (11.5 g) and toluene (5.0 g), followed by stirring under argon gas bubbling for degasification. The reaction vessel (eggplant-shaped flask) was heated to 60° C., and then the polymerization initiator V-601 (product of Wako Pure Chemical Industries, Ltd., azobisnitrile compound) (0.20 g) was added thereto. The resultant mixture was continued to be heated/stirred for 6 hours. After disappearance of the starting monomer had been confirmed through TLC, the reaction mixture was cooled to room temperature, to thereby produce a solution of a polymer of interest.

The obtained polymer was found to have a mass average molecular weight (Mw) of 10,270, an Mw/Mn of 1.611 and a hydroxyl value OHV (calculated) of about 130 mgKOH/g.

Synthesis Example 16

Synthesis of Heat Resistance Improving Polymer

Similar to Synthesis Example 15, a polymer of interest was produced from the polymerizable monomer synthesized in Synthesis Example 10. The thus-produced polymer was found to have a mass average molecular weight (Mw) of 10,872, an Mw/Mn of 2.440 and a hydroxyl value OHV (calculated) of about 130 mgKOH/g.

Synthesis Example 17

Synthesis of Heat Resistance Improving Polymer

Similar to Synthesis Example 15, a polymer of interest was produced from the polymerizable monomer synthesized in Synthesis Example 11. The thus-produced polymer was found to have a mass average molecular weight (Mw) of 12,536, an Mw/Mn of 2.087 and a hydroxyl value OHV (calculated) of about 130 mgKOH/g.

Synthesis Example 18

Synthesis of Heat Resistance Improving Polymer

Similar to Synthesis Example 15, a polymer of interest was produced from the polymerizable monomer synthesized in Synthesis Example 12. The thus-produced polymer was found to have a mass average molecular weight (Mw) of 5,256, an Mw/Mn of 1.562 and a hydroxyl value OHV (calculated) of about 130 mgKOH/g.

Synthesis Example 19

Synthesis of Heat Resistance Improving Polymer

Similar to Synthesis Example 15, a polymer of interest was produced from the polymerizable monomer synthesized in Synthesis Example 13. The thus-produced polymer was found to have a mass average molecular weight (Mw) of 3,548, an Mw/Mn of 1.267 and a hydroxyl value OHV (calculated) of about 130 mgKOH/g.

Synthesis Example 20

Synthesis of Heat Resistance Improving Polymer

Similar to Synthesis Example 15, a polymer of interest was produced from the polymerizable monomer synthesized in Synthesis Example 14. The thus-produced polymer was found to have a mass average molecular weight (Mw) of 3,063, an Mw/Mn of 1.196 and a hydroxyl value OHV (calculated) of about 130 mgKOH/g.

Example 1

Formation of Reversible Thermosensitive Recording Layer

2-Anilino-3-methyl-6-diethylaminofluoran: 2 parts by mass
Color developer having the following structural formula: 8 parts by mass

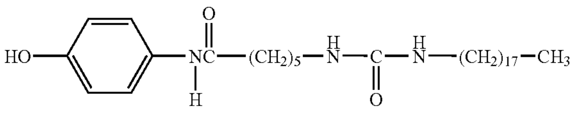

Controlling agent (N,N'-dioctadecyl urea): 2 parts by mass
15% by mass methyl ethyl ketone solution of acrylpolyol resin (hydroxyl value: 70 mgKOH/g, acid value: <1.0 mgKOH/g, mass average molecular weight: 35,000, glass transition temperature: 52° C., hydroxyl group-containing monomer: 2-hydroxyethyl methacrylate): 150 parts by mass
CORONATE HL (product of NIPPON POLYURETHANE INDUSTRIES CO., LTD.): 10 parts by mass The above-listed components were pulverized/dispersed with a ball mill so as to have an average particle diameter of 0.1 μm to 3 μm, to thereby prepare a reversible thermosensitive recording layer-coating liquid.

The thus-obtained reversible thermosensitive recording layer-coating liquid was applied onto the undercoat layer with a wire bar, followed by drying at 100° C. for 1 min and then heating at 60° C. for 24 hours, to thereby form a reversible thermosensitive recording layer having a thickness of 10.0 μm.

<Formation of Heat Resistance Improving Layer>

Compound (A-21): 30 parts by mass 15% by mass methyl ethyl ketone solution of acrylpolyol resin (hydroxyl value: 70 mgKOH/g, acid value: <1.0 mgKOH/g, mass average molecular weight: 35,000, glass transition temperature: 52° C., hydroxyl group-containing monomer: 2-hydroxyethyl methacrylate): 50 parts by mass
CORONATE HL (product of NIPPON POLYURETHANE INDUSTRIES CO., LTD.): 3.5 parts by mass The above-listed components were mixed with one another to prepare a heat resistance improving layer-coating liquid. The thus-obtained heat resistance improving layer-coating liquid was applied onto the reversible thermosensitive recording layer with a wire bar, followed by drying at 100° C. for 1 min and then heating at 60° C. for 24 hours, to thereby form a heat resistance improving layer having a thickness of 3.0 μm.

<Formation of Protective Layer>

Urethane acrylate UV-curable resin (C7-157, product of Dainippon Ink And Chemicals, Incorporated): 15 parts by mass
Ethyl acetate: 85 parts by mass The above-listed components were thoroughly mixed/stirred to prepare a protective layer-coating liquid. The thus-prepared protective layer-coating liquid was applied onto the heat resistance improving layer with a wire bar, followed by drying at 90° C. for 1 min. The thus-applied product was caused to pass under a UV lamp of 80 W/cm (irradiation energy) at a conveyance speed of 9 m/min, to thereby form a protective layer having a thickness of 3 μm. Through the above procedure, a reversible thermosensitive recording medium of Example 1 was produced.

Example 2

The procedure of Example 1 was repeated, except that Compound (A-23) was used instead of Compound (A-21), to thereby produce a reversible thermosensitive recording medium.

Example 3

The procedure of Example 1 was repeated, except that Compound (F-1) was used instead of Compound (A-21), to thereby produce a reversible thermosensitive recording medium.

Example 4

The procedure of Example 1 was repeated, except that Compound (G-1) was used instead of Compound (A-21), to thereby produce a reversible thermosensitive recording medium.

Example 5

The procedure of Example 1 was repeated, except that Compound (H-1) was used instead of Compound (A-21), to thereby produce a reversible thermosensitive recording medium.

Example 6

The procedure of Example 1 was repeated, except that Compound (I-1) was used instead of Compound (A-21), to thereby produce a reversible thermosensitive recording medium.

Example 7

The procedure of Example 1 was repeated, except that Compound (A-16) was used instead of Compound (A-21), to thereby produce a reversible thermosensitive recording medium.

Example 8

The procedure of Example 1 was repeated, except that Compound (N-1) was used instead of Compound (A-21), to thereby produce a reversible thermosensitive recording medium.

Example 9

The procedure of Example 1 was repeated, except that the polymer synthesized from Compound (A-23) in Synthesis Example 15 was used instead of Compound (A-21) and the acrylpolyol resin in the same amount on a solid basis, to thereby produce a reversible thermosensitive recording medium.

Example 10

The procedure of Example 1 was repeated, except that the polymer synthesized from Compound (F-1) in Synthesis Example 16 was used instead of Compound (A-21) and the acrylpolyol resin in the same amount on a solid basis, to thereby produce a reversible thermosensitive recording medium.

Example 11

The procedure of Example 1 was repeated, except that the polymer synthesized from Compound (G-1) in Synthesis Example 17 was used instead of Compound (A-21) and the acrylpolyol resin in the same amount on a solid basis, to thereby produce a reversible thermosensitive recording medium.

Example 12

The procedure of Example 1 was repeated, except that the polymer synthesized from Compound (N-1) in Synthesis Example 20 was used instead of Compound (A-21) and the acrylpolyol resin in the same amount on a solid basis, to thereby produce a reversible thermosensitive recording medium.

Example 13

Preparation of Ethylene-Vinyl Alcohol (EVOH)-Based Gas Barrier Layer-Coating Liquid A 40% by mass EVOH aqueous solution (2.1 parts by mass) was added to a solvent mixture (60 parts by mass) of purified water (50%) and IPA (50%), followed by thoroughly stirring/mixing. Subsequently, montmorillonite (inorganic layered compound) (37.9 parts by mass) was added to the resultant solution under stirring at high speed. A cation-exchange resin (3 parts by mass) was added to the mixture (100 parts by mass). The resultant mixture was stirred for 1 hour at a stirring speed at which the ion-exchange resin was not broken, to thereby remove cationic ions contained therein. Thereafter, the mixture was filtrated with a strainer to remove only the cation-exchange resin.

The mixture prepared through the above procedure was dispersed using a high-pressure disperser at a pressure of 50 MPa, and the resultant dispersion was filtrated with a 300-mesh filter, to thereby prepare gas barrier layer-coating liquid 1 (solid content: 3% by mass) (EVOH/inorganic layered compound=25/75, hereinafter abbreviated as an "EV1").

<Formation of Gas Barrier Layer>

A silane coupling agent (trade name: SH-6062, product of Dow Corning Toray Co., Ltd.) (0.3 parts by mass) was added to the above-prepared EV1 (10 parts by mass), followed by stirring/mixing. Subsequently, the procedure of Example 1 was repeated, except that the polymer synthesized from Compound (A-23) in Synthesis Example 15 was used instead of Compound (A-21) and the acrylpolyol resin in the same amount on a solid basis and that a gas barrier layer having a thickness of 1.0 μm was formed between the heat resistance improving layer and the protective layer, to thereby produce a reversible thermosensitive recording medium. The gas barrier layer was formed as follows: the above-prepared EV1 was applied onto the heat resistance improving layer with a wire bar, followed by drying at 90° C. for 1 min and then heating at 50° C. for 24 hours.

Example 14

The procedure of Example 13 was repeated, except that the polymer synthesized from Compound (A-23) was changed to the polymer synthesized from Compound (F-1) in Synthesis Example 16, to thereby produce a reversible thermosensitive recording medium.

Comparative Example 1

The procedure of Example 1 was repeated, except that Compound (A-21) was changed to Compound (Y) given below, to thereby produce a reversible thermosensitive recording medium.

—Compound (Y)—

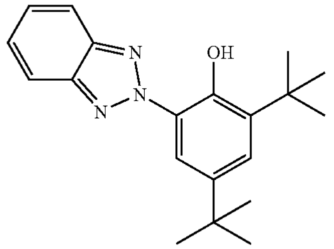

Comparative Example 2

The procedure of Example 1 was repeated, except that Compound (A-21) was changed to Compound (Z) given below, to thereby produce a reversible thermosensitive recording medium.

—Compound (Z)—

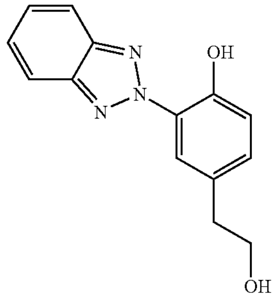

Comparative Example 3

The procedure of Example 9 was repeated, except that the polymer synthesized from Compound (A-23) was changed to a heat resistance improving polymer (PUVA) synthesized as follows, to thereby produce a reversible thermosensitive recording medium.

<Synthesis of Heat Resistance Improving Polymer (PUVA)>

A 50-mL three-necked flask equipped with a stirrer, a thermometer and a condenser was charged with a monomer having the following structural formula (RUVA93) (4.73 g), hydroxyethyl methacrylate (2.02 g), methyl methacrylate (6.75 g), 1-dodecymercaptan (0.68 g), methyl ethyl ketone (11.5 g) and toluene (5.0 g), followed by stirring under argon gas bubbling for degasification. The reaction vessel (egg-plant-shaped flask) was heated to 60° C., and then the polymerization initiator V-601 (product of Wako Pure Chemical Industries, Ltd., azobisnitrile compound) (0.20 g) was added thereto. The resultant mixture was continued to be heated/stirred for 6 hours. After disappearance of the starting monomer had been confirmed through TLC, the reaction mixture was cooled to room temperature, to thereby produce a solution of a polymer of interest.

The obtained polymer was found to have a mass average molecular weight (Mw) of 9,880, an Mw/Mn of 1.421 and a hydroxyl value OHV (calculated) of 65 mgKOH/g.

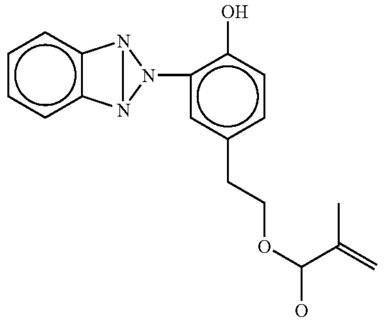

RUVA 93

Comparative Example 4

The procedure of Comparative Example 2 was repeated, except that the same gas barrier layer as formed in Example 13 was provided, to thereby produce a reversible thermosensitive recording medium.

Comparative Example 5

Heat Resistance Improving Polymer Disclosed in JP-A No. 2007-138184

The procedure of Example 9 was repeated, except that the polymer synthesized from Compound (A-23) was changed to the following heat resistance improving polymer, to thereby produce a reversible thermosensitive recording medium.

The heat resistance improving polymer used in Comparative Example 5 can be produced as follows. Specifically, a heat resistance improving polymer-forming monomer is produced from a compound having the following structural formula in a manner similar to that employed in Synthesis Example 9, and the thus-produced monomer is treated in a manner similar to that employed in Comparative Example 3.

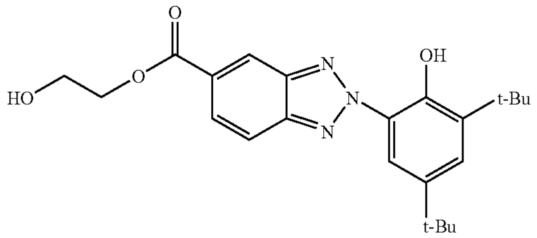

Next, each of the above-produced reversible thermosensitive recording media was subjected to (Evaluation 1) to (Evaluation 3) and evaluated for transmittance with respect to UV as follows. The results are shown in Table 1.

<(Evaluation 1): Image Density and Degree of Residual Image after Erasing>

Each of the reversible thermosensitive recording media was subjected to image printing/erasing with a thermosensitive printing simulator employing an end surface-type thermal head (KSB320AA (resistivity: 1,206Ω), product of KYOCERA Corporation) and a ceramic heater (width: 4 mm) under the following conditions, followed by measuring for image density using the Macbeth densitometer RD-914.

Evaluation conditions: printing speed: 12.7 cm/s, sub-scan density: 8 dot/mm

Image density: maximum image density measured when printing was performed while an energy applied (voltage) was changed in 1 V steps Image density after erasing: minimum image density measured when a solid image formed at an energy level at which the maximum image density had been attained was erased by the ceramic heater with the temperature thereof being changed in 5° C. steps <(Evaluation 2): Heat Resistance after Repetitive Printing/Erasing>

Each of the reversible thermosensitive recording media was repeatedly subjected to image printing/erasing 100 times using the card printer KU-R2800 (product of Panasonic Communications Co., Ltd.). The surface of the reversible thermosensitive recording medium having undergone 100-time printing/erasing was visually observed and evaluated according to the following evaluation criteria.

[Evaluation Criteria]

A: Good color development observed in image portions, good color erasure observed after erasing, and no damage observed on medium B: Good color development and erasure observed, but damage slightly observed on medium C: Damage observed on medium, medium turned into brown due to thermal fatigue, color density decreased, and insufficient color erasure observed D: Severe damage observed on medium, medium considerably turned into brown, and evaluation for heat resistance after repetitive printing/erasing could not be continued <(Evaluation 3): Light Resistance>

Each of the reversible thermosensitive recording media was subjected to color image formation similar to Evaluation 1. The obtained medium was exposed to xenon light using an artificial sunlight irradiating device (product of SERIC LTD.) (illuminance: 130,000 Lx, time: 144 hours, temperature: 30° C., humidity: 85% RH). Similar to (Evaluation 1), the medium obtained after light exposure was measured for its image density, and its image density after erasure.

<Measurement of UV Transmittance>

The UV transmittance (i.e., transmittance with respect to light of 390 nm) of each heat resistance improving layer was measured using Spectrophotometer U-4100 (product of Hitachi, Ltd.) with being set to a transmission mode. Here, a measurement sample was prepared by applying the heat resistance improving layer-coating liquid used in each of Examples and Comparative Examples, onto a transparent film having no absorption with respect to light of 390 nm so as to have a thickness of 3 μm. Note that this measurement was performed using the same transparent film as reference.

TABLE 1

| | Evaluation 1 | | | Evaluation 3 | | |
|---|---|---|---|---|---|---|
| | Image density | Density after erasure | Evaluation 2 Durability | Image density | Density after erasure | UV transmittance (%) |
| Ex. 1 | 1.44 | 0.06 | B | 1.30 | 0.08 | 16% |
| Ex. 2 | 1.43 | 0.06 | B | 1.30 | 0.08 | 15% |
| Ex. 3 | 1.42 | 0.06 | B | 1.26 | 0.08 | 18% |
| Ex. 4 | 1.42 | 0.06 | B | 1.27 | 0.08 | 18% |
| Ex. 5 | 1.42 | 0.06 | B | 1.28 | 0.08 | 20% |
| Ex. 6 | 1.42 | 0.06 | B | 1.29 | 0.08 | 20% |
| Ex. 7 | 1.42 | 0.06 | B | 1.20 | 0.11 | 22% |
| Ex. 8 | 1.43 | 0.06 | B | 1.25 | 0.09 | 14% |
| Ex. 9 | 1.44 | 0.06 | A | 1.39 | 0.07 | 9% |
| Ex. 10 | 1.40 | 0.06 | A | 1.37 | 0.08 | 12% |
| Ex. 11 | 1.40 | 0.07 | A | 1.36 | 0.09 | 16% |
| Ex. 12 | 1.42 | 0.06 | A | 1.32 | 0.09 | 8% |
| Ex. 13 | 1.37 | 0.07 | A | 1.35 | 0.06 | 9% |
| Ex. 14 | 1.33 | 0.07 | A | 1.32 | 0.07 | 12% |
| Comp. Ex. 1 | 1.45 | 0.06 | D | 0.55 | 0.24 | 30% |
| Comp. Ex. 2 | 1.45 | 0.06 | B | 0.95 | 0.24 | 88% |
| Comp. Ex. 3 | 1.46 | 0.06 | C | 0.96 | 0.25 | 85% |
| Comp. Ex. 4 | 1.36 | 0.07 | C | 1.01 | 0.17 | 85% |
| Comp. Ex. 5 | 1.46 | 0.1 | C | 1.08 | 0.26 | 18% |

In the reversible thermosensitive recording medium of the present invention, the card-shaped medium is used as, for example, a prepaid card, a point card and a credit card. The sheet-shaped medium having a sheet size larger than a card size can be used as a general document, an instruction for process management, etc. The reversible thermosensitive recording medium of the present invention, therefore, can be widely used as, for example, an admission ticket and a sticker for frozen-food containers, industrial products, various chemical containers, etc. In addition, it can be also used as a large screen and various displays for logistic control, manufacturing process management, etc.

What is claimed is:

1. A heat resistance improver comprising:

a heat resistance improving component which has a benzotriazole skeleton having an electron attractive group and a reactive aliphatic hydroxyl group, wherein the heat resistance improving component is a compound represented by the following General Formula (2):

General Formula (2)

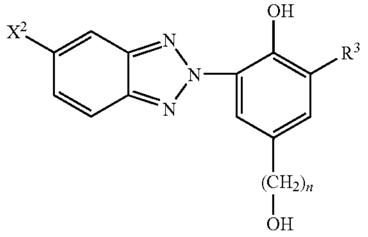

where $X^2$ represents a hydrogen atom, a halogen atom, $—NO_2$, —CN, $—CF_3$ or an alkyloxycarbonyl group; $R^3$ represents a hydrogen atom, a linear or branched alkyl group having 1 to 8 carbon atoms, —CHO or $—CH═N—R^4$, where $R^4$ represents an alkyl group, an aryl group, an alkenyl group or an aralkyl group each of which may have a substituent; and n is an integer of 1 to 8; with the proviso that when $X^2$ is a hydrogen atom or halogen atom, then $R^3$ is —CHO or $—CH═N—R^4$.

2. The heat resistance improver according to claim 1, wherein $X^2$ is a linear or branched alkyloxycarbonyl group having 1 to 6 carbon atoms.

3. A heat resistance improver comprising:

a heat resistance proving component which has a benzotriazole skeleton having an electron attractive group and a reactive aliphatic hydroxyl group, wherein the heat resistance improving component is a reactive hydroxyl group-containing polymer produced through polymerization of at least a compound represented by the following General Formula (3) and hydroxyalkyl(meth)acrylate:

General Formula (3)

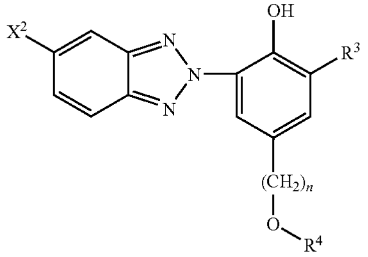

where $X^2$ represents a hydrogen atom, a halogen atom, $—NO_2$, —CN, $—CF_3$ or an alkyloxycarbonyl group; $R^3$ represents a hydrogen atom, a linear or branched alkyl group having 1 to 8 carbon atoms, —CHO or $CH═N—R^4$, where $R^4$ represents an alkyl group, an aryl group, an alkenyl group or an aralkyl group each of which may have a substituent; n is an integer of 1 to 8; with the proviso that when $X^2$ is a hydrogen atom or halogen, then $R^3$ is —CHO or $—CH═N—R^4$; and $R^4$ represents a polymerizable unsaturated hydrocarbon group.

4. The heat resistance improver according to claim 3, wherein the heat resistance improving component is a compound represented by the following General Formula (4):

General Formula (4)

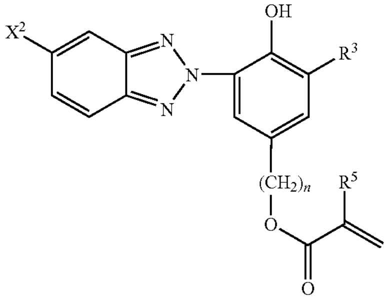

where $X^2$, n and $R^3$ have the same meanings as defined in General Formula (3); and $R^5$ represents a hydrogen atom or a methyl group.

5. The heat resistance improver according to claim 3, wherein the polymer has a mass average molecular weight of 1,000 to 200,000.

6. The heat resistance improver according to claim 3, wherein the polymer has a hydroxyl value of 100 mgKOH/g or higher and an acid value of 5 mgKOH/g or lower.

7. A heat resistance improver comprising:

a heat resistance improving component which has a benzotriazole skeleton which has a reactive aliphatic hydroxyl group, wherein the heat resistance improving component is a compound represented by the following General Formula (5):

General Formula (5)

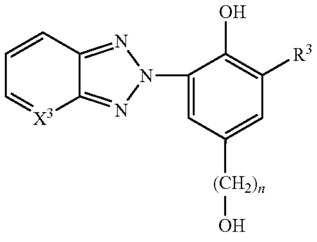

where $X^3$ represents an electronegative atom; $R^3$ represents a hydrogen atom, a linear or branched alkyl group having 1 to 8 carbon atoms, —CHO or —CH═N—$R^4$, where $R^4$ represents an alkyl group, an aryl group, an aralkyl group or an alkenyl group or an aralkyl group each of which may have a substituent; and n is an integer of 1 to 8.

8. The heat resistance improver according to claim 7, wherein the heat resistance improving component is a compound represented by the following General Formula (6):

General Formula (6)

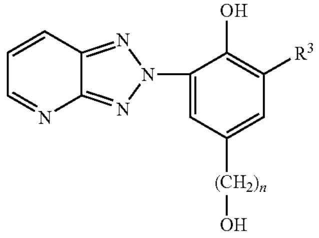

where $R^3$ and n have the same meanings as defined in General Formula (5).

9. A heat resistance improver comprising:

a heat resistance improving component which has a benzotriazole skeleton which has a reactive aliphatic hydroxyl group, wherein the heat resistance improving component is a reactive hydroxyl group-containing polymer produced through polymerization of at least a compound represented by the following General Formula (7) and hydroxyalkyl(meth)acrylate:

General Formula (7)

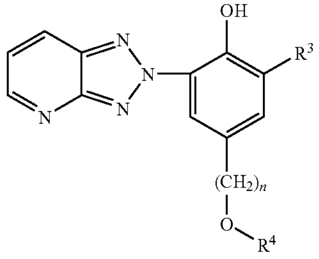

where $R^3$ represents a hydrogen atom, a linear or branched alkyl group having 1 to 8 carbon atoms, —CHO or —CH═N—$R^4$, where $R^4$ represents an alkyl group, an aryl group, an alkenyl group or an aralkyl group each of which may have a substituent; n is an integer of 1 to 8; and $R^4$ represents a polymerizable unsaturated hydrocarbon group.

10. The heat resistance improver according to claim 9, wherein the heat resistance improving component is a polymer produced through polymerization between a compound represented by the following General Formula (8) and hydroxyalkyl(meth)acrylate:

General Formula (8)

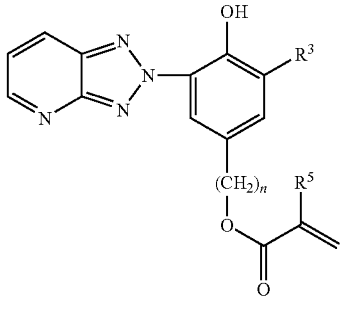

where $R^3$ and n have the same meanings as defined in General Formula (7); and $R^5$ represents a hydrogen atom or a methyl group.

* * * * *